US010301652B2

(12) United States Patent
Pachapur et al.

(10) Patent No.: US 10,301,652 B2
(45) Date of Patent: May 28, 2019

(54) PROCESS FOR HYDROGEN PRODUCTION FROM GLYCEROL

(71) Applicants: CENTRE DE RECHERCHE INDUSTRIELLE DU QUEBEC (CRIQ), Quebec (CA); INSTITUT NATIONAL DE LA RECHERCHE SCIENTIFIQUE, Quebec (CA)

(72) Inventors: Vinayak Pachapur, Belgaum (IN); Saurabh Jyoti Sarma, Darrang District (IN); Sampa Maiti, Purba Medinipur District (IN); Satinder Kaur Brar, Quebec (CA); Yann Lebihan, Quebec (CA); Gerardo Buelna, Quebec (CA); Mausam Verma, Quebec (CA); Ratul Kumar Das, Kamrup District (IN)

(*) Notice: Subject to any disclaimer, the term of this patent is extended or adjusted under 35 U.S.C. 154(b) by 91 days.

(21) Appl. No.: 15/294,180

(22) Filed: Oct. 14, 2016

(65) Prior Publication Data
US 2018/0105836 A1 Apr. 19, 2018

(51) Int. Cl.
C12P 3/00 (2006.01)
(52) U.S. Cl.
CPC ....................... *C12P 3/00* (2013.01)
(58) Field of Classification Search
CPC ........................................................ C12P 3/00
USPC ............. 435/29, 34, 41, 168, 170, 180, 243, 435/252.4, 252.7
IPC ........................................................ C12P 3/00
See application file for complete search history.

(56) References Cited

U.S. PATENT DOCUMENTS

| 8,129,157 B2 | 6/2012 | Gonzalez |
| 2014/0295515 A1 | 2/2014 | Varrone |

FOREIGN PATENT DOCUMENTS

| CA | 2804738 A1 | 1/2011 |
| WO | 201031793 A2 | 3/2010 |
| WO | WO2016040074 A1 * | 3/2016 |

OTHER PUBLICATIONS

Jitrwung et al. 2011. Optimization of media composition for the production of biohydrogen from waste glycerol. International Journal of Hydrogen Energy, vol. 36, pp. 9602-9611 (Year: 2011).*
Zhang J. et al., "Lime mud from paper-making process addition to food waste synergistically enhances hydrogen fermentation performance", International Journal of Hydrogen Energy, 2013, vol. 38, pp. 2738-2745. (Year: 2013).*
"Egg farmers of Canada Annual Report", 2015.
Athalye et al. "Use of biodiesel-derived crude glycerol for producing eicosapentaenoic acid (EPA) by the fungus *Pythium irregulare*." Journal of Agricultural and Food Chemistry. Mar. 6, 2009; vol. 57 No. 7, pp. 2739-2744.
Ayoub et al. "Critical review on the current scenario and significance of crude glycerol resulting from biodiesel industry towards more sustainable renewable energy industry." Renewable and Sustainable Energy Reviews. Mar. 22, 2012, vol. 16, pp. 2671-2686.
Boonchan et al. "Surfactant-enhanced biodegradation of high molecular weight polycyclic aromatic hydrocarbons by Stenotrophomonas maltophilia." Biotechnology and Bioengineering, 1998; vol. 59, pp. 482-494.
Chen et al. "Ultrasonic-assisted production of biodiesel from transesterification of palm oil over ostrich eggshell-derived CaO catalysts." Bioresource Technology. Aug. 30, 2014; vol. 171, pp. 428-432.
Chi et al. "A laboratory study of producing docosahexaenoic acid from biodiesel-waste glycerol by microalgal fermentation." Process Biochemistry. 2007; vol. 42, No. 11, pp. 1537-1545.
Chu et al. "Direct fermentation of sweet potato to produce maximal hydrogen and ethanol." Applied Energy. Jul. 12, 2012; vol. 100, pp. 10-18.
Djukic-Vukovic et al. "Wastes from bioethanol and beer productions as substrates for L(+) lactic acid production—A comparative study." Waste Management. Nov. 28, 2015; vol. 48, pp. 478-482.
Elsamadony et al. "Surfactant-enhanced biohydrogen production from organic fraction of municipal solid waste (OFMSW) via dry anaerobic digestion." Applied Energy. vol. 149, pp. 272-282.
Ethier et al. "Continuous culture of the microalgae *Schizochytrium limacinum* on biodiesel-derived crude glycerol for producing docosahexaenoic acid." Bioresource Technology. 2011; vol. 102, pp. 88-93.
Fathima et al. "Direct utilization of waste water algal biomass for ethanol production by cellulolytic *Clostridium phytofermentans* DSM 1183." Bioresource Technology. 2016; vol. 202, pp. 253-256.
Van Ginkel et al. "Biohydrogen Production as a Function of pH and Substrate Concentration." Environmental Science & Technology. 2001; vol. 35, pp. 4726-4730.
Goes et al. "Effect of surfactants on a-amylase production in a solid substrate fermentation process." Journal of Chemical Technology and Biotechnology. 1999; vol. 74. pp. 709-712.
Heyndrickx et al. "The fermentation of glycerol by *Clostridium butyricum* LMG 1212t2 and 1213t1 and *C. pasteurianum* LMG 3285." Applied Microbiology and Biotechnology. 1991; vol. 34, No. 5, pp. 637-642.
Ito et al. "Hydrogen and Ethanol Production from Glycerol-Containing Wastes Discharged after Biodiesel Manufacturing process." Journal of Bioscience and Bioengineering. 2005; vol. 100, No. 3, pp. 260-265.

(Continued)

*Primary Examiner* — Satyendra K Singh
(74) *Attorney, Agent, or Firm* — Benoît & CôtéInc.

(57) ABSTRACT

The present document describes a process for production of hydrogen gas ($H_2$) from fermentation of crude glycerol with a hydrogen producing microorganism in a bioreactor. The process comprises the step of introducing a volume of crude glycerol in a fermentation mixture which comprises a fermentation medium comprised of crude glycerol and hydrogen producing microorganisms under a fermentative hydrogen production condition, and then removing a volume of the fermentation mixture equal to the second volume of the crude glycerol, to maintain constant the total volume of the fermentation mixture.

21 Claims, 11 Drawing Sheets

(56) References Cited

OTHER PUBLICATIONS

Jung et al. "Hydrogen production by a new chemoheterotrophic bacterium *Citrobacter* sp. Y19." International Journal of Hydrogen Energy. 2002; vol. 27. pp. 601-610.

Kumar et al. "Valorization of Egg Shell Biowaste and Brewery Wastewater for the Enhanced Production of Fumaric Acid." Waste Biomass Valor. 2015; vol. 6, No. 4, pp. 535-546.

Lee et al. "Effect of surfactants on ethanol fermentation using glucose and cellulosic hydrolyzates." Biotechnology Letters. Mar. 1996; vol. 18, No. 3, pp. 299-304.

Pachapur et al. "Co-culture strategies for increased biohydrogen production. " International Journal of Energy Research. 2015; vol. 39, No. 11, pp. 1479-1504.

Pachapur et al. "Biohydrogen production by co-fermentation of crude glycerol and apple pomace hydrolysate using co-culture of Enterobacter aerogenes and Clostridium butyricum." Bioresource Technology. 2015; vol. 193, pp. 297-306.

Pachapur et al. "Evidence of metabolic shift on hydrogen, ethanol and 1,3-propanediol production from crude glycerol by nitrogen sparging under micro-aerobic conditions using co-culture of Enterobacter aerogenes and Clostridium butyricum." International Journal of Hydrogen Energy. 2015; vol. 40, pp. 8869-8676.

Patel et al. "Dark fermentative hydrogen production by defined mixed microbial cultures immobilized on ligno-cellulosic waste materials." International Journal of Hydrogen Energy. 2010; vol. 35, No. 19, pp. 10674-10681.

Patel et al. "Hydrogen and Polyhydroxybutyrate Producing Abilities of *Bacillus* spp. From Glucose in Two Stage System.". Indian Journal of Microbiology. Oct.-Dec. 2011; vol. 51, No. 4, pp. 418-423.

Patel et al. "Exploitation of defined bacterial cultures for production of hydrogen and polyhydroxybutyrate from pea-shells." Biomass and Bioenergy, 2012; vol. 36, pp. 218-225.

Patel et al. "Enhancement in hydrogen production by co-cultures of Bacillus and Enterobacter." International Journal of Hydrogen Energy. 2014; vol. 39, No. 27, pp. 14663-14668.

Podstawczyk et al. "Biosorption of malachite green by eggshells: Mechanism identification and process optimization." Bioresource Technology. 2014; vol. 160, pp. 161-165.

Reese et al. "Surfactants as Stimulants of Enzyme Production by Microorganisms." Applied Microbiology. 1969; vol. 17, No. 2, pp. 242-245.

Roy et al. "Continuous thermophilic biohydrogen production in packed bed reactor." Applied Energy. vol. 136, pp. 51-58.

Sabourin-Provost et al. "High yield conversion of a crude glycerol fraction from biodiesel production to hydrogen by phtofermentation." Bioresource Technology.2009; vol. 100, pp. 3513-3517.

Sacia et al. "Synthesis and Regeneration of Sustainable CaO Sorbents from Chicken Eggshells for Enhanced Carbon Dioxide Capture." ACS Sustainable Chemistry & Engineering. 2013; vol. 1, pp. 903-909.

Sakai et al. "Microbial Production of Hydrogen and Ethanol from Glycerol-Containing Wastes Discharged From a Biodiesel Fuel Production Plant in a Bioelectrochemical Reactor with Thionine." Biotechnology and Bioengineering. Oct. 1, 2007; vol. 98, No. 2, pp. 340-348.

Sargsyan et al. "Novel approach of ethanol waste utilization: Biohydrogen production by mixed cultures of dark-and photo-fermentative bacteria using distillers grains." International Journal of Hydrogen Energy. 2016; vol. 41, No. 4, pp. 2377-2382.

Sarkar et al. "Bioethanol production from agricultural wastes: An overview." Renewable Energy. 2012; vol. 37, pp. 19-27.

Sarma et al. "Bio-hydrogen production by biodiesel-derived crude glycerol bioconversion: a techno-economic evaluation." Bioprocess and Biosystems Engineering. 2012; vol. 36, No. 1, pp. 1-10.

Sarma et al. "Microbial hydrogen production by bioconversion of crude glycerol: A review." International Journal of Hydrogen Energy. 2012; vol. 37, pp. 6473-6490.

Sarma et al. "Hydrogen production from meat processing and restaurant waste derived crude glycerol by anaerobic fermentation and utilization of the spent broth." Journal of Chemical Technology and Biotechnology. 2013; vol. 88, No. 12, pp. 2264-2271.

Sarma et al. "Liquid waste from biohydrogen production—A commercially attractive alternative for phosphate solubilizing biofertilizer." International Journal of Hydrogen Energy. 2013; vol. 38, pp. 8704-8707.

Sarma et al. "Evaluation of different supplementary nutrients for enhanced biohydrogen production by Enterobacter aerogenes NRRL B 407 using waste derived crude glycerol." International Journal of Hydrogen Energy. 2013; vol. 38, pp. 2191-2198.

Sarma et al. "Enriched hydrogen production by bioconversion of biodiesel waste supplemented with ferric citrate and its nano-spray dried particles." RSC Adv., 2014; vol. 4, pp. 49588-49594.

Sarma et al. "Application of magnesium sulfate and its nanoparticles for enhanced lipid production by mixotrophic cultivation of algae using biodiesel waste." Energy. 2014; vol. 78, No. 15, pp. 16-22.

Sarma et al. "Mitigation of the inhibitory effect of soap by magnesium salt treatment of crude glycerol—A novel approach for enhanced biohydrogen production from the biodiesel industry waste." Bioresource Technology. 2014; vol. 151, pp. 49-53.

Sarma et al. "A novel anaerobic two-phase system for biohydrogen production and in situ extraction of organic acid byproducts." Bioprocess and Biosystems Engineering. 2015.

Sarma et al. "Hydrogen biorefinery: Potential utilization of the liquid waste from fermentative hydrogen production." Renewable and Sustainable Energy Reviews. 2015; vol. 50, pp. 942-951.

Levin et al. "Biohydrogen production: prospects and limitations to practical application." International Journal of Hydrogen Energy. 2004; vol. 29, pp. 173-185.

Liu et al. "Hydrogen and methane production from household solid waste in the two-stage fermentation process." Water Research. 2006; vol. 40, pp. 2230-2236.

Selembo et al. "Enhanced Hydrogen and 1,3-Propanediol Production From Glycerol by Fermentation Using Mixed Cultures." Biotechnology and Bioengineering. 2009; vol. 104, No. 6, pp. 1098-1106.

Sivagurunathan et al. "A critical review on issues and overcoming strategies for the enhancement of dark fermentative hydrogen production in continuous systems." International Journal of Hydrogen Energy. 2016; vol. 41, No. 6. pp. 3820-3836.

Tenca et al. "Biohydrogen from thermophilic co-fermentation of swine manure with fruit and vegetable waste: Maximizing stable production without pH control." Bioresource Technology. 2011; vol. 102, No. 18, pp. 8582-8588.

Van Ginkel et al. "Increased biological hydrogen production with reduced organic loading." Water Research. 2005; vol. 39, pp. 3819-3826.

Vankateswara et al. "Valorization of fatty acid waste for bioplastics production using Bacillus tequilensis: Integration with dark-fermentative hydrogen production process." International Journal of Hydrogen Energy. 2014; vol. 39, No. 14, pp. 7616-7626.

Wang et al. "Effects of non-ionic surfactant and associative thickener on the rheology of polyacrylamide in aqueous glycerol solutions." Colloid and Polymer Science. 1996; vol. 274, pp. 138-144.

Wei et al. "Application of waste eggshell as low-cost solid catalyst for biodiesel production." Bioresource Technology. 2009; pp. 2883-2885.

Yang et al. "Value-added uses for crude glycerol—a byproduct of biodiesel production." Biotechnology for Biofuels. 2012; vol. 5, No. 13.

Yokoi et al. "H-2 production from starch by a mixed culture of Clostridium butyricum and Enterobacter aerogenes." Biotechnology Letters. Feb. 1998; vol. 20, No. 2, pp. 143-147.

Yokoi et al. "Microbial hydrogen production from sweet potato starch residue." Journal of Bioscience and Bioengineering. 2001; vol. 91, No. 1, pp. 58-63.

Yokoi et al. "Microbial production of hydrogen from starch-manufacturing wastes." Biomass and Bioenergy. 2002; vol. 22, No. 5, pp. 389-395.

(56) References Cited

OTHER PUBLICATIONS

Jitrwung et al. "Biohydrogen and Bioethanol Production from Biodiesel-Based Glycerol by Enterobacter aerogenes in a Continuous Stir Tank Reactor", International Journal of Molecular Sciences. 2015; 16, pp. 10650-10664.

Kumar et al. "Recent insights into the cell immobilization technology applied for dark fermentive hydrogen production", Bioresource Technology. 2016; vol. 219, pp. 725-737.

Jung et al. "Bioreactor design for continuous dark fermentative hydrogen production", Bioresource Technology. 2011; vol. 102, pp. 8612-8620.

Taoka et al. "Effect of Tween 80 on the growth, lipid accumulation and fatty acid composition of Thraustochytrium aureum ATCC 34304", Journal of Bioscience and Bioengineering. 2011; vol. 111, Issue 4, pp. 420-424.

Marques et al. "Bio-hydrogen production from glycerol by a strain of Enterobacter aerogenes." Hypothesis VIII. Apr. 1-3, 2009; Lisbon.

Morsy et al. "CO2-free biohydrogen production by mixed dark and photofermentation bacteria from sorghum starch using a modified simple purification and collection system." Energy. 2015; vol. 87, pp. 594-604.

Nath et al. "Hydrogen production by Rhodobacter sphaeroides strain O.U.001 using spent media of Enterobacter cloacae strain DM11." Applied microbiology and biotechnology. 2005; vol. 68, pp. 533-541.

Ngo et al. "High-yield biohydrogen production from biodiesel manufacturing waste by Thermotoga neapolitana." International Journal of Hydrogen Energy. 2011; vol. 36, pp. 5836-5842.

Ohnishi et al. "Development of a simple bio-hydrogen production system through dark fermentation by using unique microflora." International Journal of Hydrogen Energy. 2010; vol. 35, pp. 8544-8553.

\* cited by examiner

PROCESS FOR HYDROGEN PRODUCTION FROM GLYCEROL

BACKGROUND

(a) Field

The subject matter disclosed generally relates to a process for production of hydrogen gas ($H_2$) from fermentation of crude glycerol with a hydrogen producing microorganism in a bioreactor. More specifically, the subject matter relates to a process where a volume of crude glycerol is introduced into a fermentation mixture, while an equivalent volume of the mixture is withdrawn.

(b) Related Prior Art

Hydrogen will be able to contribute in greenhouse gas emission reduction since it is a carbon free fuel and water is the major byproduct of its combustion, if commercially used as a replacement of present fossil derived energy carriers. It has a gravimetric energy density of 142 MJ/kg; which is higher than the common fuels, such as gasoline (47 MJ/kg) and diesel (43 MJ/kg). In this context, hydrogen production by environmentally friendly technology, such as bioconversion of biomass, carries tremendous industrial opportunity. By using different agro-industrial waste materials as the feedstock, in order to get maximum benefit of the technology, biohydrogen production process can be visualized as a sustainable strategy for organic waste management. Considering this fact, crude glycerol (CG), the major by-product of the transesterification process of lipid used for biodiesel production has been evaluated as a substrate for fermentative hydrogen production. In a typical biodiesel production process, production of 100 kg of biodiesel is accompanied by co-production of nearly 10-11 kg of CG. CG is mainly a mixture of different compounds, such as glycerol, monoglyceride, diglyceride, methanol, soap, and catalysts used for transesterification. Corresponding to increase in global biodiesel production, CG production has also seen a rise. Owing to its increased availability and relatively complex composition, CG price can be as low as $0.05/pound (Yang et al. (2012). Value-added uses for crude glycerol—a byproduct of biodiesel production. Biotechnology for biofuels, 5(13), 1.). Thus, in addition to environmental benefits, successful application of CG as a feedstock for hydrogen production may serve as a mean of its valorization.

However, high process cost is a serious setback to hydrogen production by CG bioconversion. It has been observed that the cost of synthetic media components could be as high as 82% of total cost of such a process (Sarma et al. Bio-hydrogen production by biodiesel-derived crude glycerol bioconversion: a techno-economic evaluation. Bioprocess and biosystems engineering, 36(1), 1-10.). Therefore, it would be desirable to develop a highly efficient low cost hydrogen production process using CG as the sole carbon and nutrient source. Substrate inhibition is another serious challenge of CG based biohydrogen production process. For a batch hydrogen production process, 10 g/L CG has been found to be optimum for hydrogen production (Sarma et al. (2013). Hydrogen production from meat processing and restaurant waste derived crude glycerol by anaerobic fermentation and utilization of the spent broth. Journal of Chemical Technology and Biotechnology, 88(12), 2264-2271.), wherein significant differences in glycerol content, pH and elemental composition were observed between soybean oil based and meat processing and restaurant waste based CG. Corresponding to an increase in initial CG concentration from 10 to 15 and 20 g/L, any significant improvement in hydrogen production has not been observed.[12] Therefore, by simply doubling the substrate concentration from 10 g/L to 20 g/L, it was not possible to double the amount of hydrogen production per liter of medium. Therefore, the process must be performed at a relatively low initial substrate concentration, which results in increased process cost by increasing the media volume.

In addition to substrate inhibition, the requirement of large volumes of media/water, and high process cost, sharp decrease in process pH due to byproduct accumulation, and product ($H_2$) inhibition are some major challenges in hydrogen production by crude glycerol bioconversion. If a process is developed without considering any one of these factors, it affects overall effectiveness of such process. In order to get maximum benefit of the technology, therefore, all these challenges should be addressed at a time. Furthermore, scaling up of such technologies to industrial level by an economically viable way is also challenge in biohydrogen research.

Microbial hydrogen production using co-culture delivers advantages with higher yield in lesser time, perform complex functions, ensure stability and better performance in comparison to mono- or mixed-culture systems (Pachapur et al. (2015). Co-culture strategies for increased biohydrogen production. International Journal of Energy Research, 39(11), 1479-1504.). Previous studies using co-culture system resulted in increased hydrogen production in comparison to monoculture system (Pachapur et al. Biohydrogen production by co-fermentation of crude glycerol and apple pomace hydrolysate using co-culture of *Enterobacter aerogenes* and *Clostridium butyricum*. Bioresource Technology, 193 (2015) 297-306; and Pachapur et al. Evidence of metabolic shift on hydrogen, ethanol and 1, 3-propanediol production from crude glycerol by nitrogen sparging under micro-aerobic conditions using co-culture of *Enterobacter aerogenes* and *Clostridium butyricum*. International Journal of Hydrogen Energy, 40 (2015) 8669-8676).

Microbial hydrogen production is influenced by the crude glycerol characteristics and composition of major impurities, such as methanol and soap (Ito et al. Hydrogen and ethanol production from glycerol-containing wastes discharged after biodiesel manufacturing process. Journal of Bioscience and Bioengineering, 100 (2005) 260-265 and Ngo et al. High-yield biohydrogen production from biodiesel manufacturing waste by *Thermotoga neapolitana*. International Journal of Hydrogen Energy, 36 (2011) 5836-5842). Methanol inhibition is taken care of during media sterilization (Sarma et al. Microbial hydrogen production by bioconversion of crude glycerol: A review. International Journal of Hydrogen Energy, 37 (2012) 6473-6490). Effect of soap is lessened by initial pretreatment step of decreasing viscosity of crude glycerol by mixing with distilled water (e.g. 1:4 v/v), followed by pH adjustment and centrifugation step to remove precipitated free fatty acids (Athalye et al. Use of biodiesel-derived crude glycerol for producing eicosapentaenoic acid (EPA) by the fungus *Pythium irregulare*. Journal of Agricultural and Food Chemistry, 57 (2009) 2739-2744). However, removal of soap resulted in decreased hydrogen production, suggesting that soap presence played a role of buffering agent and had beneficial effect on glycerol utilization by the microorganisms (Sarma et al. (2014). Mitigation of the inhibitory effect of soap by magnesium salt treatment of crude glycerol—A novel approach for enhanced biohydrogen production from the biodiesel industry waste. Bioresource technology, 151, 49-53). Addition of surfactant at low concentration in the glycerol media reduces the surface tension, thereby decreasing the viscosity of the solution (Wang et al. Effects of nonionic surfactant and associative thickener on the rheology of polyacrylamide in aqueous glycerol solutions. Colloid and Polymer Science, 274 (1996) 138-144; Ethier, K. Woisard, D. Vaughan, Z. Wen, Continuous culture of the microalgae Schizochytrium limacinum on biodiesel-derived crude glycerol for producing docosahexaenoic acid, Bioresource Technology, 102 (2011) 88-93. During pretreatment of crude glycerol before hydrogen production, the viscosity of crude glycerol is decreased by mixing with distilled water (Sarma et al. Microbial hydrogen production by bioconversion of crude glycerol: A review, International Journal of Hydrogen Energy, 37 (2012) 6473-6490). During additional pretreatment step with decreasing the viscosity of crude glycerol, the pretreated crude glycerol will be promising feedstock for microbial fermentation in producing value-added products (Chi, D. Pyle, Z. Wen, C. Frear, S. Chen, A laboratory study of producing docosahexaenoic acid from biodiesel-waste glycerol by microalgal fermentation, Process Biochemistry, 42 (2007) 1537-1545; and Ethier, K. Woisard, D. Vaughan, Z. Wen, Continuous culture of the microalgae Schizochytrium limacinum on biodiesel-derived crude glycerol for producing docosahexaenoic acid, Bioresource Technology, 102 (2011) 88-93).

The bioconversion of crude glycerol to hydrogen production is influenced by co-culture, mixed-culture and photo-fermentation systems. Each of the systems has advantages and disadvantages over the other. The co-culture system works in harmony, reduces the fermentation time, performs complex functions and produces more hydrogen in comparison to mono-culture system (Pachapur et al. (2015). "Co-culture strategies for increased biohydrogen production." International Journal of Energy Research 39(11): 1479-1504). The dark fermentation carried out using mixed-culture system have broader variety of potential substrate, including refuse and waste products during hydrogen production (Nath et al (2005). Hydrogen production by Rhodobacter sphaeroides strain OU 001 using spent media of Enterobacter cloacae strain DM11. Applied microbiology and biotechnology 68(4): 533-541). Photo-fermentation has advantages with high theoretical conversion ability and utilization of organic acids (acetate, butyrate) or solvents (acetone, butanol) produced during dark fermentation.

Dark fermentation of $H_2$ production attributes towards broad spectra of organic wastes, requiring simple reactor set-up and in absence of light, favour efficient $H_2$ production in comparison to photo-fermentation. During dark fermentation, production of organic acids causes a sharp decrease in the medium pH and results in lower $H_2$ production (Ginkel et al. Biohydrogen production as a function of pH and substrate concentration. Environ. Sci. Technol. 2001, 35 (24), 4726-4730). Thus, to maintain the fermentation pH, addition of external buffering agents is unavoidable. Improvements during fermentation requiring additional media components, co-substrate utilization and immobilization techniques are necessary for increased $H_2$ production (Sivagurunathan et al. (2016). A critical review on issues and overcoming strategies for the enhancement of dark fermentative hydrogen production in continuous systems. International Journal of Hydrogen Energy, 41(6), 3820-3836) with higher production cost.

Dark fermentation of organic wastes for commercialization at large scale requires new routes for decreasing the cost of $H_2$ production. In presence of additional acetate, Clostridium strains utilized twice the amount of glycerol with 9% increase in $H_2$ production in comparison to without acetate (Heyndrickx et al. The fermentation of glycerol by Clostridium butyricum LMG 1212t2 and 1213t1 and C. pasteurianum LMG 3285. Appl. Microbiol. Biotechnol. 1991, 34 (5), 637-642). Repeated batch culture with polypeptone resulted in increase in $H_2$ yield from 2 to 2.4 mol/mol of glucose (Yokoi et al. Microbial hydrogen production from sweet potato starch residue. J. Biosci. Bioeng. 2001, 91 (1), 58-63). The expensive polypeptone was replaced with corn steep liquor; an nitrogen-rich organic waste resulted with increase in $H_2$ yield from 2.4 to 2.7 mol/mol of glucose (Yokoi et al. Microbial production of hydrogen from starch-manufacturing wastes. Biomass Bioenergy 2002, 22 (5), 389-395). Likewise, two industrial wastes, CG and apple pomace co-fermented resulting in 2.83 fold increase in $H_2$ production (Pachapur et al. Biohydrogen production by co-fermentation of crude glycerol and apple pomace hydrolysate using co-culture of Enterobacter aerogenes and Clostridium butyricum. Bioresour. Technol. 2015, 193, 297-306). Fruit and vegetable waste was mixed with swine manure; an alkali-rich material resulted in process stability and eliminated exogenous adjustments of pH for $H_2$ production (Tenca et al. Biohydrogen from thermophilic co-fermentation of swine manure with fruit and vegetable waste: Maximizing stable production without pH control. Bioresour. Technol. 2011, 102 (18), 8582-8588). Furthermore, the immobilization technique of using porous glass bead (Yokoi et al. $H_2$ production from starch by a mixed culture of Clostridium butyricum and Enterobacter aerogenes. Biotechnol. Lett 1998, 20 (2), 143-147), found an alternative in using dried lignocellulosic materials (such as coconut coir) resulting in 6.4-fold improvement in $H_2$ production (Patel et al. Dark fermentative hydrogen production by defined mixed microbial cultures immobilized on lignocellulosic waste materials. Int. J. Hydrogen Energy 2010, 35 (19), 10674-10681; and Patel et al. Enhancement in hydrogen production by co-cultures of Bacillus and Enterobacter. Int. J. Hydrogen Energy 2014, 39 (27), 14663-14668). The replacement of costly media components, utilization of industrial wastes and use of low-cost immobilizing material resulted in increased substrate availability for effective and economical $H_2$ production.

In 2015, Canada produced around 610 million dozen eggs and with the growth in demand, the production is anticipated to increase 4% per year (2015 Egg Farmers of Canada Annual report 2015). Food processing and manufacturing plants worldwide generate eggshells (10% of total mass) as solid waste, which is commonly disposed in landfills without any pretreatment.

The accumulation of organic acids or solvents results in sharp drop in fermentation pH and limit hydrogen production during dark fermentation. The spent media containing organic compounds and unutilized substrate with media components is of great interest as promising choice for waste utilization (Sargsyan et al. (2016). Novel approach of ethanol waste utilization: Biohydrogen production by mixed cultures of dark- and photo-fermentative bacteria using distillers grains. International Journal of Hydrogen Energy). Researchers have carried out combined dark and photo-fermentation for complete utilization of chemical energy in spent media by using unconverted metabolites to resolve the problem of waste utilization (Nath et al. (2005). "Hydrogen production by Rhodobacter sphaeroides strain OU 001 using spent media of Enterobacter cloacae strain DM11." Applied microbiology and biotechnology 68(4): 533-541). Sustainable utilization of active biomass and spent media resulted in improved hydrogen production (Sarma et al.

(2013). Hydrogen production from meat processing and restaurant waste derived crude glycerol by anaerobic fermentation and utilization of the spent broth. J. Chem. Technol. Biotechnol. doi: 10.1002/jctb.4099) and also resulted in fast mass scale one-pot green synthesis of nanoparticles (Morsy et al. CO 2-free biohydrogen production by mixed dark and photofermentation bacteria from sorghum starch using a modified simple purification and collection system. Energy 2015, 87, 594-604). The ethanol and beer producing industry's spent waste is valorized into lactic acid production by utilizing the free nitrogen content in wastes and eliminating the necessary addition of nitrogen supplement (Djukić-Vuković et al. (2016). "Wastes from bioethanol and beer productions as substrates for I (+) lactic acid production—A comparative study." Waste Management 48: 478-482). Production of ethanol can also be carried out by using a simple step of acid pretreatment on waste algal biomass resulting in almost 2-fold better yield in comparison to control experiment using glucose (Fathima et al. (2016). "Direct utilization of waste water algal biomass for ethanol production by cellulolytic *Clostridium phytofermentans* DSM1183." Bioresource technology 202: 253-256).

The hydrogen production process is only able to utilize 30-40% of substrate with remaining 60-70% used across metabolite production. In case of bioconversion of crude glycerol to 1 kg of hydrogen generates 8700 L of spent media consisting of organic carbon, total nitrogen, biomass along with metabolite and media composition (Sarma et al. (2015). "Hydrogen biorefinery: Potential utilization of the liquid waste from fermentative hydrogen production." Renewable and Sustainable Energy Reviews 50: 942-951). In order to match the production level and market value of biohydrogen with other commercial fuels, it is mandatory to valorize the spent media. Thus, spent media utilization will minimize the additional media components usage and the distilled water used across for the next batch of hydrogen production.

Therefore, the spent media after the co-culture system of hydrogen production may be reused as media supplement during mixed-culture of hydrogen production. The mixed-culture system may be carried out for the first time during hydrogen production with biodiesel sludge as inoculum along with spent media and crude glycerol as substrate. In another approach the fresh media may be replaced with spent media and used across algal growth for lipid production. In the interest of algae as generation feedstock for the biodiesel production and to minimize the cost of TAP (Tris-Acetate-Phosphate) growth media, spent media may be used for *Chlamydomonas reinhardtii* growth during lipid production. The approach may be to utilize the spend media generated during hydrogen production in an efficient closed system approach to uplift the commercialization of hydrogen and biodiesel fuels.

SUMMARY

According to an embodiment, there is provided a process for production of hydrogen gas ($H_2$) from fermentation of crude glycerol with a hydrogen producing microorganism in a bioreactor, comprising the step of:
  in a fermentation mixture comprising
    a fermentation medium which comprises a first volume of the crude glycerol and a hydrogen producing microorganism, under a fermentative hydrogen production condition,
  introducing a second volume of the crude glycerol, and
    removing a volume of the fermentation mixture equal to the second volume of the crude glycerol, to maintain constant the total volume of the fermentation mixture.

The process may be a continuous process or a semi-continuous process.

The fermentation medium may comprise an initial crude glycerol concentration from 2.5 to 20 g/L. The fermentation medium may comprise an initial crude glycerol concentration of about 10 g/L.

The second volume of crude glycerol may be at a concentration from 60 g/L to 120 g/L.

The second volume of the crude glycerol may be introduced at a constant feed rate.

The process may further comprise collecting the hydrogen gas ($H_2$) from the bioreactor.

The collecting may be continuous collecting or discontinuous collecting.

The discontinuous collecting may be by bubbling a gas in the fermentation mixture to release dissolved hydrogen gas therefrom.

The fermentative hydrogen production condition comprises a pH of 6.

The fermentation medium may be a supplemented fermentation medium, a mixed fermentation medium or a combination of supplemented fermentation medium, and mixed fermentation medium.

The crude glycerol may be untreated crude glycerol.

The supplemented fermentation medium may be supplemented with water, a salt, a nutrient, a pH control agent, a spent fermentation medium, a surfactant, an immobilization support, or combinations thereof.

The pH control agent comprises NaOH, KOH, calcium carbonate ($CaCO_3$), or combinations thereof.

The calcium carbonate may be from a natural source of calcium carbonate.

The natural source of calcium carbonate may be from an eggshell, a seashell, a cuttlefish bone, limestone, chalk, marble and calcite.

The natural source of calcium carbonate may be an eggshell.

The salt may comprise $KH_2PO_4$, $MgSO_4.7H_2O$, $Na_2HPO_4$ or combinations thereof.

The nutrient may be a yeast extract, a peptone, urea, slaughterhouse liquid waste, brewery waste biomass or combinations thereof.

The spent fermentation medium may be a medium from a previous hydrogen producing fermentation reaction.

The mixed fermentation medium may be crude glycerol mixed with a fermentable industrial by-product.

The fermentable industrial by-product may be an apple pomace, a brewery residue, a fruit waste, a vegetable waste, a swine manure, and combinations thereof.

The hydrogen producing microorganism may comprise a co-culture of hydrogen producing microorganism or a mixed culture of hydrogen producing microorganism.

The hydrogen producing microorganism comprises *Enterobacter aerogenes* (*E. aerogenes*), *Clostridium butyricum* (*C. butyricum*), *Chlamydomonas reinhardtii*, and combinations thereof.

The hydrogen producing microorganism comprises a co-culture of *E. aerogenes* and *C. butyricum*.

The surfactant may be polysorbate 80 (Tween® 80).

The polysorbate 80 may be at concentration of 10 mg/L to about 25 mg/L.

The polysorbate 80 may be at concentration of 10 mg/L.

The immobilization support may be a plastic microsphere, a plastic particle, a silica microsphere, a silica particle, an eggshell particle, a seashell particle, a cuttlefish bone particle, and combinations thereof.

The plastic microsphere or the silica microsphere may be a porous microsphere.

The plastic microsphere or the silica microsphere may be a hollow microsphere.

The eggshell particle may be of a size from 33 µm to 75 µm.

The eggshell particle may be at a concentration of from 0.25% to 4% (w/v).

The eggshell particle may be at a concentration of 0.25% (w/v).

The process may be monitored with sensor means.

The following terms are defined below.

The term "crude glycerol" or "CG" is intended to mean the major by-product of the transesterification process of lipid used for biodiesel production. In general, for every 100 Kg of biodiesel produced, approximately 10 Kg of crude glycerol are created. The composition of crude glycerol is heterogeneous, as it may contain many other compounds such as monoglyceride, diglyceride, methanol, soap, and catalysts used for transesterification (see below). In embodiments, the crude glycerol may be untreated crude glycerol.

The terms "eggshell" or "EGS" are intended to mean the outer covering of a hard-shelled egg and of some forms of eggs with soft outer coats. For example, bird eggshells contain calcium carbonate and dissolve in various acids, including the vinegar used in cooking. Eggshells are mostly 94-97% calcium carbonate crystals, stabilized by a protein matrix. Without the protein, the crystal structure would be too brittle to keep its form and the organic matrix is thought to have a role in deposition of calcium during the mineralization process. The structure and composition of the avian eggshell serves to protect the egg against damage and microbial contamination, prevention of desiccation, regulation of gas and water exchange for the growing embryo, and provides calcium for embryogenesis. Eggshell formation requires gram amounts of calcium being deposited within hours, which must be supplied via the female bird diet.

The term "bioreactor" is intended to mean an apparatus in which a biological reaction or process is carried out. This includes small, medium and large (industrial) scale apparatuses.

The term "fermentation medium" is intended to mean a growth medium in which fermentation by suitable microorganism such as bacteria and fungi to make useful products can take place. In some embodiments, the fermentation medium may be supplemented with several different kinds of additives (see below).

The term "fermentation mixture" is intended to mean a combination of the fermentation medium and the microorganisms.

The term "hydrogen producing microorganism" is intended to mean a microorganism that are capable of producing hydrogen gas ($H_2$), and include for example *Enterobacter aerogenes, Clostridium butyricum* (*C. butyricum*) and the algae *Chlamydomonas reinhardtii*.

The term "fermentative hydrogen production condition" is intended to mean fermentation conditions that are suitable for the production of hydrogen gas ($H_2$) by the selected hydrogen producing microorganism. Such conditions include for example the appropriate temperature, pH, nutrient and salt condition, agitation as well as any other suitable and/or necessary condition required to achieve hydrogen production under fermentative conditions.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 2:
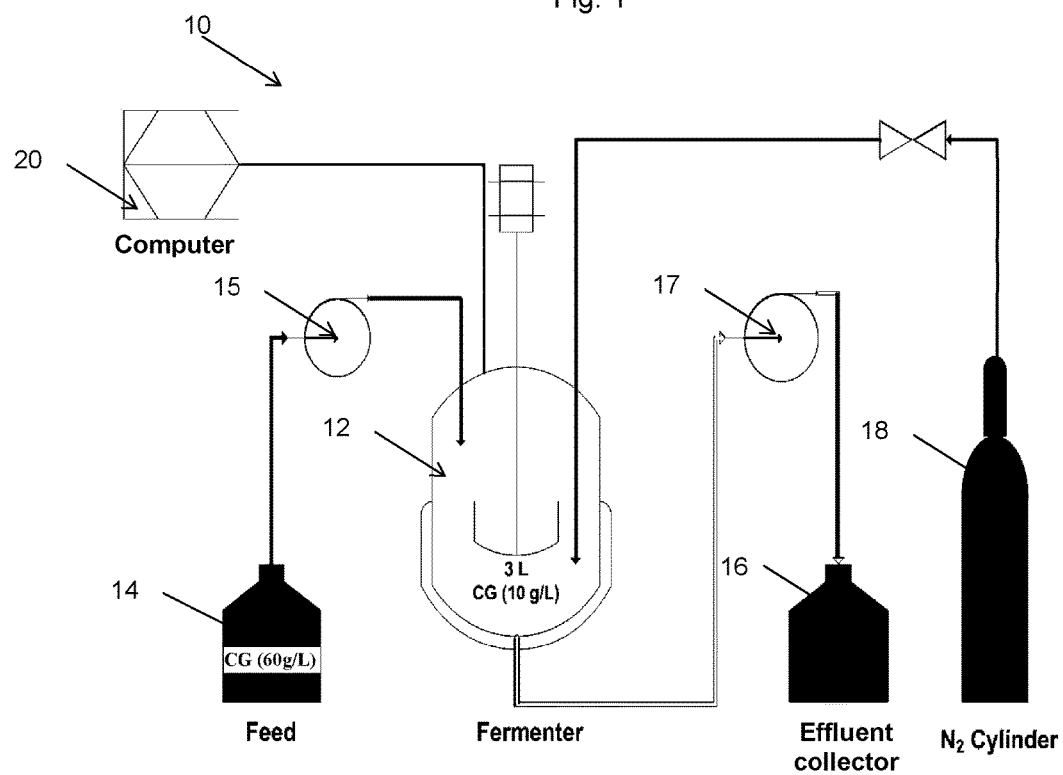
FIG. 2 illustrates schematic representation of the process according to one embodiment of the present invention.

Now referring to FIG. 2, in embodiments there is disclosed a process 10 for production of hydrogen gas ($H_2$) from fermentation of crude glycerol with a hydrogen producing microorganism in a bioreactor 12. The process comprises the step of introducing a volume of the crude glycerol (a second volume, from a feed source 14, connected to pump 15, for example) in a fermentation mixture which comprises a fermentation medium comprised of a first volume of crude glycerol and a hydrogen producing microorganism under a fermentative hydrogen production condition. While this second volume of crude glycerol is introduced, a volume of the fermentation mixture under fermentation equal to the second volume of crude glycerol is removed from the fermentation mixture to maintain constant the total volume of fermentation mixture. The withdrawn volume of the fermentation mixture under fermentation may be collected in effluent collector 16, connected to pump 17, for example.

According to an embodiment, the process may be a continuous process, where the second volume of crude glycerol is continuously introduced at a constant feed rate, while the volume of fermentation mixture which is removed is removed at the same feed rate. The rate of introduction of crude glycerol and that of withdrawal of the fermentation mixture under fermentation is established such that the hydrogen production conditions are optimal for both hydrogen production and crude glycerol utilization. According to another embodiment, the process may be a semi-continuous process, where the second volume of crude glycerol is introduced at a predetermined time interval, while the volume of fermentation mixture which is removed is removed at the same time as the introduction of the first volume. The interval of introduction of crude glycerol and that of withdrawal of the fermentation mixture under fermentation is established such that the hydrogen production conditions are optimal for both hydrogen production and crude glycerol utilization.

Composition of the Fermentation Medium

According to an embodiment, the fermentation medium may comprise an initial crude glycerol concentration from about 2.5 to about 20 g/L, or from about 5 to about 20 g/L, or about 10 to about 20 g/L, or about 15 to about 20 g/L, or about 2.5 to about 15 g/L, or from about 5 to about 15 g/L, or about 10 to about 15 g/L, about 2.5 to about 10 g/L, or from about 5 to about 10 g/L, about 2.5 to about 5 g/L, or from about 2.5, 5, 10, 15, 20 g/L, or preferably about 10 g/L.

According to an embodiment, the second volume of crude glycerol may be at a concentration from about 60 g/L to about 120 g/L, or from about 70 to about 120 g/L, or from about 80 to about 120 g/L, or from about 90 to about 120 g/L, or from about 100 to about 120 g/L, or from about 110 to about 120 g/L, or 60 g/L to about 110 g/L, or from about 70 to about 110 g/L, or from about 80 to about 110 g/L, or from about 90 to about 110 g/L, or from about 100 to about 110 g/L, or 60 g/L to about 100 g/L, or from about 70 to about 100 g/L, or from about 80 to about 100 g/L, or from about 90 to about 100 g/L, or 60 g/L to about 100 g/L, or from about 70 to about 100 g/L, or from about 80 to about 100 g/L, or from about 90 to about 100 g/L, or 60 g/L to about 90 g/L, or from about 70 to about 90 g/L, or from about 80 to about 90 g/L, or 60 g/L to about 80 g/L, or from about 70 to about 80 g/L, or 60 g/L to about 70 g/L, or about 60, 70, 80, 90, 100, 110, 120 g/L or preferably 60 g/l, or preferably 120 g/L.

According to another embodiment, the fermentation medium may be an untreated crude glycerol, a supplemented fermentation medium, and a mixed fermentation medium, or a combination of supplemented fermentation medium, and mixed fermentation medium. In embodiments, the supplemented fermentation medium may be supplemented with water; a salt, such as $KH_2PO_4$, $MgSO_4.7H_2O$, $Na_2HPO_4$ or combinations thereof; a nutrient, such as a yeast extract, a peptone, urea, slaughterhouse liquid waste (SL), brewery waste biomass (BWB) or combinations thereof; a pH control agent, such as NaOH, KOH, calcium carbonate ($CaCO_3$), or combinations thereof; a spent fermentation medium, such as a medium from a previous hydrogen producing fermentation reaction; a surfactant, an immobilization support or combinations of each thereof.

According to an embodiment, the fermentative hydrogen production condition comprises a pH of 6, or from about 5 to about 7, or from about 5.5 to about 7, or from about 6 to 7, or about 6.5 to 7, or about 5 to about 6.5, or from about 5.5 to about 6.5, or from about 6 to 6.5, or about 5 to about 6.0, or from about 5.5 to about 6.0, or about 5 to about 5.5. The added cost of media components, external buffering agents and material cost for immobilization can be eliminated by using a cost-effective and environmental approach of recycling eggshells during $H_2$ production. Therefore, sustainable development of solid waste recycling by using CG and eggshell as media replacement may result in cost-effective $H_2$ production. The calcium carbonate used as a pH control agent may therefore be chosen from a natural source of calcium carbonate, such as an eggshell, a seashell, a cuttlefish bone, limestone, chalk, marble and calcite. Preferably, the natural source of calcium carbonate is an eggshell, or fragments thereof.

In embodiments, the mixed fermentation medium may be crude glycerol mixed with a fermentable industrial by-product. For example, the fermentable industrial by-product may be an apple pomace, a brewery residue, a fruit waste, a vegetable waste, a swine manure, and combinations thereof.

In another embodiment, the fermentation medium of the present invention may also be supplemented with a surfactant. Surfactants have been used in fermentation to assist growth, entry of substrate into cells, increase performance during fermentation, and increase solubility/yield of substrate, among other things. According to an embodiment, the surfactant may be polysorbate 80 (Tween® 80). The polysorbate 80 may be used at concentration of about 10 mg/L to about 25 mg/L, or from about 15 to about 25 mg/L, or from about 20 to about 25 mg/L, or from about 10 mg/L to about 20 mg/L, or from about 15 to about 20 mg/L, or from about 10 mg/L to about 15 mg/L, or about 10, 15, 20, 25 mg/L, or preferably at concentration of 10 mg/L.

In embodiments, the immobilization support may be chosen from plastic microspheres, plastic particles, silica microspheres, silica particles, eggshell particles, seashell particles, cuttlefish bone particles, and combinations thereof. In some embodiments, the plastic microsphere or the silica microsphere may be porous microspheres and/or hollow microspheres, to substantially increase surface area of the immobilization support.

In another embodiment, the eggshell particle may be of a size from about 30 to about 75 μm, or from about 33 μm to about 75 μm, or from about 35 μm to about 75 μm, or from about 40 μm to about 75 μm, or from about 45 μm to about 75 μm, or from about 50 μm to about 75 μm, or from about 55 μm to about 75 μm, or from about 60 μm to about 75 μm, or from about 65 μm to about 75 μm, or from about 70 μm to about 75 μm, or 30 to about 70 μm, or from about 33 μm to about 70 μm, or from about 35 μm to about 70 μm, or from about 40 μm to about 70 μm, or from about 45 μm to about 70 μm, or from about 50 μm to about 70 μm, or from about 55 μm to about 70 μm, or from about 60 μm to about 70 μm, or from about 65 μm to about 70 μm, or 30 to about 65 μm, or from about 33 μm to about 65 μm, or from about 35 μm to about 65 μm, or from about 40 μm to about 65 μm, or from about 45 μm to about 65 μm, or from about 50 μm to about 65 μm, or from about 55 μm to about 65 μm, or from about 60 μm to about 65 μm, or 30 to about 60 μm, or from about 33 μm to about 60 μm, or from about 35 μm to about 60 μm, or from about 40 μm to about 60 μm, or from about 45 μm to about 60 μm, or from about 50 μm to about 60 μm, or from about 55 μm to about 60 μm, or 30 to about 55 μm, or from about 33 μm to about 55 μm, or from about 35 μm to about 55 μm, or from about 40 μm to about 55 μm, or from about 45 μm to about 55 μm, or from about 50 μm to about 55 μm, or 30 to about 50 μm, or from about 33 μm to about 50 μm, or from about 35 μm to about 50 μm, or from about 40 μm to about 50 μm, or from about 45 μm to about 50 μm, or 30 to about 45 μm, or from about 33 μm to about 45 μm, or from about 35 μm to about 45 μm, or from about 40 μm to about 45 μm, or 30 to about 40 μm, or from about 33 μm to about 40 μm, or from about 35 μm to about 40 μm, or 30 to about 35 μm, or from about 33 μm to about 35 μm, or 30 to about 33 μm.

According to another embodiment, the eggshell particle may be at a concentration of from about 0.25% to about 4% (w/v), or from about 0.25% to about 3% (w/v), or from about 0.25% to about 2% (w/v), or from about 0.25% to about 2% (w/v), or from about 0.25% to about 1% (w/v), or from about 0.25% to about 0.5% (w/v), or from about 0.5% to about 4% (w/v), or from about 0.5% to about 3% (w/v), or from about 0.5% to about 2% (w/v), or from about 0.5% to about 2% (w/v), or from about 0.5% to about 1% (w/v), or from about 1% to about 4% (w/v), or from about 1% to about 3% (w/v), or from about 1% to about 2% (w/v), or from about 1% to about 2% (w/v), or from about 2% to about 4% (w/v), or from about 2% to about 3% (w/v), or from about 3% to about 4% (w/v), or from about 0.25, 0.5, 1, 2, 3, 4% (w/v), and preferably 0.25% (w/v).

Hydrogen Producing Microorganisms

In embodiments, the process of the present invention relies on hydrogen producing microorganisms for the production of $H_2$ gas. In embodiments, the hydrogen producing microorganisms may be from a single strain (source) of hydrogen producing microorganism. According to another embodiment, the hydrogen producing microorganism may be a co-culture of hydrogen producing microorganisms, as such co-culture have been shown to increase hydrogen production over single cultures. In embodiments, the hydrogen producing microorganism comprises *Enterobacter aerogenes* (*E. aerogenes*), *Clostridium butyricum* (*C. butyricum*), *Chlamydomonas reinhardtii*, and combinations thereof. According to a preferred embodiment, the hydrogen producing microorganism comprises a co-culture of *E. aerogenes* and *C. butyricum*. According to another embodiment, the treatment of wastewater generates primary sludge (settling solid), which may be used as seed inoculum to carry out mixed-culture system of hydrogen production. The primary sludge was stored at 4° C., prior to pretreatment to carry out hydrogen production using crude glycerol at higher concentration. In similar ways wastewater sludge collected from Quebec Urban Community (QUC) wastewater treatment plant (WWTP) (Quebec, QC, Canada) was analyzed as possible seed inoculum along with primary sludge from biodiesel industry (see below).

Monitoring and Collection of Produced Hydrogen Gas ($H_2$)

According to another embodiment, the process may further comprise the step of collecting the hydrogen gas ($H_2$) from the bioreactor. In embodiments, collecting may be continuous collecting, wherein the gas produced is simultaneously recovered with known means, or may be discontinuously collected, by leaving the gas accumulate in the head space of the bioreactor and medium, and an inert gas such as nitrogen (e.g. from an attendant nitrogen source 17) may be bubbled and sparged through the medium to release and collect the produced $H_2$ gas.

In another embodiment, the process of the present invention may be monitored with sensor means, for example hydrogen sensors, pH sensors, and the likes, that are operatively connected to appropriate computing means, such as computer 20.

The present invention will be more readily understood by referring to the following examples which are given to illustrate the invention rather than to limit its scope.

Example 1

Semi-Continuous Bioprocess for Hydrogen Production from Crude Glycerol 1.1 Microorganism and Culture Conditions A facultative anaerobic bacterium, *Enterobacter aerogenes* NRRL B-407, was selected for the present study. This known hydrogen producer is a gram-negative rod-shaped bacterium, which was provided by ARS (USDA, USA). For regular propagation of the microorganism a synthetic culture medium composed of glucose (5 g/L), casein peptone (5 g/L), $KH_2PO_4$ (2 g/L), $MgSO_4 \cdot 7H_2O$ (0.5 g/L) and yeast extract (0.5 g/L), has been used. The same culture medium has also been used for inoculum preparation for the present study. For both purposes, the microorganism was anaerobically grown in 50 mL of aforementioned medium taken in 125 mL serum bottles. Prior to inoculation, the bottles were sterilized and cooled to room temperature. After inoculation, the bottles were incubated by using an orbital shaker incubator operated at 30±1° C. and 150 rpm. About 5% (v/v) of freshly grown microbial culture obtained by this method was used as the inoculum for all hydrogen production studies conducted during this investigation.

1.2 Crude Glycerol as Feedstock

As already mentioned, CG, a by-product of biodiesel manufacturing process has been used as the feedstock for this investigation. The CG has been supplied by Rothsay biodiesel, Canada. Considering the fact that CG is an industrial waste of very crude nature and a good source of nutrient for microbial growth as well; it is highly possible that it contains different microorganisms. Thus, to have an idea about the activity of its indigenous microbial community, crude glycerol was analyzed to detect potential metabolites of microbial origin. For this purpose, a solution of 12 g/L of CG was prepared with distilled water and centrifuged at 10,000 rpm (6708×g) for 10 minutes. The supernatant was directly analyzed by gas chromatography following the method described in analysis section.

1.3 Hydrogen Production Using a 7.5 L Bioreactor

A 7.5 L bioreactor (Labfors, Infors-HT, Switzerland) with maximum working volume of 5 L has been used for the present hydrogen production study. Purpose of this study was to develop a low cost bioprocess for hydrogen production by replacing expensive synthetic fermentation media components; therefore, the media were prepared using only CG and water. The first batch of experiment was performed with a medium volume of 3 L and the initial CG concentration was 10 g/L, whereas, the feeding CG concentration was 60 g/L. The pH was adjusted with HCl and NaOH. The fermenter vessels containing medium, feeding bottle with CG solution and acid and base containing bottles were autoclaved for 20 minutes at 121±1° C. Throughout the fermentation period, agitation of the process was kept constant at 100 rpm. All openings of the bioreactor vessel were sealed and the medium was inoculated by transferring the inoculum from serum bottle by using a peristaltic pump fitted with sterile silicone tube.

During the fermentation period, the bioreactor was connected to a laptop where real time values of all process parameters were recorded by using Iris software (Infors-HT, Switzerland). For first 8 hours, the reactor was operated in batch mode. From 8 to 48 hours, CG solution taken in feeding bottle was drop wise added to main fermentation medium and equal amount of fermented medium was taken out by using a peristaltic pump, so that the medium volume of the bioreactor remains constant at 3 L. Another purpose of withdrawing the fermented medium from the reactor was to remove a portion of the organic acids accumulated during the process, so that decrease in medium pH could be minimized. The reactor was constantly monitored and once the hydrogen concentration in the headspace reached around 30-35% (v/v), the medium was bubbled with nitrogen gas to drive away accumulated biogas.

Same procedure was followed for the second batch of experiment with two major exceptions. Firstly, the load of CG used as feed was twice to that of the first batch. Secondly, drop wise addition of the feed was started at 8 hours and it lasted until 72 hours, in contrast to 48 hours in the first case. The reason behind sustained delivery of feed was to avoid probable substrate inhibition due to sharp increase in glycerol concentration in the medium.

1.4 Analysis 1.4.1 Hydrogen Analysis

A hydrogen sensor was used for online monitoring of hydrogen production in the bioreactor. The sensor used for the present investigation was supplied by BlueSens gas sensor GmbH (Germany). It was installed outside the bioreactor and its inlet was connected to the exhaust gas condenser by using a short tube. Before starting the fermentation, the sensor was connected to power supply for one hour. Following this heating-up time, nitrogen gas was bubbled through the medium for 30 minutes and exhaust gas ($N_2$) was allowed to pass through the sensor inlet. During fermentation, the outlet of the sensor was closed by multiple layers of paraffin films. After inoculation the sensor started displaying signal in the monitor and it was recorded online.

Crude glycerol contains glycerol and other things such as free fatty acids and soap. While using crude glycerol as the feedstock, often hydrogen produced from the compounds other than glycerol was not considered in most of the hydrogen yield calculations available in the literature. Therefore, to avoid any mistake in the calculation, in the present example instead of hydrogen yield (mmol-$H_2$ produced/mol glycerol), hydrogen production has been reported as mmol-$H_2$/L medium or L-$H_2$/L medium.

1.4.2 Analysis of Different Fermentation End Products

Aqueous samples collected at the end of each batch of fermentation were analyzed by GC to determine the amount of different by-products produced during the process. The samples were centrifuged for 10 minutes at 10,000 rpm (6708 g) and the supernatants were directly analyzed by GC (GC7890B, Agilent Technologies, USA). The detector used for this purpose was flame ionization detector (FID). The column temperature gradient used for this analysis was 50-250° C. It was achieved by increasing the temperature at a rate of 20° C. per minute. Nitrogen was used as carrier gas. The injection volume was 0.8 µl and iso-butanol was mixed with all samples as internal standard.

1.4.3 Glycerol Analysis

At the end of each batch of fermentation (120 h), liquid samples were collected from the reactor as well as from the effluent collecting bottles and analyzed for residual glycerol concentration. A method originally proposed by Bondioli et al (2005). An alternative spectrophotometric method for the determination of free glycerol in biodiesel. European journal of lipid science and technology, 107(3), 153-157, has been used for this analysis, which had been also used in Sarma et al. Investigation of the effect of different crude glycerol components on hydrogen production by *Enterobacter aerogenes* NRRL B-407. Renewable Energy, 2013, 60, 566-571. Briefly, 1 mL of the sample already diluted with distilled water was mixed with 1 mL of working solution (ethanol, 47.5% v/v). Subsequently, 1.2 mL of 'stock solution A' (0.2 M acetylacetone solution prepared using a mixture of equal volume of 1.6 M acetic acid and 4.0 M ammonium acetate) and 1.2 mL of 'stock solution B' (10 mM sodium periodate solution prepared using a mixture of equal volume of 1.6 M acetic acid and 4.0 M ammonium acetate) were added. Further, the test tube containing the final solution was heated at 70±1° C. for 1 min by using a rotary shaker water bath and subsequently transferred to a cold water container maintained at 20±1° C., until analyzed. The optical density of the reaction mixture was measured at 410 nm by a UV-Vis spectrophotometer (Carry 100 Bio®, Varian USA).

1.5 Results and Discussion 1.5.1 Crude Glycerol Characterization

Figure 1:
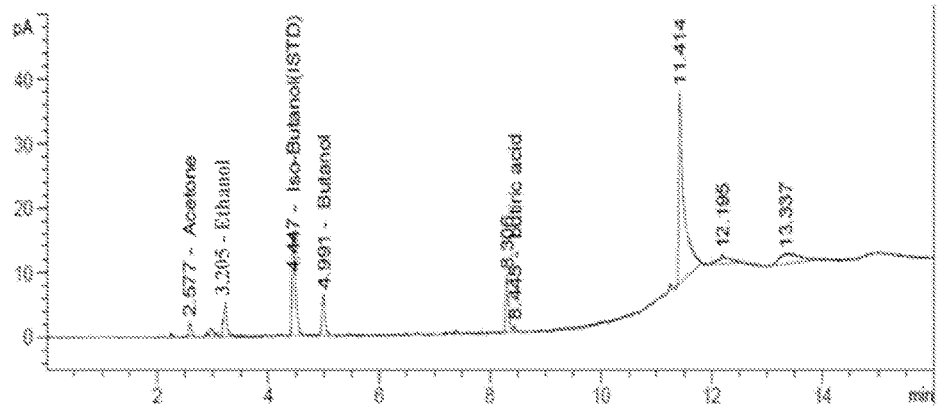
FIG. 1 illustrates a gas chromatogram of CG showing the presence of acetone, butanol, ethanol and butyric acid as well as different unidentified compounds.

The CG used in the present study has been characterized and glycerol content and pH were found to be 23.63±2.5% (w/w) and 3.4 (at 24±0.5° C.), respectively. Likewise, elemental analysis has shown that it contains nearly 35.9±0.4% (w/w) of total organic carbon and 3.25±0.1% (w/w) of nitrogen. On a similar note, soap, methanol, mono-glyceride, di-glyceride, fatty acid methyl esters, and free fatty acids in CG are present. As a part of present investigation, microbial metabolites' presence in CG has been studied. A gas chromatogram of the CG used in the present example has been presented in FIG. 1. From this chromatogram, it is evident that acetone (1.34 g/kg), butanol (3.38 g/kg), ethanol (4.47 g/kg) and butyric acid were present in CG. This observation indicated that while storing, indigenous microorganism of CG can carry out anaerobic acetone-butanol-ethanol type fermentation; however, presence of these metabolites does not give any direct information about the exact species of the microorganisms present in CG. Anaerobic acetone-butanol-ethanol type fermentation is highly possible because CG is very viscous in nature and hence limited oxygen mass transfer may occur while storing. Thus, local anaerobic/anoxic condition may prevail, once the dissolved oxygen of CG is consumed by indigenous aerobes/facultative anaerobes. As shown in FIG. 1, apart from the compounds identified by the gas chromatographic analysis, there are certain other compounds which could not be identified.

1.5.2 Hydrogen Production Using a 7.5 L Bioreactor

Effect of different initial CG concentrations, ranging from 2.5-20 g/L, on biohydrogen production had been investigated using small scale batch processes. The outcome of the study had suggested that 10 g/L CG was optimum for batch fermentation. Moreover, at relatively high initial CG concentration of 20 g/L, almost 40% of glycerol was found to remain unutilized. On the contrary, for large-scale production of biohydrogen, a process with high substrate concentration will be more appropriate as, from stoichiometric point of view; such process will be able to produce more amount of hydrogen per liter of medium. Thus, using same reactor volume, same operating cost and at the expense of almost same amount of energy; more amount of hydrogen could be produced by such process. However, substrate inhibition is probably a limitation of fermentative hydrogen production (Roy et al. Continuous thermophilic biohydrogen production in packed bed reactor. Applied Energy, 2014, 136, 51-58) and as mentioned earlier, when initial CG concentration was increased beyond 10 g/L, almost no improvement in hydrogen production was observed.

Figure 3:
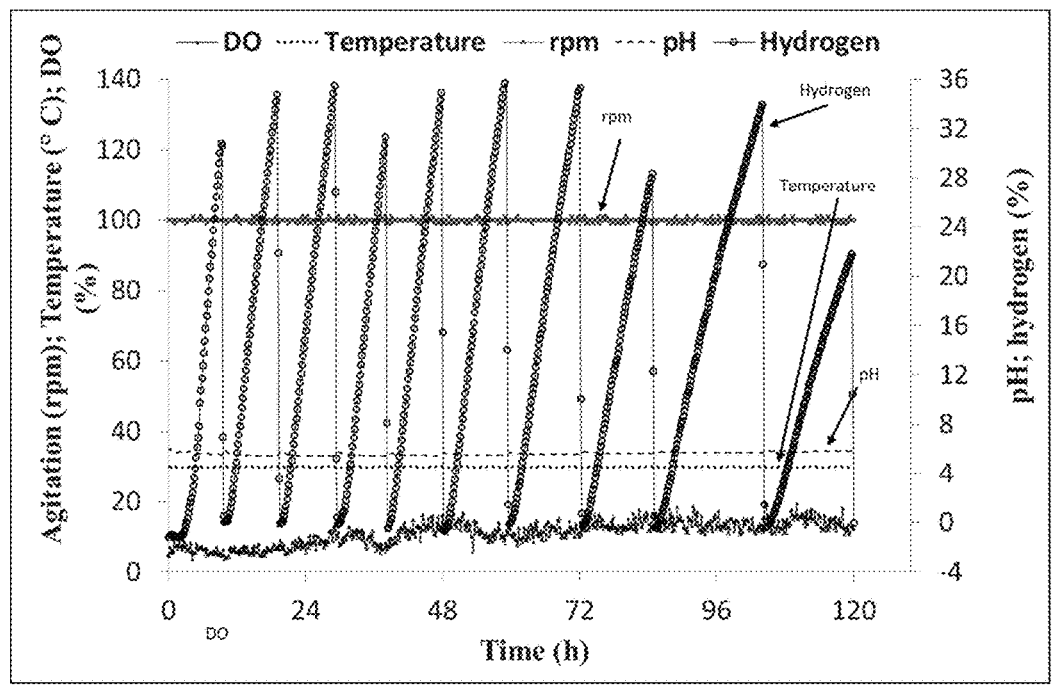
FIG. 3 illustrates online data collected from a first batch of fermentation carried out using a feed CG concentration of 60 g/L. Hydrogen accumulated in the headspace of the reactor was periodically removed by bubbling with nitrogen gas.

In order to overcome the substrate inhibition, therefore, as a part of the present example, a semi continuous process has been tested. Two batches of fermentation have been carried out to evaluate the effect of two different feed concentrations, i.e. 60 g/L and 120 g/L of CG. For the first set of experiment involving 60 g/L of CG as feed; for initial 8 hours, the fermentation was carried out in batch mode with an initial CG concentration of 10 g/L. After utilization of a portion of the feedstock, from 8 to 48 hours, by using a peristaltic pump the CG solution containing 60 g/L of CG was drop wise added into the fermenter. To keep the medium volume constant, equal volume of fermented medium was simultaneously taken out of the reactor (FIG. 2). The result of this experiment has been presented in FIG. 3. As it is evident from FIG. 3, with a negligible lag period of around 2-3 hours, rate of hydrogen production was almost constant until 48 hours of fermentation. A gradual decrease in hydrogen production rate has been observed after this period; although the production was not stopped even at the end of the experiment. After 48 hours the microbial cells may enter stationary and declining phase of growth, therefore, gradual decrease in hydrogen production observed after this period can be attributed to such phase change. Based on the data recorded online, cumulative hydrogen production has been calculated to be 14.41 L, which corresponded to 4.80 L hydrogen/L medium. At atmospheric pressure and 30° C., this value is equivalent to 190 mmol-$H_2$/L medium. For this calculation, fermented medium taken out of the reactor and the amount of hydrogen accumulated in the headspace of bottle that had been used to collect that liquid, have not been considered.

Compared to a traditional batch process, a process of this kind may be able to utilize double amount of CG without doubling the medium volume, and inoculum requirement of the process. Additionally, as only 500 mL of fermented medium was taken out of the reactor, loss of active biomass should not be as high as a continuous process with short hydraulic retention time. Moreover, the chance of substrate inhibition was lesser, as the process was started at an optimum initial CG concentration (10 g/L) and additional amount of CG was fed to the process over a period of 40 hours, so that the microorganism gets sufficient time to consume a significant amount of the feedstock. The feeding rate was arbitrarily chosen for this investigation.

Interestingly, corresponding to increase in initial CG concentration of a batch process from 2.5 g/L to 20 g/L, gradual decrease in final media pH had been observed. It was observed that in all cases, within the first 24 h, the media pH dropped to below 4. Further, there was a correlation between the media pH at the end of the process and the initial CG concentrations. In the case of 20 g/L CG, the final pH of the broth was as low as 3.65; at 2.5 g/L CG, the pH was 4.06. This may be due to the fact that at 20 g/L CG, the substrate was available to the microorganism until the end of fermentation and the amount of different organic acids produced was greater than that of 2.5 g/L CG. Therefore, sharp decrease in media pH could be one of the reasons of reduced hydrogen production at high initial substrate concentration. Thus, this observation suggested the fact that by controlling the process pH, higher hydrogen yield could be possible even at relatively high initial CG concentration, such as 20 g/L. Based on this observation; optimum pH for hydrogen production (pH 6) was maintained throughout the fermentation by using NaOH solution.

The fermentation medium was periodically bubbled with nitrogen gas to remove accumulated hydrogen. Hydrogen partial pressure buildup in the headspace can adversely affect the product yield. Nitrogen sparging can increase hydrogen production by removing the gas accumulated in the headspace of the reactor. For industrial scale production of biohydrogen, periodic nitrogen sparging approach may not be suitable. In such cases, instead of nitrogen sparging, simultaneous production and recovery of hydrogen could be a viable option for enhanced hydrogen yield.

Application of expensive media components reduces the economic feasibility of fermentative hydrogen production. Likewise, substrate pretreatment is an additional step for hydrogen production using certain substrates, such as lignocellulosic materials. Therefore, in order to develop a low cost process, untreated CG has been evaluated as the only medium component for hydrogen production. The outcome of the example has suggested that the present approach can offer a low cost as well as high yield process for fermentative hydrogen production.

Figure 4:
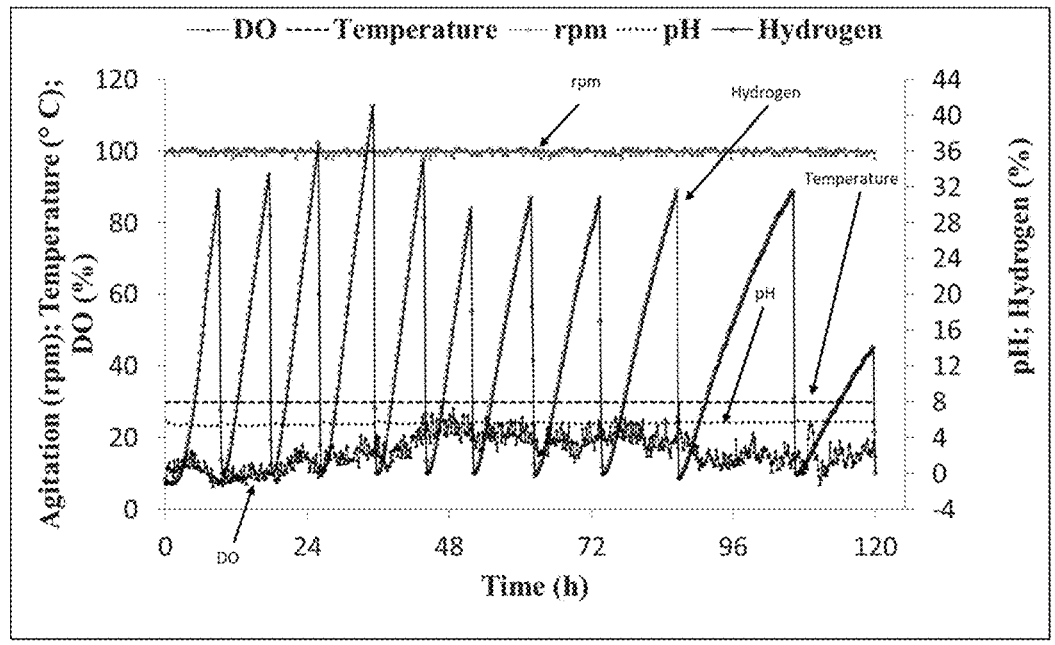
FIG. 4 illustrates online data collected from the second batch of fermentation carried out using a feed CG concentration of 120 g/L. Hydrogen accumulated in the headspace of the reactor was periodically removed by bubbling with nitrogen gas.

Hydrogen production profile of the second batch of fermentation carried out using the feed containing 120 g/L of CG, has been presented in FIG. 4. Cumulative hydrogen production was 15.55 L; which corresponded to 5.18 L-$H_2$/L-medium. Compared to reported 2.02 and 2.68 L-$H_2$/L-medium, hydrogen production achieved in the present investigation is significantly higher than all the previous reports (Table 2) involving CG. This value is equivalent to 210 mmol-$H_2$/L-medium, which is slightly higher than 190 mmol-$H_2$/L-medium obtained for the first batch of fermentation carried out using 60 g/L of CG as feed.

In order to have an idea about substrate utilization, residual glycerol concentrations were determined for each batch of fermentation and the results have been summarized in Table 1. From Table 1, it is evident that in the case of first batch of fermentation using 60 g/L CG as feed; almost 91% of glycerol added to the process has been utilized. On the contrary, corresponding to an increase in feed CG concentration to 120 g/L, glycerol utilization has been reduced to 65%. These observations underline the fact that hydrogen production could be slightly enhanced by increasing the feed CG concentration; however, a considerable amount of glycerol was left unutilized by the approach. As shown in Table 1, $H_2$ yield for the first batch was 4.06 mol/mol-glycerol consumed, whereas for the second batch it was 4.19 mol/mol-glycerol consumed. However, as mentioned above, in addition to glycerol, some other compounds present in crude glycerol such as soap, free fatty acid etc. could also be simultaneously consumed by the microorganism and they might contribute in final hydrogen yield. Therefore, actual hydrogen production from each mol of glycerol will be slightly lower than these values.

Figure 5:
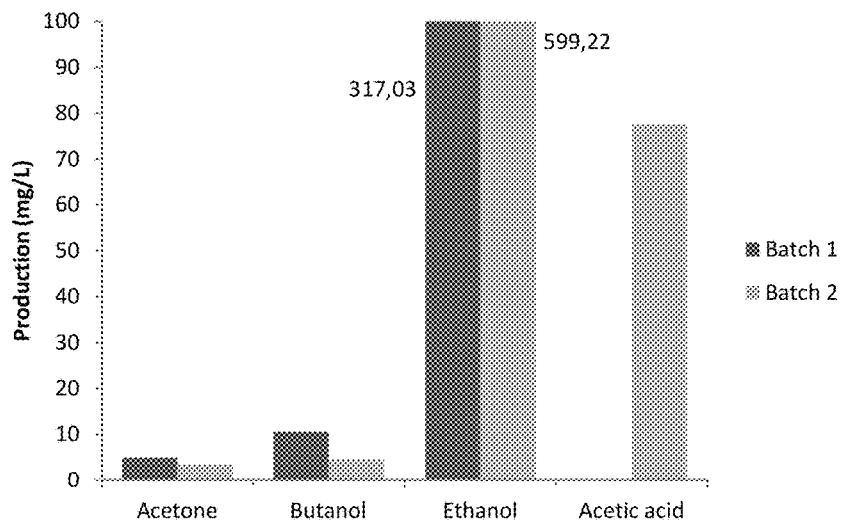
FIG. 5 illustrates different byproducts accumulated in the media after 120 hours of fermentation. Ethanol has been identified as the major by-product of hydrogen production by CG bioconversion.

During hydrogen production by microbial fermentation different metabolites are accumulated in the medium as byproducts. Amount of such byproducts produced during the two batches of fermentation has been presented in FIG. 5. From FIG. 5 it is evident that in the case of first batch among acetone (4.9 mg/L), butanol (10.61 mg/L), ethanol (317.03 mg/L), ethanol was the dominant byproduct. In the case of second batch apart from acetone (3.43 mg/L) and butanol (4.61 mg/L), comparatively higher amount ethanol (599.22 mg/L) as well as acetic acid (77.56 mg/L) was produced.

Substrate concentration is a parameter to determine the amount and type of byproducts produced during fermentative hydrogen production because it may alter the redox balance of the medium. Therefore, observed differences in byproduct profiles of the two batches of fermentation can be attributed to different feed CG concentrations (60 g/L and 120 g/L) used in this investigation.

TABLE 1

Summary of Example 1

| | | |
|---|---|---|
| CG concentration in feed (g/L) | 60 | 120 |
| Amount of glycerol added to the process (g) | 14.17 | 21.26 |
| Amount of unused glycerol (g) | 1.24 | 7.44 |
| Glycerol utilization (%) | 91 | 65 |
| Cumulative hydrogen production (L) | 14.41 | 15.55 |
| Hydrogen production per liter medium (mmol) | 190 | 210 |
| Mol-$H_2$ produced per mol-glycerol consumed | 4.06* | 4.19* |

*$H_2$ produced from glycerol and other compounds present in crude glycerol

TABLE 2

Summary of different studies on hydrogen production by CG bioconversion

| SL. No. | Fermentation type | Initial substrate concentration | Microorganism | Supplement | $H_2$ production (reported) | $H_2$ production (L/L-medium)* | Ref. |
|---|---|---|---|---|---|---|---|
| 1 | Photo-fermentation | CG containing 0.92 g/L (10 mM) glycerol | Rhodopseudomonas palustris | RCV medium, biotin, para-aminobenzoic acid, glutamate | 6 mol/mol glycerol | 1.49 L-$H_2$/L-medium (60 mmol-$H_2$/L-medium)*** | Sabourin-Provost et al. Hallenbeck, Bioresource technology, 2009, 100, 3513-3517 |
| 2 | Dark fermentation | CG containing 10 g/L glycerol | Enterobacter aerogenes HU-101 | Complex medium, phosphate buffer | 63 mmol-$H_2$/L-medium/h | 1.6 L-$H_2$/L-medium | Ito et al. Journal of bioscience and bioengineering, 2005, 100, 260-265. |
| 3 | | CG containing 10 g/L glycerol | Enterobacter aerogenes ATCC 13048 | Complex medium with buffering agents | 2.5 L-$H_2$/L-medium | 2.5 L-$H_2$/L-medium | Marques et al. Proceeding Hypothesis VIII, Lisbon, 2009 |
| 4 | | 5 g/L pretreated CG | Thermotoga neapolitana DSM 4359 | 2 g/L yeast extract, 0.05M HEPES buffer; cysteine hydrochloride | 2.73 ± 0.14 mol-$H_2$/mol-glycerol consumed | 2.20 L-$H_2$/L-medium (77.14 mmol-$H_2$/L-medium) | Ngo et al. International Journal of Hydrogen Energy, 2011, 36, 5836-5842 |
| 5 | | CG containing 9.9 g/L glycerol | Enterobacter aerogenes NBRC 12010 | NBRC 702 medium, thionine | 0.77 mol-$H_2$/mol-glycerol consumed | 2.06 L-$H_2$/L-medium (83.16 mmol-$H_2$/L-medium) | Sakai et al. Biotechnology and bioengineering, 2007, 98, 340-348 |
| 6 | | 3 g/L CG | Mixed culture | 70 mM MES buffer, nutrient solution | 0.31 mol-$H_2$/mol-glycerol | 0.28 L-$H_2$/L-medium | Selembo et al. Biotechnology and bioengineering, 2009, 104, 1098-1106 |
| 7 | | 10 g/L CG | Enterobacter aerogenes NRRL B-407 | No supplement (low cost process) | 84.08 mmol-$H_2$/L | 2.02 L-$H_2$/L-medium | Sarma et al. « Journal of Chemical Technology and Biotechnology, 2013, 88, 2264-2271 |
| 8 | | 20 g/L CG** | Enterobacter aerogenes NRRL B-407 | No supplement (low cost process) | 190 mmol-$H_2$/L medium | 4.80 L-$H_2$/L-medium | Present example |
| 9 | | 30 g/L CG** | Enterobacter aerogenes NRRL B-407 | No supplement (low cost process) | 210 mmol-$H_2$/L medium | 5.18 L-$H_2$/L-medium | Present example |

*Calculated from literature data;
**total amount of CG per liter medium;
***considering complete conversion of added glycerol

1.6 Cost Benefits Analysis

In Table 3, the items required for and the cost involved in hydrogen production from 1 kg of crude glycerol by using the semi-continuous process considered in this example has been listed. For a detailed methodology of cost calculation, Sarma et al (2013) can be consulted (Sarma et al. Bio-hydrogen production by biodiesel-derived crude glycerol bioconversion: a techno-economic evaluation. Bioprocess and biosystems engineering, 2013, 36, 1-10). Based on this estimation, total cost involved in bioconversion of 1 kg of CG was found to be $5.9. Notably, out of this amount, $4.61 is for the synthetic medium components required for inoculum development. Interestingly, we have found that a mixture of 5 g/L crude glycerol and 8% (v/v) brewery waste hydrolysate can be used for inoculum development with no compromise in hydrogen production. Thus, inoculum development will be possible without these expensive chemicals and the cost involved in the process will be negligible. Hence, cost involved in hydrogen production can be calculated to be around $1.29/kg CG. It implies that production of 1 cubic meter of hydrogen will cost around $5.39. This amount is approximately 53 times lower than a traditional process for CG bioconversion. Current market value of industrial grade hydrogen is about $7.75 to $11.50/cubic meter. Therefore, as an industrial gas, commercial production of biohydrogen seems to be an achievable target. Moreover, the wastewater of hydrogen production process can be directly used for methane generation, ethanol recovery or as phosphate solubilizer (Liu et al. (2006). Hydrogen and methane production from household solid waste in the two-stage fermentation process. Water Research, 40(11), 2230-2236; and Sarma et al. <<Liquid waste from bio-hydrogen production—A commercially attractive alternative for phosphate solubilizing bio-fertilizer", International Journal of Hydrogen Energy, 2013, 38, 8704-8707.). Recovery of another biofuel (ethanol) from this wastewater may contribute in overall energy gain of the process (Chu et al. Direct fermentation of sweet potato to produce maximal hydrogen and ethanol. Applied Energy, 2012, 100, 10-18). Further, these potential byproducts may be helpful in further reduction of the process cost by generating additional revenue. For the present analysis, the amount of nitrogen used for flushing out the hydrogen accumulated in the headspace of the reactor was not considered. In industrial scale, instead of using nitrogen, continuous removal of accumulated gas by pump and simultaneous purification by pressure swing adsorption technology could be considered. Likewise, the infrastructure required for the entire production and purification process will also have a contribution in final production cost. It was observed that fermentation medium cost can be as high as 82% of total cost of hydrogen production from crude glycerol (Sarma et al. Bio-hydrogen production by biodiesel-derived crude glycerol bioconversion: a techno-economic evaluation. Bioprocess and biosystems engineering, 2013, 36, 1-10). Therefore, as shown in Table 3, the cost of only medium ingredients and some other major cost contributors were considered for the present estimation. Thus, actual production cost will be slightly different from the value obtained in this estimation.

TABLE 3

Cost analysis of the semi-continuous process considered in the present example

| SL No. | Process | Item required | Amount | Cost ($) |
|---|---|---|---|---|
| 1 | Inoculum development (2.5 L) | Glucose monohydrate (5 g/L) | 12.5 g | 0.57 |
| | | Casein peptone (5 g/L) | 12.5 g | 2.81 |
| | | Yeast extract (0.5 g/L) | 1.25 g | 0.15 |
| | | $KH_2PO_4$ (2 g/L) | 5 g | 1.01 |
| | | $MgSO_4 \cdot 7H_2O$ (0.5 g/L) | 1.25 g | 0.05 |
| | | Sterilization and incubation (17 h) | Electricity 0.085 kWh | 0.0005 |
| 2 | Media preparation (47.5 L) | $H_2O$ + CG | 1 kg (CG) | 0.1 |
| 3 | Anaerobic dark fermentation | Sterilization and incubation (120 h) | Electricity 12 kWh | 0.53 |
| 4 | pH control | NaOH | 90 g | 0.65 |
| | Total cost of bioconversion of 1 kg CG | | | 5.90 |
| | Cumulative $H_2$ production from 1 kg of CG | | | 240 L |

1.7 Conclusions

Acetone, butanol and ethanol have been detected in CG used as the feedstock for present hydrogen production example. The finding indicates that due to cumulative activity of indigenous microorganisms while storing, acetone-butanol-ethanol (ABE) fermentation occurs in CG. Present investigation has demonstrated that by diluting with distilled water, CG can be used as the only medium component to design a low-cost process for enhanced hydrogen production. As high as 5.18 L-$H_2$/L-medium, which is equivalent to 210 mmol-$H_2$/L-medium; has been produced by the approach outlined in the present report. This amount is significantly higher than 2.02 to 2.68 L-$H_2$/L-medium known for hydrogen production by CG bioconversion. Ethanol was the major byproduct of the hydrogen production process. By reducing the feed CG concentration from 120 g/L to 60 g/L, glycerol utilization could be improved from 65% to 91%. Overall, it has been concluded that a process where CG is diluted with only water to reduce the process cost, substrate inhibition is minimized by operating the process at optimum CG concentration which is followed by drop wise addition of feed to ensure maximum CG utilization per liter working volume of the fermenter per unit of time, inhibition of hydrogen production by increased hydrogen partial pressure buildup in the headspace of the fermenter is reduced by removing the accumulated gas, pH of the process is precisely controlled by a low cost option such as addition of NaOH, and biomass loss is minimized by optimizing the hydraulic retention time can result in higher and more economical hydrogen production compared to the process where only one or a few of these factors are controlled at a time.

Example 2

Surfactant Mediated Enhanced Glycerol Uptake and Hydrogen Production from Biodiesel Waste Using Co-Culture of *Enterobacter Aerogenes* and *Clostridium Butyricum*

2.1. Microorganisms, Pre-Culture Media and Inoculum Development

*E. aerogenes* (NRRL B-407) and *C. butyricum* (NRRL B-41122) were procured from ARS, USDA, USA. Basal synthetic medium consisting of glucose (10 g/L), casein polypeptone (20 g/L), $KH_2PO_4$ (2 g/L), yeast extract (0.5 g/L) and $MgSO_4 \cdot 7H_2O$ (0.5 g/L) was used for pre-anaerobic culturing *E. aerogenes* at 30° C. Modified basal medium supplemented with L-cysteine-HCl.H$_2$O (1 g/L) as a reducing agent was used for pre-culturing *C. butyricum* anaerobically at 36° C. Different media components were mixed in distilled water to make-up the volume to 47.5 mL. The initial pH was adjusted to 6.5 by using NaOH and 47.5 mL final medium was transferred into serum bottles (125 mL). Medium was sparged with pure $N_2$ gas for 5 min and later sealed using aluminum crimp seals with pre-inserted septa to create anaerobic conditions. The serum bottles containing medium was sterilized using autoclave (Tuttnauer 3870-Heidolph) at 121° C., for 20 min. About 5% (v/v) inoculum at log phase was transferred using sterile syringe and culture incubation was carried out at 150 rpm in an orbital incubator shaker (INFORS HT—multitron standard). According to previous studies, the co-culture system resulted in increased hydrogen production in comparison to mono-culture (Pachapur et al. Biohydrogen production by co-fermentation of crude glycerol and apple pomace hydrolysate using co-culture of *Enterobacter aerogenes* and *Clostridium butyricum*, Bioresource Technology, 193 (2015) 297-306; and Pachapur et al. Evidence of metabolic shift on hydrogen, ethanol and 1, 3-propanediol production from crude glycerol by nitrogen sparging under micro-aerobic conditions using co-culture of *Enterobacter aerogenes* and *Clostridium butyricum*, International Journal of Hydrogen Energy, 40 (2015) 8669-8676). Hence, all experiments were carried out using co-culture system in triplicates and the presented values are the averages of triplicates with standard deviation (±) values as error bars.

2.2. Source of Substrate, Chemicals and Reagents

Crude glycerol was supplied by Rothsaye, Canada which comprises restaurant and meat processing industry containing cooking oil and animal fats for biodiesel production. The crude glycerol composition contained (w/w): glycerol (23.6%), carbon (35.9%), nitrogen (3.2%), ash (3.06%), and moisture content (5.75%) with 67.56% of matter organic non-glycerol (MONG). The crude glycerol pH was around 3.4±0.07 and with methanol recovery carried out by Rothsay Inc. led to methanol fraction of around <1-0.5%.

2.3. Effect of Surfactant on Hydrogen Production

The present invention also considers the use of surfactant at very low concentration for bioconversion of crude glycerol into hydrogen production using co-culture system of *Enterobacter aerogenes* (*E. aerogenes*) and *Clostridium butyricum* (*C. butyricum*).

Surfactants, such as Tween 80 have been used in fermentation to assist growth, entry of substrate into cells (Reese et al. Surfactants as stimulants of enzyme production by microorganisms, Applied Microbiology, 17 (1969) 242-245), increase performance during fermentation (Lee et al. Effect of surfactants on ethanol fermentation using glucose and cellulosic hydrolyzates, Biotechnology Letters, 18 (1996) 299-304) [26] with highest bacterial growth (Goes et al. Effect of surfactants on α-amylase production in a solid substrate fermentation process, Journal of Chemical Technology and Biotechnology, 74 (1999) 709-712) during enzymes, degrade high molecular weight hydrocarbons (Boonchan et al. Surfactant-enhanced biodegradation of high molecular weight polycyclic aromatic hydrocarbons by *Stenotrophomonas maltophilia*, Biotechnology and Bioengineering, 59 (1998) 482-494), increase solubility/yield of substrate (Sarkar et al. Bioethanol production from agricultural wastes: An overview, Renewable Energy, 37 (2012) 19-27) and ethanol production. To the best of inventor's knowledge, the effect of surfactant on hydrogen production using crude glycerol has not been studied so far. Hence, Tween 80 at varying concentrations (10, 20, 50, 100 and 1000 mg/L) in presence of media (1% crude glycerol+media components), along with positive control (1% crude glycerol+media components) without Tween 80 and negative control (1 Tween+media components) without crude glycerol was tested. In the example, 1% crude glycerol resulting in increased hydrogen production across co-culture system in comparison to mono-culture system, to study the effect of surfactant on hydrogen production, 1% of crude glycerol was fixed with varying concentrations of Tween 80.

2.4. Optimization of Hydrogen Production Using Response Surface Methodology

In order to optimize Tween 80 and crude glycerol concentrations for maximum hydrogen production, response surface methodology (RSM) has been used. Central Composite Design (CCD) was used to design the experiments where hydrogen production was investigated as a function of crude glycerol (substrate) and Tween 80 concentration. As shown in Example 1 above, Crude glycerol at 10 g/L had been found to be optimum for hydrogen production. Thus, 10 g/L of crude glycerol has been considered as low value with 25 g/L as high value for the present experimental design. Similarly, Tween 80 at 5 mg/L and 25 mg/L were considered as low and high actual value, respectively. The CCD ranges of the two input factors considered for the example are presented in Table 4.

TABLE 4

Central composite design ranges of the two input factors considered for the hydrogen production

| Factor | Name | Units | Low Actual | Mean | High Actual |
|---|---|---|---|---|---|
| A | Crude glycerol | g/L | 10 | 17.5 | 25 |
| B | Tween | mg/L | 5 | 15 | 25 |

Experimental design was developed using Design-Expert®-7 software (Stat-Ease Inc. Minneapolis, Minn.) and resulted in 13 experimental runs. Depending upon each run requirement, exact concentration of crude glycerol and Tween 80 was mixed in distilled water to make-up working volume (47.5 mL) along with media components (casein polypeptone, $KH_2PO_4$, $MgSO_4.7H_2O$ and yeast extract). After mixing, pH of the final volume for each run was adjusted to 6.5, later steps similar to inoculum development at 36° C. and 150 rpm were followed. During the fermentation, gas were collected every 24 h and liquid samples at the end was analyzed, as described in analytical technique section.

The relationship between the factors considered in this example, i.e., crude glycerol (g/L) and Tween 80 (mg/L) and the response variables: $H_2$ production (mmol/L), glycerol utilization (%) and viscosity (cP) of the fermentation media was determined by design matrix evaluation. The response surface for significant interactions in terms of quality of model fit, model term coefficient within p value 0.05), adjusted $R^2$ values, final equation and statistical significance was verified for the analysis of variance (ANOVA).

2.5. Validation Experiments Using CCD Optimized Values

Different concentrations of crude glycerol and Tween 80 were used to generate an optimum value for hydrogen production using CCD. Validation of the optimized conditions (crude glycerol: 17.5 g/L and Tween 80: 15 mg/L) was tested for the mono-culture studies in presence of *E. aerogenes* and *C. butyricum* only. The optimized condition in absence of Tween 80 was also tested. The effect of yeast extract and peptone as carbon source for hydrogen production was determined using optimized conditions in the absence of crude glycerol. In order to determine the effect of crude glycerol pretreatment on hydrogen production, the optimized conditions in presence of pretreated crude glycerol was carried out. The crude glycerol was mixed with distilled water to reduce the fluid viscosity and then pH-adjusted to 3 with hydrochloric acid, the free fatty acids that precipitated from the liquid were separated by centrifugation at 5000 rpm.

2.6. Analytical Methods

2.6.1. Hydrogen Analysis by GC-TCD

The gas sample collected manually using gas tight syringe (5 mL, SGE Analytical Science, Australia) in sample vials. The hydrogen analysis was carried out using gas chromatography (Varian 3800, USA) setup. A PoraPLOT Q® column (Agilent technology, USA) fitted with thermal conductivity detector (TCD) equipped within carrier gas was nitrogen at a flow rate of 3.5 mL/min with column and detector working temperature fixed at 100° C. $H_2$ retention time was around 4.5 min and volume of gas produced was converted to mmol/L.

2.6.2. By-Products Analysis by GC-FID

The liquid sample for determination of glycerol utilization and by-products (ethanol, butyric acid and 1,3-propanediol) were analyzed using ZB-WAX plus column (30 m×0.25 mm, 0.25 μm film thickness) fitted with flame ionization detector (FID) within gas chromatography (GC) (7890B GC-Agilent, Santa Clara, Calif.) setup. The carrier gas, helium at a flow rate of 1 mL/min with a 80° C. to 240° C. temperature profile under 8.4 min method run time was developed for the analysis.

2.6.3. Analysis of Media Viscosity

Viscosity measurement of the fermentation media, before and after addition of Tween 80 was performed using a rotational viscometer (Fungilab™, Premium Series, USA) setup. The L1 spindle was cleaned using dust-free Kim wipes, sample cup containing 25 mL of fermentation media at constant shear rate (305.7 per sec) with 2 min analysis time.

2.7. Results and Discussion

2.7.1 Effect of Surfactant on Hydrogen Production

Figure 6:
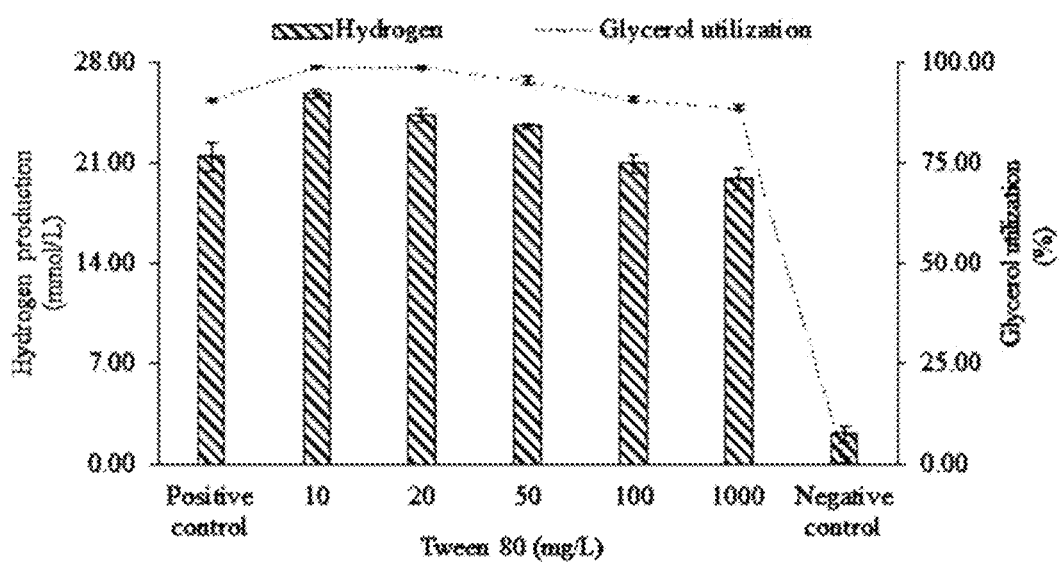
FIG. 6 illustrates hydrogen production along with glycerol utilization (%) in the presence of varying concentrations of Tween 80 (1% crude glycerol+media components), positive control (1 crude glycerol+media components) with no Tween 80 and in presence of negative control (1% Tween+media components) with no crude glycerol was tested.

The effect of surfactant on hydrogen production, using different Tween 80 concentrations (10, 20, 50, 100 and 1000 mg/L) at fixed crude glycerol concentration of (10 g/L) along with positive and negative control is presented in FIG. 6. In positive control, the hydrogen production was around 21.4±0.99 mmol/L of medium, highest production among other Tween 80 concentrations. With further increase in concentration of Tween 80, the hydrogen production started decreasing from 25.7±0.34 to 19.8±0.78 mmol/L and in case of negative control; the hydrogen production was the least with 2.1±0.55 mmol/L as seen from the FIG. 6. The least production of hydrogen was in presence of only Tween 80 (negative control) suggested that the co-culture system depended on crude glycerol as substrate source for hydrogen production. The glycerol utilization among different concentrations of Tween 80 was within close range of (99.85±0.12 to 88.59±0.45) for positive control (90.47±0.33%) and for negative control was below detection level. In this set of experiments, hydrogen production was the main parameter in pre-selecting the concentration of Tween 80 (10-20 mg/L) for further optimization along with media viscosity measurement. Presence of Tween 80 (10 mg/L) resulted in 20.20% increase in hydrogen production in comparison to 21.4±0.99 mmol/L obtained for the positive control. The crude glycerol concentration of 10 g/L for co-culture system in presence of minimum concentration of Tween 80 (10 mg/L) resulted in increased hydrogen production. Hence, the effect of Tween 80 at higher concentration of crude glycerol was investigated using CCD. The effect of Tween 80 across 10 and 20 mg/L resulted in similar glycerol utilization values ranging from 99.85±0.12% to 98.69±0.48%. Thus, crude glycerol concentration (10 to 25 g/L) and Tween 80 concentration (5 to 25 mg/L) were varied across the CCD model.

2.7.2. Optimization of Hydrogen Production Using RSM

The experimental design involving different concentrations of crude glycerol and Tween 80, along with the results obtained for hydrogen, glycerol utilization and viscosity for each experimental run has been presented in Table 5. The hydrogen production ranged from about 23.7±1.58 mmol/L (run: 4, CG: 17.5 and Tween 80: 29.14) to a maximum of 32.1±0.03 mmol/L (run: 11, CG: 17.5 and Tween 80: 15).

TABLE 5

Experimental design matrix defining concentration of crude glycerol and Tween 80 with the response on $H_2$ production, residual glycerol, viscosity and by-products concentration for each run.

| Run | A: Crude glycerol g/L | B: Tween mg/L | Hydrogen mmol/L | Glycerol utilization % | Viscosity (cP) | 1-3PD g/L | Butyric acid g/L | Ethanol g/L |
|---|---|---|---|---|---|---|---|---|
| 1 | 28.11 | 15 | 25.5 ± 0.63 | 60.7 ± 0.66 | 2.33 ± 0.04 | 5.15 ± 0.48 | 1.79 ± 0.35 | 4.67 ± 0.74 |
| 2 | 17.5 | 15 | 30.7 ± 0.14 | 84.7 ± 0.25 | 2.27 ± 0.04 | 3.64 ± 0.86 | 3.96 ± 0.48 | 2.54 ± 0.51 |
| 3 | 17.5 | 15 | 30.7 ± 0.09 | 87.4 ± 0.60 | 2.28 ± 0.03 | 3.23 ± 0.34 | 3.63 ± 0.47 | 2.87 ± 0.96 |
| 4 | 17.5 | 29.14 | 23.7 ± 1.58 | 82.5 ± 0.25 | 2.25 ± 0.04 | 3.82 ± 0.44 | 1.65 ± 0.91 | 2.49 ± 0.43 |
| 5 | 10 | 5 | 29.6 ± 1.14 | 99.8 ± 0.34 | 2.30 ± 0.02 | 3.98 ± 0.70 | 3.64 ± 0.50 | 2.14 ± 0.89 |
| 6 | 25 | 5 | 29.1 ± 1.93 | 58.0 ± 0.71 | 2.32 ± 0.02 | 5.65 ± 0.53 | 2.99 ± 0.78 | 4.15 ± 0.45 |
| 7 | 17.5 | 0.86 | 29.8 ± 0.05 | 79.4 ± 0.91 | 2.30 ± 0.03 | 4.15 ± 0.94 | 3.01 ± 0.38 | 2.11 ± 0.81 |
| 8 | 17.5 | 15 | 31.7 ± 0.02 | 87.8 ± 0.54 | 2.28 ± 0.03 | 3.71 ± 0.78 | 3.96 ± 0.86 | 2.78 ± 0.69 |
| 9 | 10 | 25 | 27.5 ± 1.38 | 99.8 ± 0.02 | 2.26 ± 0.06 | 2.58 ± 0.90 | 2.98 ± 0.40 | 1.88 ± 0.49 |
| 10 | 25 | 25 | 24.5 ± 1.43 | 72.2 ± 0.75 | 2.29 ± 0.06 | 5.85 ± 0.71 | 1.71 ± 0.21 | 4.04 ± 0.41 |
| 11 | 17.5 | 15 | 32.1 ± 0.03 | 87.7 ± 0.50 | 2.28 ± 0.03 | 3.75 ± 0.18 | 3.82 ± 0.61 | 2.91 ± 0.78 |
| 12 | 6.89 | 15 | 24.4 ± 0.83 | 99.5 ± 0.37 | 2.22 ± 0.02 | 2.71 ± 0.75 | 1.85 ± 0.45 | 1.69 ± 0.12 |
| 13 | 17.5 | 15 | 30.5 ± 1.23 | 87.0 ± 0.28 | 2.28 ± 0.03 | 3.78 ± 0.38 | 3.92 ± 0.57 | 2.83 ± 0.39 |

The model p-value of 0.0036 implied statistically significant relation. The final model equation (Eq. (1)) in terms of coded factors that best fitted the hydrogen production response is shown below:

$$\text{Hydrogen}=31.14-0.24\times CG-1.92\times \text{Tween}-0.63\times CG\times \text{Tween}-2.64\times CG\times CG-1.74\times \text{Tween}\times \text{Tween} \quad (1)$$

The coefficient of Tween 80 (1.92) as seen in [Eq. (1)] was much higher than the other ones, indicating that the studied range had a dominant effect on hydrogen production. Summarized ANOVA for the response surface quadratic model in case of $H_2$ production with p-value has been presented in Table 6. The p-value of 0.0047 indicated that the linear dependence of Tween 80 had a significant impact on $H_2$ production.

TABLE 6

Summarized ANOVA for the response surface quadratic model for $H_2$, residual glycerol and viscosity.

| | p-value | | |
|---|---|---|---|
| Source | $H_2$ | Glycerol utilization | Viscosity |
| Model | 0.0036 | <0.0001 | 0.0249 |
| A-Crude glycerol | 0.6208 | <0.0001 | 0.0040 |
| B-Tween | 0.0047 | 0.0473 | 0.0236 |
| AB | 0.3780 | 0.0357 | 0.7805 |
| $A^2$ | 0.0012 | 0.0256 | 0.6737 |
| $B^2$ | 0.0107 | 0.0465 | 0.6737 |
| $R^2$ | 0.80 | 0.95 | 0.79 |

Figure 7:
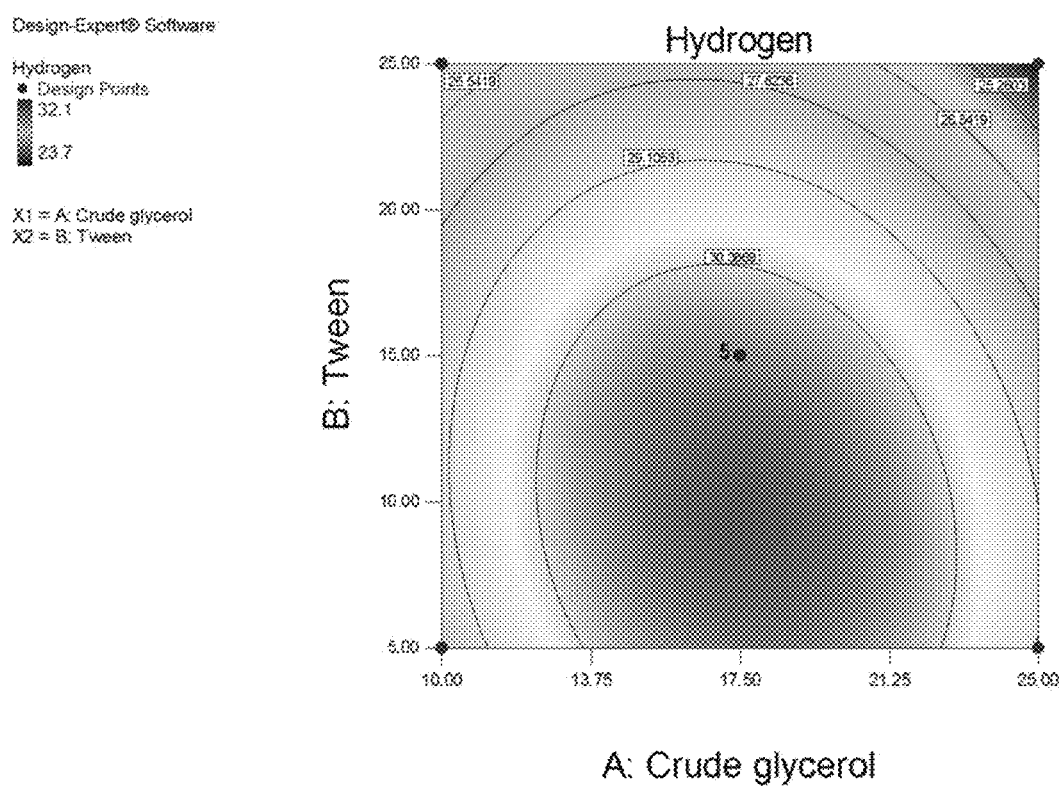
FIG. 7 illustrates the experimental responses of hydrogen production (mmol/L) with the fitting function of crude glycerol (g/L) and Tween concentration (mg/L) using response surface plots.

The experimental responses of hydrogen production are plotted with the fitting function of crude glycerol and Tween 80 concentration in FIG. 7. At minimum concentration of Tween 80 (5 mg/L) with increasing concentration of crude glycerol, the production of hydrogen increased. However, further increase in the concentration of Tween 80 (>15 mg/L) decreased the production of hydrogen as seen in FIG. 7.

Crude glycerol and Tween 80 have a parabolic relationship for hydrogen production. At maximum concentration of Tween 80 (29.14 mg/L) for the run 4 in presence of 17.5 g/L of crude glycerol resulted in minimum value of 23.7±1.58 mmol/L of hydrogen production. The optimum concentration of crude glycerol for the co-culture example in our earlier studies was around 10 g/L, further increase in crude glycerol concentration resulted in substrate inhibition causing a decrease in hydrogen production. In case of minimum concentration of Tween (0.86 mg/L) in presence of 17.5 g/L of crude glycerol, the hydrogen production further increased to 29.8±0.05 mmol/L. The results at two extreme ends of Tween 80 concentration suggested that the optimum condition of Tween 80 for increased hydrogen production was within 5 to 15 mg/L. This is seen in run 11 at crude glycerol concentration of 17.5 g/L with Tween 80 concentration of (15 mg/L) resulting in maximum $H_2$ production reaching 32.1±0.03 mmol/L. In case of run 7 and 13, the hydrogen production values were closer while considering standard deviation. However, in case of run 7, with lower amount of Tween 80 (0.86 mg/L) resulted in decreased glycerol utilization with 79.4±0.91% and increased production of 1,3-PD around 4.15±0.94 g/L in comparison to optimized conditions of run 7 with 87.7±0.50% utilization and 3.78±0.18 g/L production. The increased concentration of Tween 80 for run 13 resulted in increased rate of hydrocarbon degradation with increased hydrogen production, and in lower concentration of Tween 80 for run 7 resulted in substrate inhibitor with 1,3-PD production. The increased production of 1,3-PD results in decreased production of hydrogen, as reducing equivalents for hydrogen production are utilized during 1,3-PD production. On the contrary, with further increase in the concentration of crude glycerol to 28.11 g/L in presence of 15 mg/L of Tween 80, hydrogen production reached 25.5±0.63 mmol/L. Using crude glycerol at higher concentration in the fermentation media resulted in decreased hydrogen production and increased production of by-products such as 1,3-PD (5.15±0.48 g/L). The presence of Tween 80 in the fermentation media helped to increase the bioavailability of the substrate to the microorganisms, increase hydrocarbon degradation, increased growth, improved fermentation activity and increased substrate utilization rate. The effect of Tween 80 on hydrogen production is also well supported by the model p-value of 0.0047 as seen from Table 6.

The central design points of the model with optimum conditions of crude glycerol: 17.5 g/L and Tween 80: 15 mg/L resulted in increased hydrogen production reaching a maximum value of 32.1±0.03 mmol/L.

2.7.3. Effect of Tween 80 on Glycerol Utilization

The residual glycerol after fermentation was analyzed by GC-FID; later glycerol utilization in terms of percentage was calculated and used for ANOVA analysis. The quadratic model for glycerol utilization with p-value of <0.0001 was statistically significant with $R^2$ value of 0.95 as seen from Table 6. The final equation [Eq. (2)] that best fitted the response and to compare coefficient of parameters for glycerol utilization, is shown below:

$$\text{Glycerol utilization}=86.92-15.53\times CG+2.32\times \text{Tween}+3.55\times CG\times \text{Tween}-2.93\times CG\times CG-2.50\times \text{Tween}\times \text{Tween}$$

Figure 8:
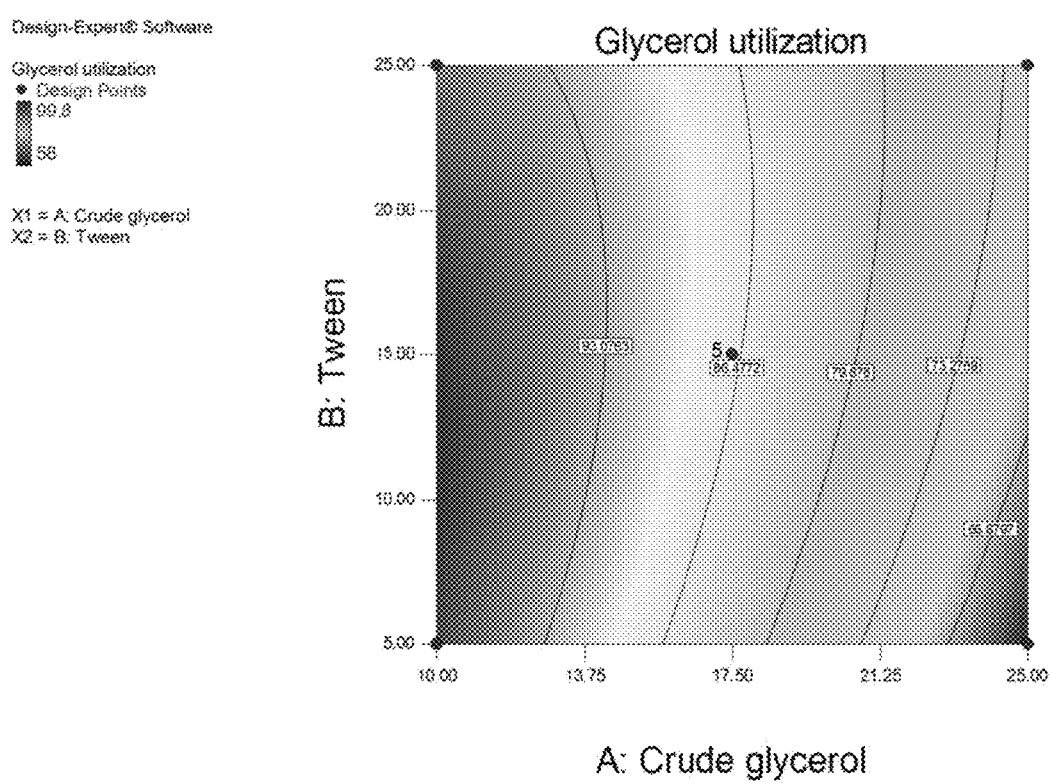
FIG. 8 illustrates the response of glycerol utilization (%) across the concentration of crude glycerol (g/L) and Tween 80 (mg/L) using response surface plots.

The coefficient of crude glycerol (15.53) was much higher, indicating that the linear dependence of crude glycerol had a significant impact on glycerol utilization as seen from Table 6. The response of glycerol utilization across the concentrations of crude glycerol and Tween 80 using response surface plot is presented in FIG. 8. The glycerol utilization ranged from about 58±0.71% (run: 6, CG: 25 g/L, Tween: 5 mg/L) to a maximum of 99.8±0.02% (run: 9, CG: 10, Tween: 25) as seen from Table 5. The increased production of hydrogen resulted in optimized conditions of 17.5 g/L crude glycerol and 15 mg/L of Tween with glycerol utilization of around ~90%. Increase in the concentration from the optimized conditions for crude glycerol resulted in decreased glycerol utilization. In case runs 1 and 2, 5 and 6, 12 and 13, with increasing concentration of crude glycerol from 15.5 to 28.11, 10 to 25, 6.89 to 17.5 g/L, there was decrease in glycerol utilization as seen from FIG. 8 and Table 5. Across the runs with crude glycerol as input parameter played a very important role in case of glycerol utilization and is well supported by model p-value of <0.0001 (A) and 0.0256 ($A^2$) as seen from Table 6.

At maximum concentration of Tween 80 (29.14 mg/L) in presence of 17.5 g/L of crude glycerol, around 82.5±0.25% of glycerol was utilized. However, at minimum concentration of Tween 80 (0.86 mg/L) at same concentration of crude glycerol (17.5 g/L), the glycerol consumption decreased to 79.4±0.91%. At maximum concentration of crude glycerol (28.11 g/L), in presence of 15 mg/L of Tween 80, the glycerol utilization reached lower value of 60.7±0.66% indicating substrate inhibition. This suggested higher amount of Tween 80 within 5-15 mg/L required for increased utilization of crude glycerol at 17.5 g/L. Thus, at 17.5 g/L of crude glycerol in presence of 15 mg/L of Tween 80 resulted around-87% utilization of crude glycerol with increased hydrogen production suggesting the optimum concentration of Tween 80. The main objective of the example was to produce increased hydrogen production at higher concentration of crude glycerol in presence of Tween 80. Thus, the optimized conditions for run 2, 3, 8, 11 and 13 of crude glycerol (17.5 g/L) and Tween 80 (15 mg/L) together improved the glycerol utilization, which resulted in increased hydrogen production.

Presence of Tween 80 in the fermentation media assisted microorganism growth, increased enzyme activity and improved microorganism-substrate interaction resulting in increased substrate utilization. The effect of surfactant might have played a role of buffering/acid neutralizing agent by eliminating pH drop and its presence had beneficial effect with 2.5-fold increase in glycerol utilization.

Compared to other approaches, such as immobilization, repeated batch fermentation and two-stage system to increase the substrate utilization for hydrogen production, using less-expensive mode of adding Tween 80 at minimum concentration resulted in increased hydrogen production along with increased substrate utilization rate.

2.7.4. Effect of Tween 80 on Media Viscosity

The media viscosity after addition of Tween 80 was used in the example. The model terms for viscosity with p-value of 0.0249 (<0.05) was found to be statistically significant. The final equation [Eq. (3)] that best fitted the response data and to compare coefficient of parameters for viscosity, is shown below:

$$\text{Viscosity} = 2.28 + 0.026 \times CG - 0.018 \times \text{Tween} + 2.500E-3 \times CG \times \text{Tween} + 2.875E-3 \times CG \times CG + 2.875E-3 \times \text{Tween} \times \text{Tween} \quad (3)$$

Figure 9:
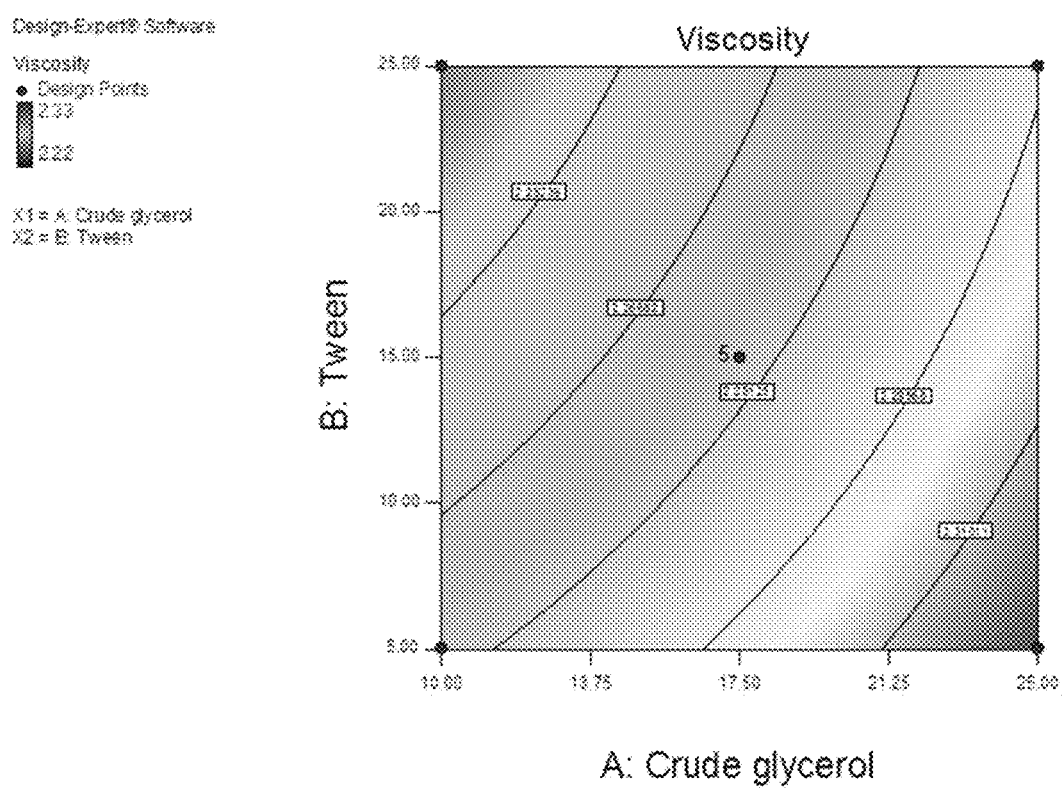
FIG. 9 illustrates the response of viscosity (cP) value across the interactions of crude glycerol (g/L) and Tween 80 (mg/L) using response surface plots.
Figure 10:
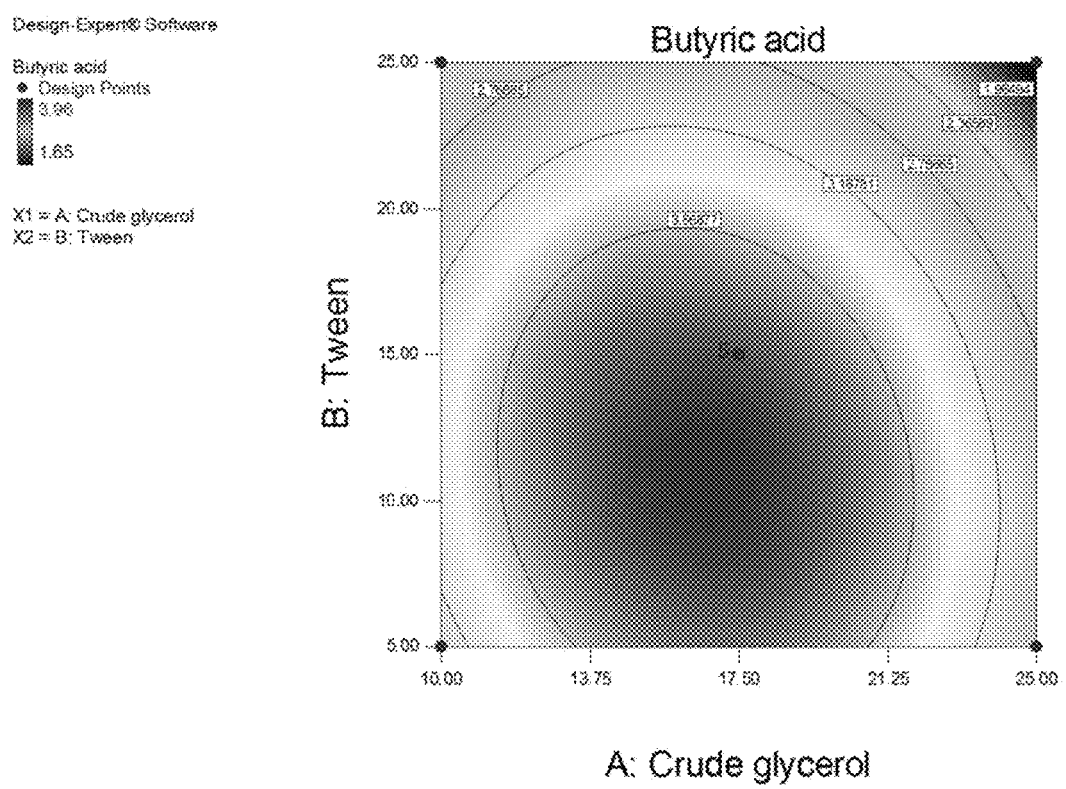
FIG. 10 illustrates the experimental responses of butyric acid production (g/L) with the fitting function of crude glycerol (g/L) and Tween concentration (mg/L) using response surface plots.
Figure 11:
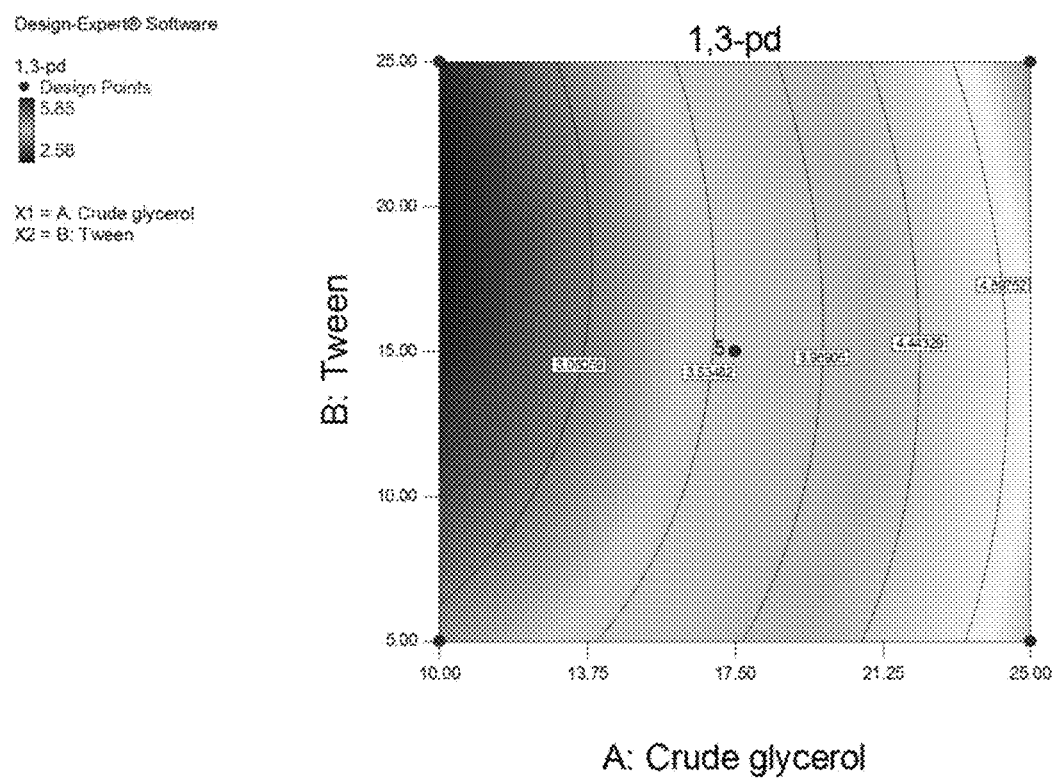
FIG. 11 illustrates the experimental responses of 1,3, Propanediol (1,3-pd) production (g/L) with the fitting function of crude glycerol (g/L) and Tween concentration (mg/L) using response surface plots.
Figure 12:
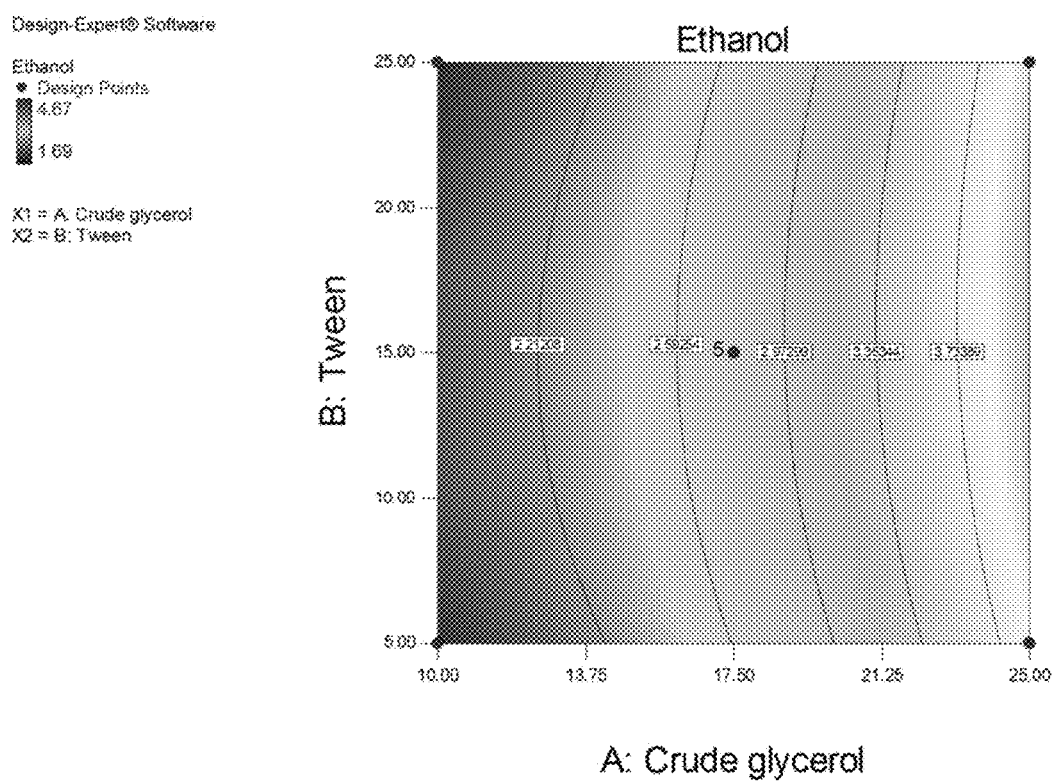
FIG. 12 illustrates the experimental responses of ethanol production (g/L) with the fitting function of crude glycerol (g/L) and Tween concentration (mg/L) using response surface plots.

The coefficient of crude glycerol (0.026) was slightly higher in comparison to the coefficient of Tween 80 (0.018), indicating the fact that viscosity is dependent on the concentration of crude glycerol. The response of viscosity value across the interaction of crude glycerol and Tween 80 using response surface plots are presented in FIG. 9.

At maximum concentration of Tween 80 (29.14 mg/L) in presence of 15 g/L of crude glycerol showed viscosity of 2.25±0.04 cP. At minimum concentration of Tween 80 (0.86 mg/L) in presence of crude glycerol (15 g/L), the viscosity measurement (2.30±0.03 cP) remained close to the viscosity of fermentation media without addition of Tween 80 at around (2.35±0.02 cP). At minimum concentration of crude glycerol (6.89 g/L) in presence of 15 mg/L of Tween 80 resulted in lowest viscosity value around 2.22±0.02 cP. However, at maximum concentration of crude glycerol (28.11 g/L) in presence of 15 mg/L of Tween 80 resulted in slight lowering of viscosity (2.33±0.04 cP) from (2.35±0.02 cP). Thus, the media viscosity was largely dependent upon the concentration of crude glycerol at first place, higher the concentration of crude glycerol higher the viscosity as seen from the FIG. 9. The observations are well supported with significant (p-values of 0.0040) contribution of crude glycerol on model response for viscosity.

The concentration of crude glycerol above the optimum value (17.5 g/L) for the run 1 (28.11 g/L) and 10 (25 g/L) even at optimum and increased value of Tween 80 (15 and 25 mg/L) showed minimum reduction in viscosity (2.33±0.04 and 2.29±0.06 cP) with decreased glycerol utilization (60.7±0.66 and 72.2±0.75%) resulting in decreased hydrogen production (24.4±1.43 to 25.5±0.63 mmol/L).

The concentration of crude glycerol above the optimum value caused minimum lowering of viscosity and also resulted in substrate inhibition so that there was decrease in substrate utilization resulting in decreased hydrogen production (as seen for run: 1, 6 and 10 in Table 5). In case of crude glycerol concentration below the optimum value for the run 5 (10 g/L), 9 (10 g/L) and 12 (6.89 g/L) at varying concentrations of Tween 80 (5, 25 and 15 mg/L) showed complete glycerol utilization (99.5-99.8%) reaching maximum hydrogen to 29.6±1.93 mmol/L. The concentration of crude glycerol below the optimum value was almost completely utilized by the microorganism, so that there was no further increase in hydrogen production even at optimum Tween 80 concentration. However, the effect of surfactant cannot be neglected in decreasing the media viscosity. Optimum crude glycerol concentration (17.5 g/L) and Tween 80 concentration (15 mg/L) for run (2, 3, 8, 11 and 13) helped in lowering the viscosity to minimum (2.27-2.28 cP) in comparison to without addition of Tween 80 at around (2.35±0.02 cP). The optimized condition showed near to complete utilization of crude glycerol reaching (84.7-87.8%) resulting in remarkable 1.5 increase from 21.4 to 32.1±0.03 mmol/L of hydrogen production.

Improvement of hydrogen production in presence of Tween 80 could be explained as follows: presence of surfactant in the medium would reduce its surface tension, which in turn would help to increase the apparent solubility of glycerol and as a consequence its microbial availability would be enhanced. Due to presence of three —OH groups, glycerol is highly hygroscopic. Therefore, at relatively high concentration, it might have difficulty in passing through the bacterial cell wall. The surfactant-glycerol interactions depend on the concentration of glycerol and critical concentration of surfactant will form micelle on glycerol molecules (Wang et al. Effects of nonionic surfactant and associative thickener on the rheology of polyacrylamide in aqueous glycerol solutions, Colloid and Polymer Science, 274 (1996) 138-144) [18]. The surfactant hydrophilic groups surround and interact with glycerol hydroxyl group by pointing hydrophobic group outward to form micelles. The formation of micelle decreases the surface/interfacial tension of water, increases solubility of glycerol and possibly enhances the accessibility of glycerol to microbes for increased utilization rate. Thus, presence of a surfactant might have beneficial effect during its transportation by increasing its bioavailability. This is just a hypothesis which needs further experimental evidence. However, such detailed investigation is beyond the scope of this example.

The by-product analysis at the end of fermentation resulted in the identification of ethanol, butyric acid and 1,3-PD concentration for different runs presented in Table 5, (the details of p-value along with response surface plots are presented as supplementary data). Glycerol fermentation by oxidative pathway results in hydrogen production with by-product formation, such as ethanol, acetic acid and butyric acid (Pachapur et al. Evidence of metabolic shift on hydrogen, ethanol and 1, 3-propanediol production from crude glycerol by nitrogen sparging under micro-aerobic conditions using co-culture of *Enterobacter aerogenes* and *Clostridium butyricum*, International Journal of Hydrogen Energy, 40 (2015) 8669-8676. In case of reductive pathway glycerol gets reduced into 1,3-PD with no production of hydrogen (Pachapur et al. Biohydrogen production by co-fermentation of crude glycerol and apple pomace hydrolysate using co-culture of *Enterobacter aerogenes* and *Clostridium butyricum*, Bioresource Technology, 193 (2015) 297-306). For butyric acid formation, 2 mol of hydrogen are produced during glycerol fermentation. In this example, the co-culture system followed the oxidative pathway and also reductive pathway with hydrogen production along with ethanol, butyric acid and 1,3-PD formation as seen in Table 5. The optimized condition for runs (2, 3, 8, 11 and 13) produced increased concentration of butyric acid averaging around ~3.86 g/L in comparison to other runs. Under optimized condition for runs (2, 3, 8, 11 and 13) the concentration of 1,3-PD was also minimum. 1,3-PD formation at 5.15±0.48 to 5.85±0.71 g/L resulted in decreased hydrogen production, which is well supported for the run 1, 6 and 10 for crude glycerol concentration from 25 to 28.11 g/L. The ethanol production across the optimized values for runs (2, 3, 8, 11 and 13) was within the range of 2.58 to 2.91 g/L. In case of maximum concentration of crude glycerol for runs (1, 6 and 10), the formation of ethanol was on higher side ranging from 4.04 to 4.67 g/L. The increased production of ethanol is directly co-related to decreased hydrogen production, as ethanol formation consumes NADH necessary for hydrogenase dependent hydrogen production (Pachapur et al. Biohydrogen production by co-fermentation of crude glycerol and apple pomace hydrolysate using co-culture of *Enterobacter aerogenes* and *Clostridium butyricum*, Bioresource Technology, 193 (2015) 297-306; and Heyndrickx et al. The fermentation of glycerol by *Clostridium butyricum* LMG 1212t2 and 1213t1 and *C. pasteurianum* LMG 3285, Applied Microbiology and Biotechnology, 34 (1991) 637-642). The optimum crude glycerol (17.5 g/L) and Tween 80 concentration (15 mg/L) not only favored the glycerol utilization but also channelized the oxidative and reductive pathway in co-culture system with minimum by-products formation for increased hydrogen production.

The analysis of by-product at the end of the fermentation delivered clarity on the pathway followed during glycerol fermentation and also provided the information on the rate limiting by-products formed during hydrogen production.

2.7.5. Hydrogen Production Across Validation Experiments

In order to prove the model hypothesis, the validation experiments across different sets using the optimized conditions were tested as presented in Table 7. The optimized run in the absence of Tween 80 resulted in the decreased hydrogen production around 25.56±0.91 mmol/L in comparison to its presence was 31.07±0.92 mmol/L. The glycerol utilization in absence of Tween was around 77.71±0.45% in comparison to 91.91±0.71% in presence of Tween. The results obtained followed the same trend of hydrogen production at 10 g/L crude glycerol in presence and absence of Tween 80 as shown in FIG. 6. The presence of Tween 80 supported the hypothesis with increased glycerol utilization along with increased hydrogen production. In the absence of Tween, degradation of crude glycerol is reduced and at a concentration higher than 15 g/L, it results in substrate inhibition for hydrogen production resulting in a pathway shift towards 1,3-PD production. The concentration of 1,3-PD is at higher range in the absence of Tween 80 at around 3.07±0.14 g/L in comparison to 2.17±0.08 g/L in presence of Tween. In order to determine the effect of yeast extract and polypeptone as a source of substrate on hydrogen production, crude glycerol was omitted from the fermentation medium. In absence of crude glycerol, around 4.69±0.76 mmol/L of hydrogen was produced suggesting the dependency of co-culture system on crude glycerol as substrate for hydrogen production. In the absence of yeast extract and polypeptone, the co-culture system was unable to produce increased hydrogen production. The co-culture system requires addition of these media components (yeast extract and polypeptone) as nitrogen source to maintain balanced carbon/nitrogen ratio during hydrogen production. The purpose of using co-culture system was to obtain increased hydrogen production and to minimize the use of costly reducing agents. Using a lone hydrogen producer in the case of *C. butyricum* required the addition of costly media component (L-cysteine). *E. aerogenes* (EA) acts as a reducing agent and possesses the property to remove oxygen and generate anaerobic condition for the growth of *C. butyricum* (CB). As mentioned above, the combination of these two microorganisms resulted in increased hydrogen production during co-culture system in comparison to mono-culture. The results obtained using optimized conditions for mono-culture (EA: 22.14±0.94 and CB: 15.43±0.79 mmol/L) and co-culture system (31.07±0.92 mmol/L), are in favor of using co-culture system for increased hydrogen production. *E. aerogenes* prefers crude glycerol over glucose source and is able to produce higher hydrogen in comparison to *C. butyricum*. *C. butyricum* prefers glucose derived substrate (Pachapur et al. Biohydrogen production by co-fermentation of crude glycerol and apple pomace hydrolysate using co-culture of *Enterobacter aerogenes* and *Clostridium butyricum*. Bioresource Technology, 193 (2015) 297-306) and a higher concentration of crude glycerol resulted in substrate inhibition (with only 13.49±1.10% of glycerol utilization) with decreased hydrogen production. In the present example, the co-culture system showed improved growth in comparison to mono-culture system with increased hydrogen production.

TABLE 7

Hydrogen production across the validation experiments using the optimized values from the central composite design.

| Optimum condition (CG: 17.5 g/L, Tween 80: 10 mg/L) | Hydrogen (mmol/L) | Ethanol (g/L) | Butyric acid (g/L) | 1,3-propaediol (g/L) | Glycerol utilization (%) |
| --- | --- | --- | --- | --- | --- |
| with Tween 80 | 32.07 ± 0.92 | 1.96 ± 0.16 | 2.73 ± 0.04 | 2.17 ± 0.08 | 91.91 ± 0.71 |
| without Tween 80 | 25.56 ± 0.91 | 1.88 ± 0.10 | 2.63 ± 0.07 | 3.07 ± 0.14 | 77.71 ± 0.45 |
| pretreated crude glycerol | 20.06 ± 0.51 | 2.03 ± 0.15 | 1.43 ± 0.70 | 2.67 ± 0.59 | 55.27 ± 1.18 |
| without crude glycerol | 4.69 ± 0.76 | 0.43 ± 0.03 | 0.82 ± 0.11 | 0.51 ± 0.06 | Nil |
| *E. aerogenes* only | 22.14 ± 0.94 | 1.72 ± 0.10 | 0.21 ± 0.13 | 2.48 ± 0.35 | 44.27 ± 0.82 |
| *C. butyricum* only | 15.43 ± 0.79 | 0.22 ± 0.06 | 1.39 ± 0.26 | 2.19 ± 0.19 | 13.49 ± 1.10 |

Utilization of crude glycerol requires initial pretreatment step for production of value-added products across studies presented in Table 8. The pretreatment step of mixing with distilled water, adjusting the pH for precipitation of solids, followed by centrifugation step and addition of media components, is necessary to reduce the viscosity of crude glycerol before being used for fermentation (Athalye et al. Use of biodiesel-derived crude glycerol for producing eicosapentaenoic acid (EPA) by the fungus *Pythium* irregular. Journal of Agricultural and Food Chemistry, 57 (2009) 2739-2744; Chi et al. A laboratory study of producing docosahexaenoic acid from biodiesel-waste glycerol by microalgal fermentation. Process Biochemistry, 42 (2007) 1537-1545; and Ethier et al. Continuous culture of the microalgae *Schizochytrium limacinum* on biodiesel-derived crude glycerol for producing docosahexaenoic acid. Bioresource Technology, 102 (2011) 88-93). Additional pretreatment steps are tedious and increase the production cost, however crude glycerol pretreatment step carried out for hydrogen production resulted with decreased production around 20.06±0.51 mmol/L in comparison to without pretreatment (31.07±0.92 mmol/L). The pretreatment step is carried out to remove crude glycerol inhibitor, such as soap, however soap removal resulted in 93.03% decreased hydrogen production (Sarma et al. Mitigation of the inhibitory effect of soap by magnesium salt treatment of crude glycerol—A novel approach for enhanced biohydrogen production from the biodiesel industry waste. Bioresource Technology, 151 (2014) 49-53). The presence of soap maintained the carbon-nitrogen ratio balance of the medium, acted as buffering/acid neutralizing agent, thus pretreatment of soap removal resulted in decreased hydrogen production.

Tween can induce a significant evolution in hydrogen production. Bioconversion of crude glycerol by energy intense pretreatment steps (such as pH adjustment, precipitation and centrifugation) and costly time-consuming techniques (such as immobilization and repeated fed-batch fermentation) for increased substrate utilization was eliminated by a simple addition of very small amount of surfactant. This resulted in economic solution for increased bioconversion and utilization rate of crude glycerol along with increased hydrogen production.

2.8 Conclusions

To increase glycerol utilization along with hydrogen production and decrease the viscosity of fermentation media, Tween 80 was selected as a surfactant. The CCD model helped to focus on determining the optimal concentration of crude glycerol and Tween 80 concentrations along with responses of hydrogen production, glycerol utilization and viscosity. Concentration of Tween ($p<0.05$) had a dominant effect on hydrogen production and crude glycerol had dominant effect on glycerol utilization and viscosity. The optimized conditions of crude glycerol: 17.5 g/L and Tween 80: 15 mg/L resulted in increased hydrogen production reaching a maximum of 32.1±0.03 mmol/L with 87.7% of glycerol utilization rate. The validation experiments in absence of Tween (25.56±0.91 mmol/L of $H_2$), in absence of

TABLE 8

Utilization of crude glycerol with initial pretreatment step during fermentation for different microorganisms to produce value-added products.

| Crude glycerol pretreatment steps | Microorganism used | Final product | Final output | Ref. |
|---|---|---|---|---|
| (1) Crude glycerol mixed with distilled water at 1:4 (v/v), (2) pH adjusted to 6.5 using HCl, (3) centrifugation at 5000 rpm and (4) addition of media nutrients | *Schizochytrium limacinum* SR21(ATCCMYA-1381) | Docosahexaenoic acid (DHA) | DHA yield of 4.91 g/L | Chi et al. Process Biochemistry, 42 (2007) 1537-1545 |
| (1) Crude glycerol mixed with distilled water, (2) pH adjusted to 3 using HCl, (3) centrifugation at 5000 rpm and (4) Addition of yeast extract | *Pythium irregulare* | Eicosapentaenoic Acid (EPA) | 14.9 mg/L-day | Athalye et al. Journal of Agricultural and Food Chemistry, 57 (2009) 2739-2744 |
| (1) Crude glycerol mixed with distilled water at 1:4 (v/v), (2) pH adjusted to 3 using $H_2SO_4$, (3) Static time of 30 min for two phase and (4) glycerol recovery using separation funnel, (5) addition of media nutrients | *Schizochytrium limacinum* | Docosahexaenoic acid (DHA) | 0.52 g/L-day | Ethier et al. Bioresource Technology, 102 (2011) 88-93 |
| (1) Crude glycerol mixed with distilled water at 1:4 (v/v), (2) pH adjusted to 11.37 (3) NaCl addition (4) centrifugation at 5000 rpm, (5) soap removal and addition of media nutrients | *Enterobacter aerogenes* | Hydrogen | 93.03% decreased hydrogen production | Sarma et al. Bioresource Technology, 151 (2014) 49-53 |
| (1) Crude glycerol mixed with distilled water at 1:2.7 (v/v), (2) Addition of Tween 80 0.0015% (v/v) along with media component (3) pH adjusted to 6.5 using HCl | *Enterobacter aerogenes* and *Clostridium butyricum* | Hydrogen | 32.1 ± 0.03 mmol/L (1.25-fold) increased production | This example |

In this example, in the absence of pretreatment step with minimum utilization of Tween 80 of around 0.0015% (v/v) resulted in increase in hydrogen production along with increased glycerol utilization, covering the unexplored side of bioconversion of crude glycerol. Addition of very small amounts of Tween 80 will be economical solution to pretreatment issues, further addition of surfactant eliminates contamination in bioreactors, improves medium characteristics, and enhance nutrient availability. The improved distribution and solubility of substrate with simple addition of crude glycerol (4.69±0.76), with pretreated crude glycerol (20.06±0.51) and across mono-culture system (15.43±0.79 to 22.14±0.94) resulted in decreased hydrogen production in comparison to increased hydrogen production (31.07±0.92) for the optimized conditions. The surfactant addition resulted in increased hydrogen production at higher concentration of crude glycerol with elimination of additional energy-intense pretreatment steps and costly time-consuming techniques to increase substrate utilization. Inclusion of the most suitable, low-cost, readily available surfactant source represented an excellent measure for viscosity reduction of crude glycerol for increased $H_2$ production and increased substrate utilization rate. Additionally, the utilization of Tween 80 at minimum concentration offered low-cost improved strategy to boost biodiesel industry through increased hydrogen production from crude glycerol.

TABLE 9

Summarized ANOVA for the response surface quadratic model for butyric acid, 1,3-Propanediol and ethanol.

| | p-value | | |
|---|---|---|---|
| Source | Butyric acid | 1,3-Propanediol | Ethanol |
| Model | 0.0098 | 0.0015 | <0.0001 |
| A-Crude glycerol | 0.1864 | <0.0001 | <0.0001 |
| B-Tween | 0.0257 | 0.5832 | 0.8076 |
| AB | 0.5422 | 0.4879 | 0.7580 |
| $A^2$ | 0.0027 | 0.1809 | 0.0173 |
| $B^2$ | 0.0165 | 0.1403 | 0.1055 |
| $R^2$ | 0.73 | 0.84 | 0.93 |

Final model equation (Eq. (4))

$$\text{Butyric acid}=3.86-0.25\times CG-0.48\times Tween-0.16\times CG\times Tween-0.83\times CG\times CG-0.58\times Tween\times Tween \quad (4)$$

Final model equation (Eq. (5))

$$\text{1,3-Propanediol}=3.62+1.17\times CG-0.083\times Tween+0.15\times CG\times Tween+0.23\times CG\times CG+0.26\times Tween\times Tween \quad (5)$$

Final model equation (Eq. (6))

$$\text{Ethanol}=2.79+1.05\times CG-0.021\times Tween+0.037\times CG\times Tween+0.28\times CG\times CG-0.16\times Tween\times Tween \quad (6)$$

Example 3

Valorization of Crude Glycerol and Eggshell Biowaste as Media Components for Hydrogen Production 3.1 Crude Glycerol as Substrate.

The CG used in this study was supplied by Rothsay®, Canada that recycles food and animal by-products for biodiesel production. The composition of CG (by w/w) is given as follows: glycerol (23.6%), carbon (35.9%), nitrogen (3.2%), ash (3.06%), moisture (5.75%) and matter organic non-glycerol (67.56%). Chemicals and reagents used in this example were purchased from Fisher Scientific®, VWR® and Lallemand®, Canada.

3.2 Microorganisms, Pre-Culture Media and Inoculum Development.

The co-culture system of *Enterobacter aerogenes* and *Clostridium butyricum* considered in this example were purchased from USDA, USA. The basal synthetic medium consisting (w/v) of glucose (1%), casein polypeptone (2.0%), $KH_2PO_4$ (0.2%), yeast extract (0.05%) and $MgSO_4.7H_2O$ (0.05%) maintained anaerobically at pH 6.5 was used for *E. aerogenes* pre-cultured at 30° C. The modified basal medium supplemented with 0.1% L-cysteine-$HCl.H_2O$ was used for *C. butyricum* precultured at 36° C. In distilled water, the exact concentrations of media components was dissolved using magnetic stirrer set-up. The pH of pre-culture media was set to 6.5 using NaOH, degassing by $N_2$ gas for 3 min and bottles sealed using pre-inserted septa followed by autoclave.

For inoculum development, log phase culture broth at (5% v/v) was used as inoculum throughout the example and cultures were incubated at 36° C. at 150 rpm in an orbital incubator shaker (INFORS-HT multitron standard).

3.3 Hydrogen Production Using Different Sized EGS.

To study the effect of variation in size of EGS on $H_2$ production, the EGS were first oven dried and then broken into small sizes using a mortar and pestle. The small pieces of EGS were later sieved through metal sifters and EGS of varying sizes from 1.7 mm$<x_1<$3.35 mm, 850 μm$<x_2<$1.7 mm, 300 μm$<x_3<$850 μm, 75 μm$<x_4<$300 μm and 33 μm$<x_5<$75 μm, were obtained. The collected EGS of varying sizes was collected separately and stored at 4° C. before use. Modified basal media containing (w/v): CG (1.75%), casein peptone (2%), yeast extract (0.05%), $KH_2PO_4$ (0.2%), $MgSO_4.7H_2O$ (0.05%) was mixed with EGS (0.25% w/v). The pH of the fermentation media was pH=6.5 and transferred to serum bottles with a 50 mL working volume. The $N_2$ sparging, sealing, autoclave and incubation steps are similar to the inoculum development step as explained earlier above. The concentration of CG at 1.75% was found to be optimum in authors earlier studies for $H_2$ production, and addition of EGS at concentration of 0.25% (w/v) equivalent to exact concentration of (0.2% $KH_2PO_4$ and 0.05% $MgSO_4.7H_2O$) was carried out in triplicates. The experimental runs were performed in triplicates and the presented values are the averages of triplicates with standard deviation (±) values as error bars.

3.4 Repeated Batch Culture of $H_2$ Production Using Different Sized EGS.

After the batch culture of $H_2$ production using varying size of EGS, 47.5 mL of spent media was drawn out using a syringe with long needle and syringe filter (0.45 μm) fitted to a peristaltic pump. The syringe filter was used to retain the eggshells inside and drawing out only spent media from the serum bottle. Later, 47.5 mL of fresh autoclaved medium was added and the serum bottle was degassed to zero down $H_2$ concentration before repeated batch culture. The spent media of 2.5 mL was used as inoculum for the fresh medium during repeated batch culture fermentation. The steps to draw out spent media, addition of fresh media and vacuum creation was carried out in laminar air flow under sterilized conditions.

3.5 EGS as Immobilization Support.

The immobilizing property of EGS provides necessary compatibility for attachment, adsorption and growth of microorganisms. To determine the immobilizing potential of EGS in the co-culture system during $H_2$ production, the eggshells were collected from the spent media at the end of the fermentation, processed and analyzed by scanning electron microscopy.

3.6 Hydrogen Production at Different Concentrations of EGS.

To determine the exact concentration of EGS of size $x_5$ (33 μm$<x_5<$75 μm) for increased $H_2$ production, the amount of EGS was varied from 0.5, 1, 2 and 4% (w/v). In the presence of modified basal media at CG 1.75% with yeast, peptone and at increasing concentration of EGS of size $x_5$ from 0.5 to 4% was carried out in triplicates.

3.7 Effect of EGS in Presence and Absence of Media Components During $H_2$ Production.

To study the effect of EGS during $H_2$ production with modified basal media consisting of (w/v): CG (1.75%), EGS of size $x_5$ (0.25%) and in presence and absence of casein peptone (2%), yeast extract (0.05%), $KH_2PO_4$ (0.2%), $MgSO_4.7H_2O$ (0.05%) was carried out. The fermentation media in presence and absence of each component was carried out as explained above in inoculum development step. A control experiment for synthetic $CaCO_3$ at exact concentration of EGS was carried out for comparative study. In addition, validation experiments in presence and absence of CG were also carried out in triplicates.

3.8 Semi-Continuous $H_2$ Production Using 7.5 L Bioreactor.

The co-culture system of $H_2$ production using EGS in the absence of media components using 7.5 L bioreactor (Labfors, IINFORS-HT, Switzerland) was carried out. The semi-continuous approach eliminated substrate inhibition and successfully developed a low-cost bio-engineering system for $H_2$ production. The initial CG concentration in the bioreactor was around 10 g/L, which was diluted using distilled water to make-up for the working volume of 3 L. After 8 hours of fermentation, CG concentration at 120 g/L was drop wise added to reactor and equal amount of fermented medium was drawn through various openings using a peristaltic pump. The drop wise feeding and drawing of fermented medium was maintained at constant speed using peristaltic pump, so that the medium volume of the bioreactor was constant throughout the fermentation. The real time values of different parameters, such as (pH, rpm, dissolved oxygen, temperature and hydrogen) were monitored and recorded using Iris software (Labfors, IINFORS-HT, Switzerland) operated over a system. To account for hydrogen partial pressure, once the $H_2$ concentration reached 30-35% (v/v) in the headspace of the reactor, pure $N_2$ was sparged. The operating conditions (pH: 6.5, temperature: 36° C. and rpm: 100) were kept constant during fermentation as described in Example 1.

3.9 Hydrogen Analysis by GC.

At the end of each fermentation experiment, the gas samples were collected in vacuumed sample vials using gas tight syringe and later were analyzed by gas chromatography (GC). The technical specifications of the GC instrument were: Model: Varian™ 3800, USA, fitted with a 3 m PoraPLOT Qe column (Agilent® technology, USA) and equipped with a thermal conductivity detector (TCD). The GC set-up with injector, column temperature and detector temperature were set at 100° C. and carrier gas $N_2$ was used at a flow rate of 3.5 mL/min. Considering the temperature and atmospheric pressure during the experimental runs, the volume of $H_2$ gas produced was calculated and expressed in mmol concentration unit.

3.10 End-Metabolites/by-Products Analysis by GC-FID.

The concentrations of ethanol, butyric acid, acetic acid and 1,3-propanediol (1,3-PD) was analyzed on ZB-WAX plus column fitted with flame ionization detector (FID) detector in a gas chromatography (GC) (7890B GC-Agilent®, Santa Clara, Calif.) set-up. The GC conditions at a flow rate of 1 mL/min using helium carrier gas at a temperature profile of 80-240° C. under 8.4 min method run time was developed.

3.11 Bacterial Morphology Analysis by Scanning Electron Microscopy (SEM).

The EGS at the end of the repeated batch fermentation were recovered and washed twice in potassium phosphate buffer (50 mM, pH 6.5). The bacterial cells were fixed, washed and dehydrated according to the sample preparation steps mentioned earlier and later the fixed cells were analyzed by SEM, Carl Zeiss EVO® 50.

3.12 Results and Discussion 3.12.1 Hydrogen Production in Presence of Different Sizes of EGS.

To determine the role of EGS during hydrogen production using CG (1.75%) in presence of modified basal medium, the co-culture studies was carried out in presence of different sizes of EGS. At the end of batch fermentation, the $H_2$ production and end-metabolite production obtained with the different sizes of EGS are presented in Table 10. The different sizes of EGS obtained using metal sieves were labelled as $x_1$ to $x_5$. For different sizes of EGS experimented, the highest $H_2$ production (36.53±0.53 mmol/L) was obtained for the size $x_5$ around and the lower production (29.33±0.38 mmol/L) resulted with $x_1$ size. The pH of the spent media at the end of fermentation using EGS was within 6.00 to 6.50 in comparison to ~5.5 in absence of EGS. During the fermentation with the accumulation of different organic acids (acetate and butyrate) along with solvents (ethanol), the fermentation pH decreased to around ~5.5 from 6.5 causing pathway shift with lower $H_2$ production. Addition of EGS helped to maintain near to the optimum pH required for the growth of E. aerogenes and C. butyricum. The $H_2$ concentration (36.53±0.53 mmol/L) obtained with EGS was higher in comparison to 32.1±0.03 mmol/L without EGS. In case of size $x_5$, acetic acid was produced at higher concentration (2.92±0.01 g/L) in comparison to other applied sizes of eggshells, which resulted in increased $H_2$ production for size $x_5$. The $CaCO_3$ (Hydrogen Bond Acceptor Count=3) present in the eggshell acted as indirect H-acceptor and gradually diverting the fermentation from 1,3-PD towards acetate and $H_2$ formation. The increased production of acetate can also be due to the decalcification reaction accounted during conversion of calcium carbonate present in EGS into calcium acetate. The $H_2$ production increased with increased production of acetic acid, as 3 mole of $H_2$ are released from 1 mole of acetate. The decreased size of eggshell resulted in the increased production of $H_2$. The larger size in case of $x_1$ to $x_4$, tend to settle down to form heaps at the bottom of the serum bottle during the fermentation. However, in case of size $x_5$, there was no settling down of EGS resulting in constant contact with media for sufficient mixing system resulting in increased $H_2$ production. The increased size of EGS accentuated the mixing problem with the formation of dead zones (with insufficient mixing) resulting in local accumulation of EGS heaps. The dead zone across the fermentation with limited media exposure tends to decrease the fermentation performance resulting in decreased $H_2$ production. Homogenous mixing directly influences the uniform distribution of media components by keeping microorganisms in suspension with no dead zone formation desirable to increase the performance of bioreactor.

TABLE 10

Hydrogen (mmol/L) and end-metabolite concentration (g/L) obtained with varying sizes of eggshells at 0.25% (w/v) concentration during batch and repeated batch fermentation.

| | Hydrogen (mmol/L) | Ethanol (g/L) | Butyric acid (g/L) | Acetic acid (g/L) | 1,3-PD (g/L) |
|---|---|---|---|---|---|
| Batch fermentation eggshell size | | | | | |
| 1.7 mm < $x_1$ < 3.35 mm | 29.33 ± 0.38 | 1.11 ± 0.12 | 1.23 ± 0.01 | 1.33 ± 0.11 | 3.56 ± 0.34 |
| 850 μm < $x_2$ < 1.7 mm | 30.97 ± 0.84 | 1.31 ± 0.07 | 1.28 ± 0.02 | 1.91 ± 0.04 | 3.53 ± 0.17 |

TABLE 10-continued

Hydrogen (mmol/L) and end-metabolite concentration (g/L) obtained with varying sizes of eggshells at 0.25% (w/v) concentration during batch and repeated batch fermentation.

| | Hydrogen (mmol/L) | Ethanol (g/L) | Butyric acid (g/L) | Acetic acid (g/L) | 1,3-PD (g/L) |
|---|---|---|---|---|---|
| 300 μm < $x_3$ < 850 μm | 32.21 ± 0.96 | 1.16 ± 0.20 | 1.27 ± 0.02 | 2.29 ± 0.06 | 3.53 ± 0.17 |
| 75 μm < $x_4$ < 300 μm | 33.57 ± 0.82 | 1.14 ± 0.24 | 1.31 ± 0.04 | 2.49 ± 0.06 | 3.51 ± 0.28 |
| 33 μm < $x_5$ < 75 μm | 36.53 ± 0.53 | 1.27 ± 0.11 | 1.44 ± 0.04 | 2.92 ± 0.01 | 3.87 ± 0.15 |
| Repeated-batch fermentation | | | | | |
| 1.7 mm < $x_1$ < 3.35 mm | 34.93 ± 0.81 | 1.23 ± 0.37 | 1.54 ± 0.10 | 2.78 ± 0.08 | 3.78 ± 0.24 |
| 850 μm < $x_2$ < 1.7 mm | 35.76 ± 0.91 | 1.45 ± 0.10 | 1.74 ± 0.09 | 2.89 ± 0.06 | 3.99 ± 0.15 |
| 300 μm < $x_3$ < 850 μm | 36.50 ± 0.82 | 1.64 ± 0.03 | 1.79 ± 0.04 | 2.95 ± 0.03 | 3.83 ± 0.16 |
| 75 μm < $x_4$ < 300 μm | 37.45 ± 0.70 | 1.79 ± 0.28 | 2.32 ± 0.03 | 3.14 ± 0.22 | 4.16 ± 0.28 |
| 33 μm < $x_5$ < 75 μm | 41.16 ± 0.95 | 1.68 ± 0.36 | 2.44 ± 0.11 | 3.46 ± 0.14 | 4.28 ± 0.31 |

The eggshell addition maintained the media pH, resulted in enhanced hydrogen production with decreased size of eggshells. In order to determine the reuse property of eggshell, repeated batch fermentation was carried out.

3.12.2 Repeated Batch Culture of $H_2$ Production in Presence of Different Sizes of EGES.

In addition to maintaining the pH of the fermentation, EGS also act as immobilizing agent. Hydrogen production at the end of batch fermentation with different sizes was later supplemented with fresh degassed media and repeated batch fermentation was carried out. The repeated batch cycle determined the immobilizing property of EGS and ability to reuse eggshells during $H_2$ production. The $H_2$ and end-metabolites production obtained in the repeated batch fermentation in presence of different varying sizes of EGS are presented in Table 10. The $H_2$ and metabolite production profile in case of repeated batch was similar to batch fermentation. The highest $H_2$ production was around 41.16±0.95 mmol/L for size $x_5$ and the lowest production of 34.93±0.81 mmol/L for size $x_1$. In case of repeated fermentation, the concentration of end-metabolite was higher in comparison to batch fermentation. In case of repeated fermentation, the spent media as inoculum attributed to increased cell proliferation and higher adaptation to the CG resulting in enhanced $H_2$ production. The spent media at 5-10% inoculum size in case of E. aerogenes resulted in 13.37% increased $H_2$ production. The $2^{nd}$ cycle of repeated batch fermentation resulted in decreased $H_2$ production with increased production 1,3-PD (data not shown). In case of $2^{nd}$ cycle of repeated fermentation, the incoming CG with different impurities tend to inhibit the $H_2$ production pathway resulting in 1,3-PD formation with decreased $H_2$ production. The reuse property of EGS property was determined with increased $H_2$ production across repeated fermentation.

Figure 13:
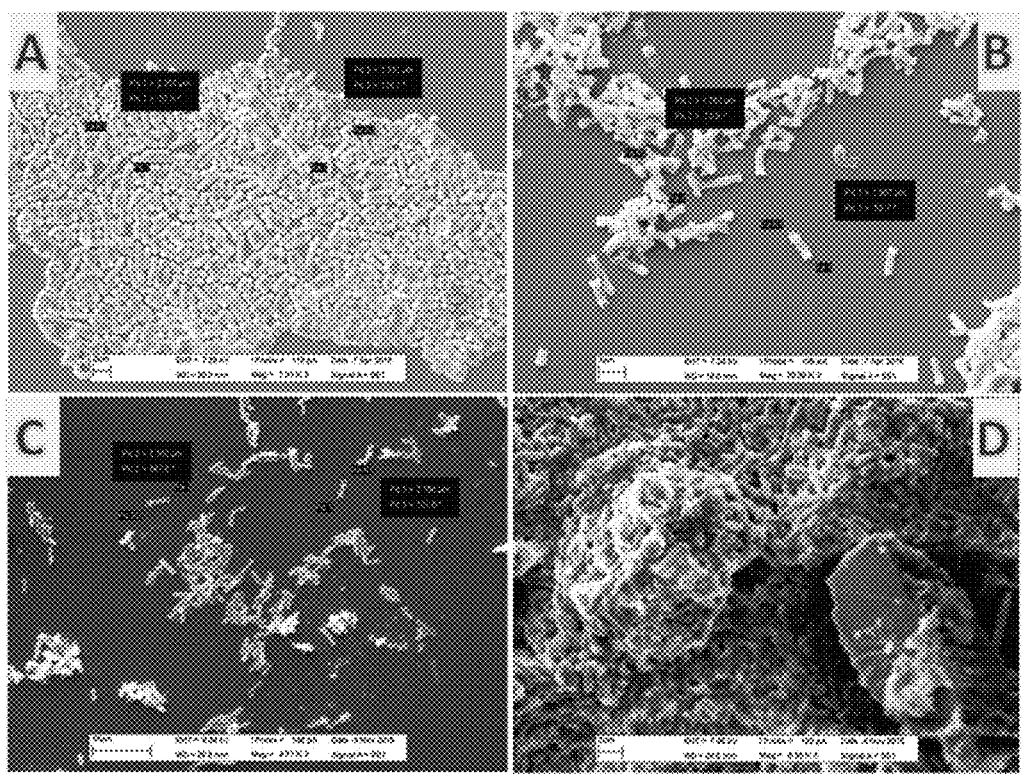
FIG. 13 illustrates a scanning electron micrograph of: (A) mono-culture *E. aerogenes* without eggshell; (B) mono-culture *C. butyricum* without eggshell; (C) co-culture of *E. aerogenes* and *C. butyricum* without e

The potential of EGS as immobilizing support materials for the two bacterial strains was confirmed from the SEM micrographs. The EGS possesses the property of immobilization compatibility for attachment, adsorption and proliferation of microorganisms. SEM micrograph of mono-culture and co-culture system in absence and presence of eggshell are represented in the FIG. 13. The rod-shaped morphology of E. aerogenes and C. butyricum can be seen in the mono-culture system in the FIG. 13 1(A and B). The co-culture system of E. aerogenes and C. butyricum in the absence of eggshell can be seen in FIG. 13 (C). The figure also represents the growth/presence of both the microorganisms during $H_2$ production in the co-culture system. The blunt end of C. butyricum can be easily differentiated from round ended E. aerogenes in the co-culture. The co-culture system was studied in the presence of eggshell and bacterial immobilization on the surfaces of EGS can be seen in the FIG. 13 (D). The increase in immobilized bacterial biomass suggested the role of eggshells as immobilizing surface during co-culture.

The advantages of co-culture over mono-culture were justified with increased $H_2$ production, increased co-substrate utilization, increased glycerol uptake and decreased by-product production. However, for the first time the simultaneous growth of E. aerogenes and C. butyricum in the co-culture system was justified at molecular level using SEM in this example.

3.12.3 Hydrogen Production in Presence of Increasing Concentration of EGS.

In comparison to the other four applied size ranges ($x_1$, $x_2$, $x_3$, and $x_4$) of EGS, the size range $x_5$ resulted in the highest $H_2$ production in both batch and repeated fermentation conditions. To determine the optimum concentration for maximum $H_2$ production, different concentrations (0.5 to 4%, w/v) of EGS was used. The production profiles of $H_2$ and end-metabolite obtained with different concentrations (%) of $x_5$ are presented in Table 11. The highest $H_2$ production was around 37.03±0.32 mmol/L in case of 1% w/v of eggshell and minimum was around 32.73±0.22 mmol/L for 4% of eggshell of size $x_5$. The $H_2$ production in case of increasing concentration of EGS followed both oxidative with production of acetate, butyrate and ethanol along with reductive pathway with production of 1,3-PD as seen from the Table 11. The increase in the production of $H_2$ 37.58±0.32 mol/L while using 1% (w/v) EGS was marginal increase in comparison to 36.53±0.53 mmol/L using 0.25% (w/v) of EGS concentration as seen in Table 10. The $H_2$ production in presence of 0.125% (w/v) of EGS was lower in comparison to $H_2$ production at 0.25% (w/v) EGS. The concentration of 0.25% (w/v) eggshell in case of 1.75% (w/v) CG resulted in the optimum conditions for increased $H_2$ production for the co-culture system. The optimum condition of 0.25% (w/v) of EGS matched the total (w/v) of $KH_2PO_4$ (0.2%) and $MgSO_4.7H_2O$ (0.05%) used in the basal media for the inoculum growth.

TABLE 11

Hydrogen (mmol/L) and end-metabolite concentration (g/L) in presence of increasing concentration (w/v) (%) of eggshells of size $x_5$ (33 μm < $x_5$ < 75 μm).

| Batch fermentation eggshell of size $x_5$ concentration (%) | Hydrogen (mmol/L) | Ethanol (g/L) | Butyric acid (g/L) | Acetic acid (g/L) | 1,3-PD (g/L) |
|---|---|---|---|---|---|
| 0.25 | 36.53 ± 0.53 | 1.27 ± 0.11 | 1.44 ± 0.04 | 2.92 ± 0.01 | 3.87 ± 0.15 |
| 0.5 | 37.05 ± 0.41 | 1.11 ± 0.02 | 1.22 ± 0.01 | 2.75 ± 0.05 | 3.62 ± 0.12 |
| 1 | 37.58 ± 0.32 | 1.42 ± 0.03 | 2.15 ± 0.02 | 3.08 ± 0.02 | 3.75 ± 0.01 |
| 2 | 36.81 ± 0.11 | 1.46 ± 0.13 | 1.99 ± 0.04 | 2.97 ± 0.01 | 3.81 ± 0.02 |
| 4 | 32.73 ± 0.22 | 1.69 ± 0.04 | 1.38 ± 0.01 | 2.84 ± 0.05 | 3.94 ± 0.03 |

Increase in the concentration of EGS resulted in the marginal increase in the hydrogen production and 0.25% (w/v) of EGS of size $x_5$ was the optimum condition. The optimum condition of 0.25% (w/v) of eggshell of size $x_5$ was fixed and used in the later studies.

TABLE 12

Hydrogen (mmol/L) and end-metabolite concentration (g/L) using co-culture system in presence and absence of media components at 17.5 g/L of CG with eggshell $x_5$ at 0.25% (w/v) concentration.

| Batch fermentation | Hydrogen (mmol/L) | Ethanol (g/L) | Butyric acid (g/L) | Acetic acid (g/L) | 1,3-PD (g/L) |
|---|---|---|---|---|---|
| Without yeast extract | 22.08 ± 0.29 | 1.34 ± 0.34 | 0.21 ± 0.01 | 0.79 ± 0.23 | 2.94 ± 0.40 |
| Without casein peptone | 21.86 ± 0.44 | 2.12 ± 0.01 | 0.17 ± 0.02 | 1.62 ± 0.06 | 4.46 ± 0.15 |
| Without $KH_2PO_4$ | 27.57 ± 0.32 | 0.90 ± 0.01 | 0.19 ± 0.02 | 1.84 ± 0.09 | 3.62 ± 0.02 |
| Without $MgSO_4 \cdot 7H_2O$ | 30.18 ± 0.24 | 1.06 ± 0.02 | 1.24 ± 0.01 | 2.21 ± 0.10 | 3.14 ± 0.08 |
| Without $KH_2PO_4$ and $MgSO_4 \cdot 7H_2O$ | 30.73 ± 0.32 | 1.29 ± 0.50 | 1.22 ± 0.03 | 1.79 ± 0.17 | 2.22 ± 0.14 |
| With synthetic $CaCO_3$ | 26.43 ± 0.23 | 1.18 ± 0.03 | 0.21 ± 0.10 | 2.12 ± 0.02 | 3.55 ± 0.08 |

3.12.4 Hydrogen Production with and without Different of Media Components.

In order to determine the role of EGS, each of the media components was replaced during $H_2$ production. The optimum condition of modified basal media CG (1.75%), and in presence and absence of casein peptone (2%), yeast extract (0.05%), $KH_2PO_4$ (0.2%), $MgSO_4 \cdot 7H_2O$ (0.05%) was studied at EGS size of $x_5$ with 0.25% w/v concentration. The experimental sets, along with $H_2$ and end-metabolite production with and without media components are presented in Table 12. The highest $H_2$ production was around 30.73±0.32 mmol/L in case of media composition without $KH_2PO_4$ and $MgSO_4 \cdot 7H_2O$ and minimum was around 21.86±0.44 mol/L in case of media composition without yeast extract. The decrease in pH towards weakly alkaline favors methanogenesis, homoacetogenesis and direct consumption of produced $H_2$, requiring addition of external buffering agents. The purpose of this example was to determine the role of eggshell as a replacement for any of the possible media supplements. In case of $H_2$ production, the property of EGS as neutralizing agent is justified and can be used as possible supplement to replace costly media components ($KH_2PO_4$ and $MgSO_4 \cdot 7H_2O$). The role of $KH_2PO_4$ is to regulate the pH during fermentation, and $MgSO_4 \cdot 7H_2O$ addition as trace metal necessary for biomass generation during $H_2$ production. The composition of EGS with $CaCO_3$ (94%), magnesium carbonate (1%), calcium phosphate (1%) acts as a natural neutralizing agent for the microorganisms. Eggshell support resulted in higher production (30.73±0.32 mmol/L) in comparison to synthetic $CaCO_3$ with only 26.43±0.23 mmol/L $H_2$ production. In the absence of nitrogen source, such as yeast extract and peptone, the co-culture system was able to produce around 22.08±0.29 mmol/L of $H_2$. The presence of organic matter (4%), in the EGS along with 3% nitrogen content in CG supplemented the nitrogen source during $H_2$ production.

The EGS with the role of maintaining the fermentation pH, immobilizing agent along with possible replacement as neutralizing agent can be used for hydrogen production from crude glycerol.

3.12.5 Hydrogen Production in Comparative Studies.

In the presence and absence of media components while using the EGS, the co-culture system was able to produce the increased $H_2$ production. In order to determine the role of EGS in complete absence of media components, comparative studies were carried out. The conditions used across the studies included CG at 1.75%, EGS size $x_5$ (0.25%) along with media components (casein peptone (2%), yeast extract (0.05%), $KH_2PO_4$ (0.2%), $MgSO_4 \cdot 7H_2O$ (0.05%)). The experimental plan along with $H_2$ and end-metabolites production across the comparative studies is presented in the Table 13. In the absence of the EGS using 1.75% of CG, the co-culture system was able to produce around 32.07±0.92 mmol/L of $H_2$. In this case, the fermentation followed the reductive pathway with butyric acid production (2.73±0.04 g/L) with trace amount of acetic acid (0.27±0.03 g/L) production. Butyric acid theoretical yield from CG is only 2 mole of $H_2$ in comparison to acetic acid production with 3 mole of $H_2$. For eggshell, the co-culture system was able to produce higher $H_2$ at around 36.53±0.53 mmol/L following the reductive pathway with production of acetic acid (2.92±0.01 g/L) along with butyric acid (1.44±0.04 g/L). In presence of EGS, the glycerol fermentation favored the acetic acid production along with increased $H_2$ production (as explained in section 3.1). The same condition was studied for the mono-culture system. In case of E. aerogenes, the $H_2$ production was around (24.21±0.52 mol/L)

along with acetic acid (1.54±0.02 g/L) and trace amount of 1,3-PD production (2.70±0.03 g/L). For *C. butyricum*, only $H_2$ production was around (20.14±0.38 mmol/L) with butyric acid (1.81±0.03 g/L) and 1,3-PD production (2.80±0.08 g/L). The concentration of CG at 1.75% w/v acts as substrate inhibitor during mono-culture studies resulting in increased production of 1,3-PD for both *E. aerogenes* and *C. butyricum*. The co-culture system in the presence of CG with EGS and in the absence of media components resulted in (31.66±0.55 mmol/L) of $H_2$ production along with acetic acid (2.67±0.03 g/L) and butyric acid (1.16±0.01 g/L) production.

The comparative studies at optimized conditions validated the replacement of media components by EGS during $H_2$ production in presence of CG by co-culture system.

3.12.6 Semi-Continuous $H_2$ Production Using 7.5 L Bioreactor.

The maximum benefit in terms of substrate inhibition, product inhibition, maintaining pH during generation of metabolites and elimination of media components was achieved with semi-continuous low-cost approach of $H_2$ production. The example was carried out using mono-culture (*E. aerogenes*) in presence of only CG along with distilled water without media components. The approach

TABLE 13

Hydrogen (mmol/L) and end-metabolite concentration (g/L) for comparative example across mono- and co-culture system at 17.5 g/L of CG with eggshell $x_5$ at 0.25% (w/v) concentration.

| Batch fermentation | Hydrogen (mmol/L) | Ethanol (g/L) | Butyric acid (g/L) | Acetic acid (g/L) | 1,3-PD (g/L) |
| --- | --- | --- | --- | --- | --- |
| CG + media components, without eggshell for co-culture | 32.07 ± 0.92 | 1.96 ± 0.16 | 2.73 ± 0.04 | 0.27 ± 0.03 | 2.17 ± 0.08 |
| CG + media components + eggshell for co-culture | 36.53 ± 0.53 | 1.27 ± 0.11 | 1.44 ± 0.04 | 2.92 ± 0.01 | 3.87 ± 0.15 |
| CG + media components + eggshell for *E. aerogenes* only | 24.21 ± 0.52 | 1.25 ± 0.01 | 0.90 ± 0.01 | 1.54 ± 0.02 | 2.70 ± 0.03 |
| CG + media components + eggshell for *C. butyricum* only | 20.14 ± 0.38 | 1.13 ± 0.02 | 1.81 ± 0.03 | 0.84 ± 0.02 | 2.80 ± 0.08 |
| CG + eggshell, without media components for co-culture | 31.66 ± 0.55 | 1.94 ± 0.06 | 1.16 ± 0.01 | 2.67 ± 0.03 | 2.56 ± 0.16 |
| Media components + eggshell, without CG for co-culture | 6.35 ± 0.05 | 0.02 ± 0.03 | 0.32 ± 0.02 | 0.13 ± 0.04 | 0.42 ± 0.12 |

The $H_2$ concentration (31.66±0.55 mmol/L) obtained without media components were comparable to without EGS (32.07±0.92 mmol/L). In the absence of media components, the limiting conditions, such as neutralizing property and nutrient/organic source were supplemented by EGS and CG for $H_2$ production. The media components might have masked the available nutrients from both CG and eggshell, which resulted in marginal $H_2$ production (32.07±0.92 mmol/L). However, with EGS as replacement of media components the co-culture system was able to produce sufficient $H_2$ (31.66±0.55 mmol/L). The conditions of absence of CG and in presence of eggshell and media components resulted in 6.35±0.05 mol/L of $H_2$.

was modified with addition of 0.25% (w/v) EGS and carried out using co-culture system (*E. aerogenes* and *C. butyricum*). The purpose was to scale-up the results obtained during serum bottle of 125 mL volume to bioreactor with 7.5 L volume. During the comparative example, the co-culture system produced more hydrogen in comparison to mono-culture system. Table 14, presents cost analysis for semi-continuous process considered for each of the comparative studies. The source of media components and their costs at the bulk industrial purchase are referred from www.alibaba.com. The total cost for bioconversion of 1 kg of CG by co-culture system using only EGS resulted in around \$3.15 in comparison to using media components was around \$43.95.

TABLE 14

Cost analysis for bioconversion of 1 kg of crude glycerol into hydrogen for each of the comparative studies using co-culture system.

| | | Cost (\$) | | |
| --- | --- | --- | --- | --- |
| Process and materials required | Amount for bioconversion of 1 kg CG | CG + media components, without EGS | CG + media components + EGS | CG + EGS, without media components |
| Inoculum development (2.5 L) | | | | |
| Glucose monohydrate (1%) | 25 g | 0.015 | 0.015 | 0.015 |
| Casein peptone (2%) | 50 g | 2.125 | 2.125 | 2.125 |
| KH2PO4 (0.2%) | 5 g | 0.007 | 0.007 | 0.007 |
| Yeast extract (0.05%) | 1.25 g | 0.016 | 0.016 | 0.016 |

TABLE 14-continued

Cost analysis for bioconversion of 1 kg of crude glycerol into hydrogen for each of the comparative studies using co-culture system.

| | | Cost ($) | | |
|---|---|---|---|---|
| Process and materials required | Amount for bioconversion of 1 kg CG | CG + media components, without EGS | CG + media components + EGS | CG + EGS, without media components |
| MgSO4 (0.05%) | 1.25 g | 0.001 | 0.001 | 0.001 |
| L-cysteine (0.1%) | 2.5 g | 0.225 | 0.225 | 0.225 |
| Media preparation (47.5 L) | | | | |
| Crude glycerol | 1 kg | 0.100 | 0.100 | 0.100 |
| Casein peptone (2%) | 950 g | 40.375 | 40.375 | NIL |
| KH2PO4 (0.2%) | 95 g | 0.133 | 0.133 | NIL |
| Yeast extract (0.05%) | 23.75 g | 0.297 | 0.297 | NIL |
| MgSO4 (0.05%) | 23.75 g | 0.012 | 0.012 | NIL |
| EGS (0.25%) | 118.75 g | NIL | 0.013 | 0.013 |
| Fermentation (143 h) | 13.15 kWh | 0.648 | 0.648 | 0.648 |
| Total cost ($) for bioconversion of 1 kg CG | | 43.95 | 43.97 | 3.15 |

Figure 14:
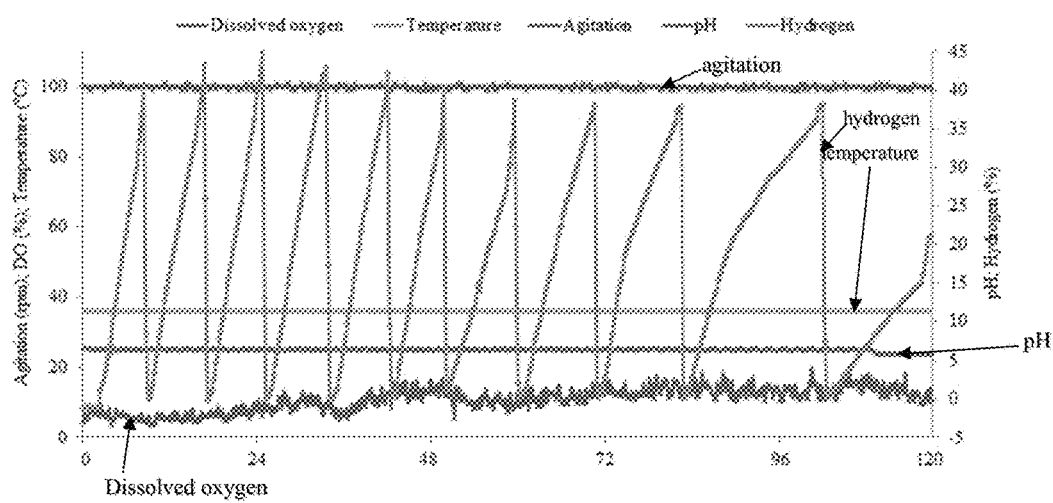
FIG. 14 illustrates the online monitored data of the parameters (pH, dissolved oxygen, temperature, agitation and hydrogen) during semi-continuous fermentation (7.5 L) using co-culture system for hydrogen production.

In context of the above results and to develop cost-effective process, co-culture system without media components using 0.25% (w/v) EGS with semi-continuous approach of $H_2$ production was carried out using. The online monitored data of the parameters (pH, dissolved oxygen, temperature, agitation and hydrogen) during semi-continuous fermentation (7.5 L) using co-culture system for hydrogen production are represented in the FIG. 14.

Using *E. aerogenes* with semi-continuous approach produced around 210 mmol or 5.18 L $H_2$/L of medium with 65% glycerol utilization. In this example, with co-culture system using 0.25% (w/v) EGS, almost 1.5-fold increase with 312.12 mmol or 7.69 L $H_2$/L of medium with 86.65% glycerol utilization was obtained. The co-culture system in absence of EGS resulted in only 1.15-fold increase in absence of EGS (data not shown). The results obtained across the serum bottle study with 125 mL volume matched the results obtained using bioreactor of 7.5 L volume. Different types of bioreactors with varying volumes, with batch, fed-batch and continuous and stirred reactors have been used for $H_2$ production. The semi-continuous bioreactor works with CG diluted only with distilled water along with EGS to reduce substrate inhibition, increase glycerol utilization and reduce overall process cost. Based on the results, parallel treatment of CG along with eggshell can be achieved with sustainable state of $H_2$ production using semi-continuous bioreactor.

Every year, around ±5700 tons of CG is produced across the Quebec region. With the optimized condition from this example, around 814 tons of EGS are required at ratio of 1:7. Food processing industry spends about $12 per hour to dry one ton on EGS before landfilling or composting with increasing problems of disposal cost, distant landfills with excess field capacity. The European Union has already banned landfill disposal or composting of EGS waste with moisture content of over 4%. However, with the proposed valorization approach of using EGS will save around $100,000/year for small and medium sized food processing industry. In addition, the biodiesel industry will generate revenue from the waste CG with efficient process of $H_2$ production as a viable alternative energy fuel.

The method of using the EGS during the $H_2$ production from CG by co-culture system is a novel approach. The ability of EGS to neutralize and maintain the pH during the $H_2$ production can replace the cost of the neutralizing agent, which in turn will be a huge boost to the $H_2$ production research. In other application of the EGS as immobilizing agent, it will not only act as cost-effective source of immobilizing agent but also replace the complex steps of immobilization technique, with simple step of addition during fermentation. The EGS can also act as immobilizing support for attachment and growth of microorganisms. The EGS as the source of $CaCO_3$ possesses the property to maintain the pH, with supplementation in the media tending to increase the substrate conversion efficiency resulting in increased $H_2$ production. The addition of EGS as a replacement of media component will uplift the $H_2$ production industry. In terms of cost calculation, with elimination of glucose, casein polypeptone, $KH_2PO_4$, yeast extract and $MgSO_4.7H_2O$ across the media with only utilization of crude glycerol and eggshell, the media cost will reduce to 85-95% during $H_2$ production (as seen from table 14). The media chemical cost can be reduced by using the EGS, which in turn will benefit the $H_2$ production industry. Even after the end of fermentation, the spent media along with eggshell can be a perfect phosphate solubilizing biofertilizer. The role of EGS during $H_2$ production is limitless ranging from fermentation pH neutralizing agent, immobilizing agent, media supplement and nutrient source with added advantage as biofertilizer.

Example 4

Alternate Approach of Spent Media Utilization Across Mixed-Culture and Photofermentation 4.1. Crude Glycerol as Substrate The animal by-products from food processing, superstores and restaurants are recycled for biodiesel production by Rothsay®, Canada. The generated crude glycerol and wastewater sludge by Rothsay®, Canada are used in this example. The composition of crude glycerol with (w/w): 23.6% glycerol, 35.9% carbon, 5.7% moisture, 3.2% nitrogen, 3.1% ash, <1.0-0.5% methanol and 67.56% matter organic non-glycerol (MONG). The pH of crude glycerol was around 3.4±0.07.

Chemicals and reagents used across this example are purchased from Fisher Scientific®, VWR® and Lallemand®, Canada.

4.2. Seed Inoculum for Mixed-Culture

Rothsay®, carries out rigorous wastewater treatment prior to discharge of recycled water in local waterbodies. The treatment generates primary sludge (settling solid), which was used as seed inoculum to carry out mixed-culture system of hydrogen production. The primary sludge was stored at 4° C., prior to pretreatment to carry out hydrogen production using crude glycerol at higher concentration. In similar ways wastewater sludge collected from Quebec Urban Community (QUC) wastewater treatment plant (WWTP) (Quebec, QC, Canada) was analysed as possible seed inoculum along with primary sludge from biodiesel industry.

In this example, primary and wastewater sludge was subjected to heat pretreatment by transfer of 50 mL into two separate 150 mL serum bottle, pure nitrogen gas was sparged (3-4 min) for anaerobic environment; the bottle was sealed using pre-inserted septa and transferred to pre-set 100° C. Isotemp Standard Lab Ovens for 15 min. The cooled treated primary sludge was used as inoculum and transferred using sterile syringe at varying volume for hydrogen production.

4.3 Algae Pre-Culture Media and Inoculum Development

The green algae *Chlamydomonas reinhardtii* are believed to be of great interest for biohydrogen production and considered as model organisms for accumulation of energy rich compounds such as lipids. The green algae *C. reinhardtii* was grown using 100 mL of TAP growth medium (Gibco®, ThermoFisher Scientific®, USA) ready-to-use 1× with pH 7.0, under constant agitation of 60 rpm with illumination of 60-80 μmol/m$^2$/s at 20±1° C. incubation temperature.

4.4 Hydrogen Production Using Spent Media by Mixed-Culture System

The optimum condition of (20 g/L crude glycerol (CG), 20% inoculum size (InS) and pH 7.0) from our previous example 1 using wastewater sludge as seed inoculum was used in this example. A slight modification of addition of spent media in the fermentation was carried out for increased hydrogen production. The spent media characteristic are presented in the Table 15. The spent media obtained after hydrogen production was used to make-up the final volume to replace the addition of distilled water. With the presence of unutilized crude glycerol in spent media, the crude glycerol concentration in the fermentation media was varied from 15, 20 and 25 g/L concentration. The spent media with increasing concentration of crude glycerol was mixed with spent media to make-up the working volume to 40 mL. A control experiment using distilled water instated of spent media was also carried out. The pH was set at 7.0, transferred to serum bottles, surged with nitrogen, sealed with pre-inserted septa followed by sterilization at 121° C. for 15 min in autoclave. The pretreated sludge at 10% (v/v) inoculum size was transferred to the sterilized media using sterile syringe under laminar hood. The hydrogen production was carried out at 150 rpm at 37° C. for five days and all the experiments were performed in triplicates. The presented values are the average of triplicates and error bars represent the standard deviation (±) values. During fermentation every 24 h gas sample using a gas tight syringe (1 mL) was collected from the headspace into vacuumed sample vials for hydrogen analysis by gas chromatography (GC). In similar ways after five days the fermented sample was analyzed for glycerol and end metabolite concentration by GC.

TABLE 15

Characterization of spent media used across the example. Composition of spent media

| | |
|---|---|
| Ethanol (g/L) | 0.58 ± 0.18 |
| Acetate (g/L) | 2.03 ± 0.06 |
| Butyrate (g/L) | 2.37 ± 0.80 |
| 1,3-Propanediol (g/L) | 0.92 ± 0.39 |
| residual glycerol (g/L) | 5.02 ± 0.50 |
| pH | 5.56 ± 0.13 |

4.5 Hydrogen/Lipid Production Using Spent Media by Algae

The TAP growth media is optimized for *C. reinhardtii* culture and is ready-to-use, eliminates the procurement of individual media components, trace elements with tedious media preparation steps. The cost of 1 L media is around $75 (CAD) with additional freight charges. The TAP media was replaced from (50 to 0 mL) with addition of spent media (autoclaved) at different volume from (0 to 50 mL) and final mixture was transferred under laminar to serum bottles. The experimental set-up was carried out both in aerobic (for lipid production) and anaerobic (for hydrogen production) in triplicates. The anaerobic set-up was sparged with nitrogen to create anaerobic condition for hydrogen production. The 5% (v/v) inoculum size of algae was transferred to experiment set-up and bottles were incubated as same conditions as in inoculum development step.

During the incubation, cell densities was measured using electronic particle counter (Coulter Z2 particle counter, 100-μm aperture, Beckman) (Siaut, Cuiné et al. 2011), hydrogen sampling for anaerobic set-up was carried out by GC and at the end of incubation lipid/chlorophyll estimation was carried out.

4.6 Analytical Techniques 4.6.1 Hydrogen Analysis by GC

During the mixed-culture system the hydrogen gas sample collected was analyzed using gas chromatography (Varian® 3800, USA) with a set-up of thermal conductivity detector (TCD). The PoraPLOT Qe column (Agilent® technology, USA) of 3 m width under carrier gas nitrogen at flow rate of 3.5 mL/min was used. During the method run the injector, column temperature and detector temperature are set at 100° C. The area under the curve was converted to volume of gas produced (mmol) in consideration to the experimental conditions such as temperature and atmospheric pressure.

4.6.2 End-Metabolites/by-Products Analysis by GC-FID

The concentrations of glycerol and end-metabolites were determined using GC (7890B GC-Agilent®, CA) with flame ionization detector (FID) system. The column used was ZB-WAX plus with carrier helium gas at 1 mL/min flow rate in a 80° C. to 240° C. temperature profile for 8.4 min run time.

4.6.3 Estimation of Lipid Production

The total lipids at the end of fermentation was extracted from *C. reinhardtii* biomass and determined using gravimetric method. Around 35 mL of fermented media was subjected to centrifugation (4000×g) for 15 min, the cell pellet was separated from the supernatant. Around 800 μL phosphate buffer (0.05 M, pH 7.4) and 400 μm glass beads was added and transferred to cell disruptor for 10 min. To the lysed mixture, 800 μL phosphate buffer, 4 mL of chloroform, 2 mL of methanol was mixed and the lipid was extracted by 15 min of sonication. After sonication, 2 mL each of chloroform and methanol was added and the resulting mixture was made to settle for separation. The bottom organic phase containing the lipids was transferred and equal volume of 5% NaCl solution (1:1 v/v) was added. The solvent was subjected to nitrogen evaporation; the left over lipid was calculated and expressed in g/L of medium.

4.7 Results and Discussion 4.7.1 Hydrogen Production Using Spent Media by Mixed-Culture System Hydrogen production using the spent media in the absence of distilled water using primary sludge (PS), wastewater sludge (WS) and mix 1:1 (PS:WS) as seed inoculum by mixed-culture system was carried out. The mixed inoculum composed of 1:1 addition of primary sludge and wastewater sludge. The hydrogen production using the optimized condition of (InS: 20% and pH:7) in case of different seed inoculum at (15, 20 and 25 g/L) concentration of crude glycerol are presented in the Table 16. The maximum hydrogen production was around 38.12±0.84 mmol/L for WS at 20 g/L of crude glycerol. The minimum hydrogen production was around 18.96±0.13 for Mix at 15 g/L of crude glycerol as seen from Table 16.

TABLE 16

Hydrogen (mmol/L) and 1,3-Propanediol (g/L) production across different seed inoculum using different crude glycerol concentrations (g/L).

| Inoculum type | Crude glycerol g/L | Hydrogen mmol/L | 1,3-Propanediol g/L |
| --- | --- | --- | --- |
| BS-15 | 15 | 24.51 ± 0.20 | 2.83 ± 0.31 |
| BS-20 | 20 | 27.09 ± 0.83 | 5.62 ± 0.11 |
| BS-25 | 25 | 22.39 ± 0.23 | 6.72 ± 0.51 |
| WS-15 | 15 | 25.44 ± 0.62 | 3.17 ± 0.49 |
| WS-20 | 20 | 38.12 ± 0.84 | 5.46 ± 0.37 |
| WS-25 | 25 | 33.04 ± 0.61 | 6.52 ± 0.26 |
| Mix-15 | 15 | 18.96 ± 0.13 | 1.87 ± 0.08 |
| Mix-20 | 20 | 24.06 ± 0.45 | 2.98 ± 0.09 |
| Mix-25 | 25 | 19.68 ± 0.52 | 3.45 ± 0.14 |

In case of primary sludge from biodiesel industry as seed inoculum, the maximum hydrogen production was around 27.09±0.83 mmol/L with minimum was around 22.39±0.23 mmol/L. Across the three seed inoculums, the hydrogen production increased from 15 to 20 g/L. However, with further increase in the crude glycerol concentration the hydrogen production decreased. The crude glycerol concentration of 20 g/L was found to be optimum across the three inoculum for the increased hydrogen production. In this example, the spent media containing the unutilized CG along with media components benefited with increased hydrogen production (38.12±0.84 mmol/L) of around 29.53%. The spent media contains dead biomass, residual media nutrients, biomolecules and unutilized glycerol which together act as a supplementary source of nutrients for the mixed-culture system for hydrogen production.

The advantage of mixed-culture system to grow on broader choice of organic waste feedstocks requiring easy and simple pretreatment conditions followed by the ability to reuse the spent media for hydrogen production. The choice of wastewater sludge as seed inoculum along with heat-shock treatment proved to be the best combination for the utilization of spent media along with crude glycerol as substrate for increased hydrogen production. In case of seed inoculum biodiesel primary sludge, the hydrogen production reached a maximum of 27.09±0.83 mmol/L at 20 g/L of CG. The objective of using the primary sludge was to identify the microorganism community able to degrade glycerol at higher concentration, as primary sludge is in contact with residual glycerol after biodiesel production. To support, the primary sludge possessed the ability to produce more 1,3-Propanediol (1,3-PD) (6.72±0.51 g/L) across other seed inoculum as seen in Table 16. In case of monitoring the hydrogen production in most cases production of 1,3-PD is also determined, the values of these two determine the glycerol fermentation pathway. The production of 1,3-PD increases during the glycerol fermentation as reductive pathway favors over oxidative pathway with decreased production of hydrogen. This is true as CG was 25 g/L, hydrogen production decreased to 22.39±0.23 mol/L with increased production of 1,3-PD reaching a high of around 6.72±0.51 g/L in the case of primary sludge as seed inoculum. The ability to degrade glycerol at higher concentration and produce a value-added compound 1,3-PD, in one way or the other will help the biodiesel industry. The combination of two sludge (primary sludge: wastewater sludge) at 1:1 ratio as seed inoculum was also investigated for hydrogen production. The maximum hydrogen production was around 24.06±0.45 mmol/L and for 1,3-PD the maximum was around 3.45±0.14 g/l in case of mix sludge as seen from the Table 17. In order to exploit the property of hydrogen production from wastewater sludge and 1,3-PD from primary sludge, the mix seed inoculum was investigated. The ratio of 1:1 tried was not sufficient in exploiting the property of both the seed inoculum. A combination of different ratios can be tried to get the increased production for both hydrogen and 1,3-PD.

The results from the example determined the wastewater sludge with initial heat-shock pretreatment, followed with 20% inoculum size at 20 g/L concentration of crude glycerol in presence of spent media as a replacement of distilled water resulted in increased hydrogen production. The municipal wastewater is the final repository of various complex microorganisms possessing the property of working at higher substrate concentration with ability to degrade complex substrate and capability to reutilize the spent media with ease.

4.7.2 Lipid Production Using Spent Media by Algae

TABLE 17

Lipid (g/L) production across different seed inoculum using different volume of spent (mL) and fresh media (mL).

| S. No. | Spent Media (mL) | Fresh Media (mL) | Lipid (g/L) |
| --- | --- | --- | --- |
| L1 | 0 | 50 | 0.045 ± 0.006 |
| L2 | 10 | 40 | 0.067 ± 0.006 |
| L3 | 20 | 30 | 0.072 ± 0.002 |
| L4 | 30 | 20 | 0.098 ± 0.007 |
| L5 | 40 | 10 | 0.036 ± 0.004 |
| L6 | 50 | 0 | 0.010 ± 0.002 |

Lipid production using *C. reinhardtii* at different volume of spent and fresh media (TAP growth media) was carried out as presented in Table 17. The purpose was to reduce the utilization of fresh media (FM) and utilize the spent media (SM) during lipid production. The maximum lipid production was around 0.098±0.07 g/L for the mixture of (SM: 30, FM: 20) and the minimum was around 0.010±0.02 g/l in case of (SM: 0, FM: 50). In the presence of completed fresh media (50 mL) the lipid production was around 0.045±0.006 g/L in comparison to 0.010±0.002 g/L in presence of complete spent media (50 mL). With the increase in the concentration of the spent media from (0 to 30 mL), the production of lipid increased from 0.045 to 0.098 g/L. However, with further increase from 30 mL of spent media, the lipid production decreased reaching a minimum of 0.010±0.002 g/L. The maximum lipid production was 0.098±0.007 g/L. The spent media composition with organic/solvents and unutilized glycerol at minimum concentration tend to favor the growth of C. reinhardtii. With further increase in the volume of the spent media, the concentration of these compounds increased resulting with an inhibition on the growth of growth C. reinhardtii with decreased lipid production.

The spent media composed of acetate and butyrate, which are utilized as substrate during photofermentation. In case of C. reinhardtii growth media, the external addition of organic acids is carried out along with complex media and micronutrients requirement during the lipid production. C. reinhardtii possess the ability to grown on the acetate and was supplemented with glacial acetic acid with concentration of 20 mM as carbon source in the minimal medium. In order to determine the metabolite utilization across the spent media during lipid production, analysis of acetate, butyrate along with glycerol concentration before and after lipid production was carried out. The results of the metabolite concentration (g/L) along with utilization percentage (%) are presented in the Table 18.

TABLE 18

The glycerol and metabolite concentration (g/L) along with percentage of utilization across different volume sets of lipid production.

| Mixture volume | Acetate (g/L) | Butyrate (g/L) | Glycerol (g/L) |
|---|---|---|---|
| Before-L1 | 1.083 | 0.021 | 2.420 |
| After-L1 | 0.325 | 0.020 | 1.778 |
| % utilization | 70.00 | 3.58 | 26.52 |
| Before-L2 | 1.157 | 0.395 | 2.667 |
| After-L2 | 0.053 | 0.294 | 1.631 |
| % utilization | 95.39 | 25.52 | 38.84 |
| Before-L3 | 1.314 | 0.760 | 3.010 |
| After-L3 | 0.034 | 0.544 | 1.727 |
| % utilization | 97.44 | 28.45 | 42.62 |
| Before-L4 | 1.387 | 1.153 | 3.712 |
| After-L4 | 0.013 | 0.601 | 1.646 |
| % utilization | 99.03 | 47.88 | 55.66 |
| Before-L5 | 1.489 | 1.529 | 4.614 |
| After-L5 | 0.018 | 0.894 | 3.279 |
| % utilization | 98.81 | 41.56 | 28.92 |
| Before-L6 | 1.527 | 1.635 | 4.846 |
| After-L6 | 0.049 | 1.365 | 3.720 |
| % utilization | 96.80 | 16.50 | 23.23 |

The results of the lipid production suggested the mixture volume L4 (SM: 30, FM: 20) produced maximum lipid in comparison to other mixture volumes. In case of L4 the percentage utilization for glycerol was around 55.66%, butyrate was around 47.77% and acetate was highest with 99.03%. The percentage utilization of these compounds was highest across the other mixture volumes, supporting the results with lipid production. The metabolite ethanol and 1,3-PD was also analyzed, however there were little changes in the percentage utilization (data not shown). The percentage of glycerol, acetate and butyrate percentage utilization increased with increase in the spent media volume until 30 mL. However, further increase in the volume from 40 to 50 mL there was a decrease in the percentage utilization, similar to lipid production as presented in Table 18. The optimum concentration of acetate for the growth of C. reinhardtii is around 20 mM, in case of volume mixture L5 and L6 the acetate limits the optimum conditions and inhibits the growth resulting in decreased lipid production. In case of glycerol the optimum concentration is around 30-50 mM, which in case of L4 was within the limits. However, in case of the L5 and L6, the concentration of glycerol reached the limiting concentration resulting in decreased lipid production. The optimum mixture volume (3:2) of spent media (30 mL) and fresh media (20 mL) resulted in the increased lipid production along with maximum percentage utilization of the metabolites from the spent media.

The presence of acetate and butyrate in the spent media, tend to act as carbon source and help towards the growth of C. reinhardtii. The C. reinhardtii dependent on the organic acids for the growth, the external addition of organic acids was supplemented with the utilization of spent media in an efficient closed system approach. The spent media from the dark fermentation utilizes around 60-70% of substrate for metabolite generation during hydrogen production, as shown above. The effective approach of utilizing these metabolites can be for the growth of photofermenting organisms such as C. reinhardtii for lipid production.

4.7.3 Efficient Closed System Approach for Biodiesel Industry

Figure 15:
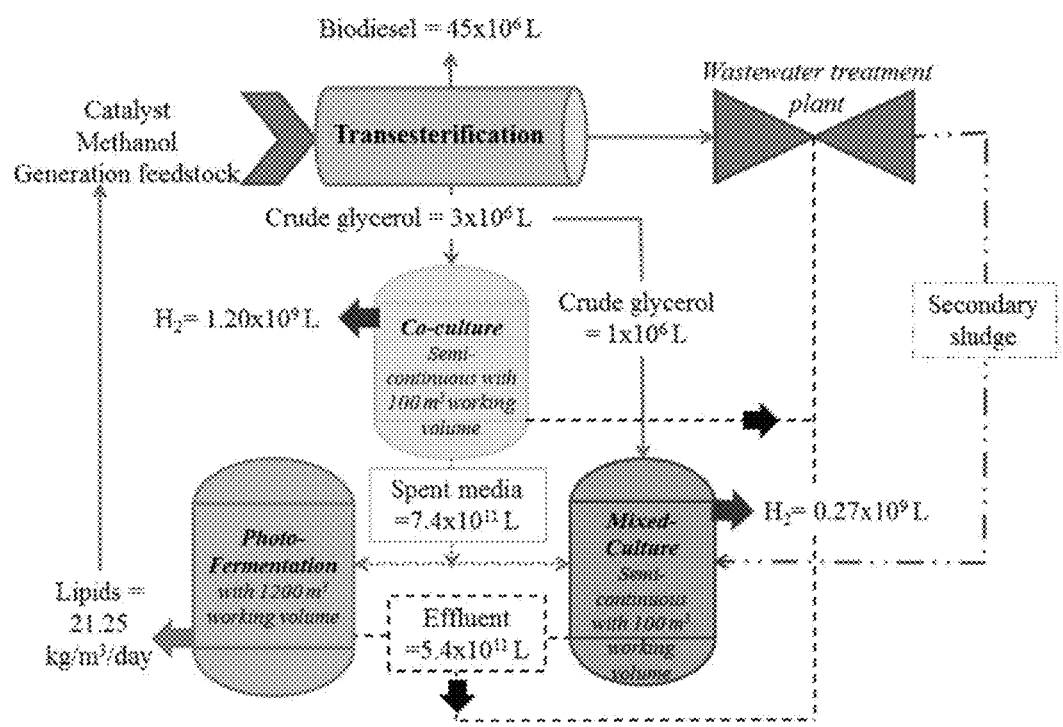
FIG. 15 illustrates an efficient closed system approach for biodiesel industry for valorization of by-product crude glycerol into hydrogen production by co-culture system, utilization of the generated spent media across mixed-culture for hydrogen and photo-fermentation for lipid production, according to an embodiment of the present invention.

The increasing demand of biodiesel as fuel resulted in the exponential increase of the biodiesel industry across the world. The biggest problem for biodiesel industry is the generation of by-product crude glycerol which renders the situation unprofitable. The generation of excess crude glycerol in the market resulted in decreasing market value and shut down of the glycerin industry. Researchers are finding ways to valorize crude glycerol into value-added chemicals. Hydrogen production using crude glycerol is the best approach requiring minimum downstream purification steps in comparison to other value-added chemicals. In addition, the high reducing state of glycerol as substrate favors increased hydrogen yield in comparison to other organic substrate. The approach of co-culture system resulted in increased hydrogen production over mono-culture system using crude glycerol as substrate, as shown above. After the hydrogen production, the spent media generated composed of organic/solvents, media components and residual glycerol may act as supplementary source for photofermentation during hydrogen production. In a proposed efficient closed system for biodiesel industry as represented in FIG. 15, the approach is to minimize the waste generated during hydrogen production and utilize it in an efficient approach to uplift biodiesel industry. In this example the spent media obtained after co-culture system of hydrogen production was utilized for media preparation instead of distilled water for the mixed-culture system of hydrogen. The efficient closed system can use the primary sludge generated from wastewater treatment plant as seed inoculum with simple heat-shock treatment. The mixed-culture successfully resulted in utilization of crude glycerol, spent media, along with primary sludge to produce hydrogen, which can be used as in-house energy fuel for biodiesel industry. In another approach of closed system, the spent media was successfully replaced the fresh media and also resulted with increased lipid production. The utilization of spent media helps to minimize the use of fresh media, thereby decreasing the media cost for lipid production. In addition, the produced lipid can be used as generation feedstock for the biodiesel industry.

The closed system approach of using crude glycerol and primary sludge for hydrogen production and utilizing the spent media for lipid production completes the circle for the biodiesel industry. The decreasing market value of crude glycerol with the approach of efficient closed system will have a new market value. The small- and medium-scale biodiesel industry approach is to recycle around 99-100% of its inputs into value-added products. The efficient closed system can help to reach the figures requiring minor production modification and the long term result will uplift small- and medium-scale biodiesel industry.

4.8 Conclusions

The spent media generated during dark fermentation containing organic compounds and unutilized substrate with media components is of great interest as a promising choice for waste utilization. The spent media can be used across different platforms to generate value-added chemicals. In this example, the spent media is used to replace distilled water used for media preparation during hydrogen production using mixed-culture system. The heat-shock pretreatment of wastewater sludge at 20% inoculum volume in presence of crude glycerol concentration of 20 g/L resulted in increased hydrogen production around 38.12±0.84 mmol/L. In another approach, the spent media was replaced with fresh media across *C. reinhardtii* growth during lipid production. The mixture volume of spent media (30 mL) and fresh media (20 mL) resulted with 0.098±0.007 g/L of lipid production. The spent media was used across both mixed-culture and photo-fermentation for hydrogen and lipid production. The efficient closed system approach of utilizing crude glycerol and spent media provides a new approach of valorization of crude glycerol and also uplifts the biodiesel industry to be competitive in the market.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A process for producing hydrogen gas ($H_2$) from fermentation of crude glycerol in a bioreactor, comprising the steps of:
   providing in the bioreactor, a fermentation mixture comprising a supplemented fermentation medium which comprises a first volume of said crude glycerol, a hydrogen producing microorganism and a natural source of calcium carbonate ($CaCO_3$) in a particulate form at a concentration of from 0.25% to 4% (w/v),
   operating the bioreactor under a fermentative hydrogen production condition, and
   introducing a second volume of said crude glycerol, and removing a volume of said fermentation mixture equal to said second volume of said crude glycerol, to maintain a constant total volume of said fermentation mixture,
   wherein said natural source of calcium carbonate is selected from the group consisting of an eggshell, a seashell, a cuttlefish bone, limestone, chalk, marble and calcite.

2. The process of claim 1, wherein said process is a continuous process or a semi-continuous process.

3. The process of claim 1, wherein said supplemented fermentation medium comprises an initial crude glycerol concentration from 2.5 to 20 g/L.

4. The process of claim 1, wherein said second volume of said crude glycerol is at a concentration from 60 g/L to 120 g/L.

5. The process of claim 1, wherein said second volume of said crude glycerol is introduced at a constant feed rate.

6. The process of claim 1, further comprising collecting said hydrogen gas ($H_2$) from said bioreactor, and wherein said collecting is continuous collecting or discontinuous collecting.

7. The process of claim 6, wherein said discontinuous collecting is by bubbling a gas in said fermentation mixture to release dissolved hydrogen gas therefrom.

8. The process of claim 1, wherein said fermentative hydrogen production condition comprises a pH of about 6.

9. The process of claim 1, wherein said fermentation mixture further comprises a mixed fermentation medium comprising crude glycerol and a fermentable industrial by-product.

10. The process of claim 1, wherein said crude glycerol is untreated crude glycerol.

11. The process of claim 9, wherein said supplemented fermentation medium is supplemented with a supplement selected from the group consisting of water, a salt, a nutrient, spent fermentation medium, a surfactant, and combinations thereof.

12. The process of claim 1, wherein said supplemented fermentation medium is supplemented with a pH control agent selected from the group consisting of NaOH, KOH, and combinations thereof.

13. The process of claim 11, wherein said salt comprises $KH_2PO_4$, $MgSO_4.7H_2O$, $Na_2HPO_4$ or combinations thereof.

14. The process of claim 11, wherein said nutrient is selected from the group consisting of yeast extract, a peptone, urea, slaughterhouse liquid waste, brewery waste biomass and combinations thereof.

15. The process of claim 1, wherein said hydrogen producing microorganism comprises a co-culture of hydrogen producing microorganism or a mixed culture of hydrogen producing microorganism.

16. The process of claim 1, wherein said hydrogen producing microorganism comprises *Enterobacter aerogenes* (*E. aerogenes*), *Clostridium butyricum* (*C. butyricum*), *Chlamydomonas reinhardtii*, or combinations thereof.

17. The process of claim 1, wherein said hydrogen producing microorganism comprises a co-culture of *E. aerogenes* and *C. butyricum*.

18. The process of claim 11, wherein said surfactant is polysorbate 80.

19. The process of claim 18, wherein said polysorbate 80 is at concentration of about 10 mg/L to about 25 mg/L.

20. The process of claim 1, wherein said supplemented fermentation medium is supplemented with an immobilization support selected from the group consisting of a plastic microsphere, a plastic particle, a silica microsphere, a silica particle, and combinations thereof.

21. The process of claim 1, wherein said eggshell is in particulate form and said eggshell particles are of a size from 33 μm to 75 μm.

* * * * *